US011617783B2

(12) United States Patent
Rodino-Klapac et al.

(10) Patent No.: US 11,617,783 B2
(45) Date of Patent: Apr. 4, 2023

(54) REPAIRING A MUTANT HUMAN TITIN GENE USING CRISPR TECHNOLOGY

(71) Applicant: RESEARCH INSTITUTE AT NATIONWIDE CHILDREN'S HOSPITAL, Columbus, OH (US)

(72) Inventors: Louise Rodino-Klapac, E. Groveport, OH (US); Rachael Potter, Dublin, OH (US)

(73) Assignee: RESEARCH INSTITUTE AT NATIONWIDE CHILDREN'S HOSPITAL, Columbus, OH (US)

( * ) Notice: Subject to any disclaimer, the term of this patent is extended or adjusted under 35 U.S.C. 154(b) by 0 days.

(21) Appl. No.: 15/776,714

(22) PCT Filed: Nov. 15, 2016

(86) PCT No.: PCT/US2016/062052
§ 371 (c)(1),
(2) Date: May 16, 2018

(87) PCT Pub. No.: WO2017/087395
PCT Pub. Date: May 26, 2017

(65) Prior Publication Data
US 2018/0360921 A1    Dec. 20, 2018

Related U.S. Application Data

(60) Provisional application No. 62/255,887, filed on Nov. 16, 2015.

(51) Int. Cl.
| | |
|---|---|
| *C12N 5/00* | (2006.01) |
| *A61K 38/39* | (2006.01) |
| *C12N 9/22* | (2006.01) |
| *C12N 15/90* | (2006.01) |
| *A61K 48/00* | (2006.01) |
| *C07K 14/47* | (2006.01) |
| *C12N 15/88* | (2006.01) |
| *C12N 15/113* | (2010.01) |
| *A61P 21/00* | (2006.01) |
| *C12N 15/11* | (2006.01) |

(52) U.S. Cl.
CPC .............. *A61K 38/39* (2013.01); *A61K 48/00* (2013.01); *A61K 48/005* (2013.01); *A61P 21/00* (2018.01); *C07K 14/4716* (2013.01); *C12N 9/22* (2013.01); *C12N 15/11* (2013.01); *C12N 15/113* (2013.01); *C12N 15/88* (2013.01); *C12N 15/907* (2013.01); *C12N 2310/20* (2017.05); *C12N 2750/14143* (2013.01); *C12N 2800/80* (2013.01)

(58) Field of Classification Search
CPC .................. C12N 15/11; C12N 9/22
USPC .................. 514/44; 424/93.2, 93.21
See application file for complete search history.

(56) References Cited

U.S. PATENT DOCUMENTS

| | | |
|---|---|---|
| 5,173,414 A | 12/1992 | Lebkowski et al. |
| 5,658,776 A | 8/1997 | Flotte et al. |
| 5,786,211 A | 7/1998 | Johnson |
| 5,871,982 A | 2/1999 | Wilson et al. |
| 6,258,595 B1 | 7/2001 | Gao et al. |
| 2010/0112694 A1 | 5/2010 | Marban |
| 2011/0023139 A1 | 1/2011 | Weinstein et al. |
| 2013/0171172 A1 | 7/2013 | Richard et al. |
| 2014/0273231 A1 | 9/2014 | Zhang et al. |
| 2015/0125429 A1 | 5/2015 | Perlingeiro et al. |
| 2015/0232883 A1* | 8/2015 | Dahlman ................. C12N 9/22 435/462 |
| 2015/0238627 A1* | 8/2015 | Leger .................. C12N 15/113 514/20.9 |

FOREIGN PATENT DOCUMENTS

| | | |
|---|---|---|
| WO | WO-1995/013365 A1 | 5/1995 |
| WO | WO-1995/013392 A1 | 5/1995 |
| WO | WO-1996/017947 A1 | 6/1996 |
| WO | WO-1997/006243 A1 | 2/1997 |
| WO | WO-1997/008298 A1 | 3/1997 |
| WO | WO-1997/009441 A2 | 3/1997 |
| WO | WO-1997/021825 A1 | 6/1997 |
| WO | WO-1999/011764 A2 | 3/1999 |
| WO | WO-2001/083692 A2 | 11/2001 |
| WO | WO-2013/176772 A1 | 11/2013 |
| WO | WO-2014/093622 A2 | 6/2014 |
| WO | WO-2014/093712 A1 | 6/2014 |
| WO | WO-2014/204725 A1 | 12/2014 |
| WO | WO-2015/021457 A2 | 2/2015 |

OTHER PUBLICATIONS

NG_011618, reference sequence for the human titin gene, 2010.*
Ceyhan-Birsoy (Neurology, 2013, vol. 81, p. 1205-1214).*
Cox (Nature Med., 2015, vol. 21, p. 121-131).*
Bang et al., The complete gene sequence of titin, expression of an unusual approximately 700-kDa titin isoform, and its interaction with obscurin identify a novel Z-line to I-band linking system, *Circ. Res.* 89:1065-72 (2001).
Bearzi et al., Human cardiac stem cells, *Proc. Natl. Acad. Sci. USA.* 104:14068-73 (2007).
Behlke, Chemical modification of siRNAs for in vivo use, *Oligonucleotides.* 18:305-319 (2008).
Belfort et al., Homing endonucleases: from genetic anomalies to programmable genomic clippers, *Methods Mol. Biol.* 1123:1-26 (2014).
Boch et al., Breaking the code of DNA binding specificity of TAL-type III effectors, *Science.* 326:1509-12(2009).

(Continued)

*Primary Examiner* — Michael C Wilson
(74) *Attorney, Agent, or Firm* — Marshall, Gerstein & Borun LLP

(57) ABSTRACT

The present application provides materials and methods for treating a patient with a titin-based myopathy, particularly a titin-based cardiomyopathy, and/or other titinopathy. In addition, the present application provides materials and methods for editing the titin gene in a cell by genome editing.

11 Claims, 9 Drawing Sheets

Specification includes a Sequence Listing.

(56) References Cited

OTHER PUBLICATIONS

Boissel et al., Assembly and characterization of megaTALs for hyperspecific genome engineering applications, *Methods Mol. Biol.* 1239:171-96 (2015).
Boissel et al., megaTALs: a rare-cleaving nuclease architecture for therapeutic genome engineering, *Nucleic Acids Res.* 42:2591-601 (2014).
Bramsen et al., Development of therapeutic-grade small interfering RNAs by chemical engineering, *Front. Genet.* 20:154 (2012).
Carter, Adeno-associated virus vectors, *Current Opinion in Biotechnology.* 3:533-539 (1992).
Ceccadi et al., Homologous recombination-deficient tumors are hyper-dependent on POLQ-mediated repair, *Nature.* 518:258-262 (2015).
Cekaite et al., Gene expression analysis in blood cells in response to unmodified and 2'-modified siRNAs reveals TLR-dependent and independent effects, *J. Mol. Biol.* 365:90-108 (2007).
Centner et al., Identification of muscle specific ring finger proteins as potential regulators of the titin kinase domain, *J. Mol. Biol.* 306:717-26 (2001).
Cermak et al., Efficient design and assembly of custom TALEN and other TAL effector-based constructs for DNA targeting, *Nucleic Acids Res.* 39:e82 (2011).
Cermak et al., Efficient design and assembly of custom TALENs using the Golden Gate platform, *Methods Mol. Biol.* 1239:133-59 (2015).
Ceyhan-Birsoy et al., Recessive truncating titin gene, TTN, mutations presenting as centronuclear myopathy, *Neurology.* 81:1205-14 (2013).
Chauveau et al., A rising titan: TTN review and mutation update, *Human Mutation.* 35:1046-59 (2014).
Chernolovskaya et al., Chemical modification of siRNA, *Curr. Opin. Mol. Ther.* 12:158-67 (2010).
Cho et al., DNA repair: Familiar ends with alternative endings, *Nature.* 518:174-6 (2015).
Clark et al., A stable cell line carrying adenovirus-inducible rep and cap genes allows for infectivity titration of adeno-associated virus vectors, *Gene Ther.* 3:1124-32 (1996).
Clark et al., Highly purified recombinant adeno-associated virus vectors are biologically active and free of detectable helper and wild-type viruses, *Hum. Gene Ther.* 10:1031-9 (1999).
Cox et al., Therapeutic genome editing: propects and challenges, *Nat. Med.* 21:121-31 (2015).
D'Amario et al., Functionally competent cardiac stem cells can be isolated from endomyocardial biopsies of patients with advanced cardiomyopathies, *Circ. Res.* 108:857-61 (2011).
Deleavey et al., Chemical modification of siRNA, Curr. Protoc. Nucleic Acid Chem. Chapter 16:Unit16.3 (2009).
Doench et al., Optimized sgRNA design to maximize activity and minimize off-target effects of CRISPR-Cas9, *Nat. Biotechnol.* 34:184-191 (2016).
Dreier et al., Development of zinc finger domains for recognition of the 5'-ANN-3' family of DNA sequences and their use in the construction of artificial transcription factors, *J. Biol. Chem.* 276:29466-78 (2001).
Dreier et al., Development of zinc finger domains for recognition of the 5'-CNN-3' family DNA sequences and their use in the construction of artificial transcription factors, *J. Biol. Chem.* 280:35588-97 (2005).
Dreier et al., Insights into the molecular recognition of the 5'-GNN-3' family of DNA sequences by zinc finger domains, *J. Mol. Biol.* 303:489-502 (2000).
Fonfara et al., Phylogeny of Cas9 determines functional exchangeability of dual-RNA and Cas9 among orthologous type II CRISPR-Cas systems, *Nucleic Acids Res.* 42:2577-90 (2014).
Foye, Whole Genome Sequencing Solved Our Family's Genetic Mystery: Titin, *Narrat. Inq. Bioeth.* 5:206-8 (2015).
Fucini et al., Adenosine modification may be preferred for reducing siRNA immune stimulation, *Nucleic Acid Ther.* 22:205-210 (2012).
Gaglione et al., Recent progress in chemically modified siRNAs, *Mini. Rev. Med. Chem.* 10:578-95 (2010).
Gao et al., A novel and efficient model of coronary artery ligation and myocardial infarction in the mouse, *Circ. Res.* 107:1445-53 (2010).
Gao et al., A novel and efficient model of coronary artery ligation in the mouse, *Methods Mol. Biol.* 1037:299-311 (2013).
Gautel et al., The central Z-disk region of titin is assembled from a novel repeat in variable copy numbers, *Journal of Cell Science.* 109:2747-2754 (1996).
Gebeyehu et al., novel biotinylated nucleotide-analogs for labeling and colorimetric detection of DNA, *Nucl. Acids Res.* 15:4513-34 (1987).
GenBank Accession No. AF028704.1, Adeno-associated virus 6, complete genome, Jan. 12, 1998.
GenBank Accession No. AF028705.1, Adeno-associated virus 3B, complete genome, Jan. 12, 1998.
GenBank Accession No. AX753250.1, Sequence 5 from Patent EP1310571, Jun. 23, 2003.
GenBank Accession No. AY631965.1, Adeno-associated virus 10 nonstructural protein and capsid protein genes, complete cds, Nov. 30, 2004.
GenBank Accession No. AY631966.1, Adeno-associated virus 11 nonstructural protein and capsid protein genes, complete cds, Nov. 30, 2004.
GenBank Accession No. DQ813647.1, Adeno-associated virus 12 Rep78 and VP1 genes, complete cds, Feb. 20, 2008.
GenBank Accession No. EU285562.1, Adeno-associated virus 13 nonstructural protein and capsid protein genes, complete cds, Sep. 23, 2008.
GenBank Accession No. NC_001401.2, Adeno-associated virus-2, complete genome, Aug. 13, 2018.
GenBank Accession No. NC_001729.1, Adeno-associated virus-3, complete genome, Aug. 13, 2018.
GenBank Accession No. NC_001829.1, Adeno-associated virus-4, complete genome, Aug. 13, 2018.
GenBank Accession No. NC_002077.1, Adeno-associated virus-1, complete genome, Aug. 13, 2018.
GenBank Accession No. NC_006152.1, Adeno-associated virus 5, complete genome, Aug. 13, 2018.
GenBank Accession No. NC_006260.1, Adeno-associated virus-7, complete genome, Aug. 13, 2018.
GenBank Accession No. NC_006261.1, Adeno-associated virus-8, complete genome, Aug. 13, 2018.
Gerull et al., Identification of a novel frameshift mutation in the giant muscle filament titin in a large Austrailian family with dilated cardiomyopathy, *J. Mol. Med. (Berl).* 84:478-83 (2006).
Gerull et al., Mutations of TTN, encoding the giant muscle filament titin, cause familial dilated cardiomyopathy, *Nat. Genet.* 30:201-4 (2002).
Goeddel, Gene Expression Technology: Methods in Enzymology, Academic Press, San Diego, pp. 185(1990).
Gramlich et al., Stress-induced dilated cardiomyopathy in a knock-in mouse model mimicking human titin-based disease, *J. Mol. Cell Cadiol.* 47:352-8 (2009).
Granzier et al., Deleting titin's I-band/A-band junction reveals critical roles for titin in biomechanical sensing and cardiac function, *Proc. Natl. Acad. Sci. USA.* 111:14589-94 (2014).
Grieger et al., Production and characterization of adeno-associated viral vectors, *Nat. Protoc.* 1:1412-28 (2006).
Guilinger et al., Fusion of catalytically inactive Cas9 to FokI nuclease improves the specificity of genome modification, *Nat. Biotechnol.* 32:577-82 (2014).
Hafez et al., Homing endonucleases: DNA scissors on a mission, *Genome.* 55:553-69 (2012).
Herman et al., Truncations of titin causing dilated cardiomyopathy, *N. Engl. J. Med.* 366:619-28 (2012).
Hermonat et al., Use of adeno-associated virus as a mammalian DNA cloning vector: transduction of neomycin resistance into mammalian tissue culture cells, *Proc. Natl. Acad. Sci. USA.* 81:6466-70 (1984).

(56) References Cited

OTHER PUBLICATIONS

Horii et al., Validation of microinjection methods for generating knockout mice by CRISPR/Cas-mediated genome engineering, Sci Rep. 4:4513 (2014).
International Preliminary Reporton Patentability, PCT/US2016/062052 (dated May 22, 2018).
International Search Report and Written Opinion, PCT/US2016/062052 (dated Feb. 7, 2017).
Itoh-Satoh et al., Titan mutations as the molecular basis for dilated cardiomyopathy, Biochem. Biophys. Res. Commun. 291:385-93 (2002).
Jaber et al., Titin isoforms, extracellular matrix, and global chamber remodeling in experimental dilated cardiomyopathy: functional implications and mechanistic insight, Circ. Heart Fail. 1:192-9 (2008).
Jinek et al., A programmable dual-RNA-guided DNA endonuclease in adaptive bacterial immunity, Science. 337:816-21 (2012).
Judge et al., Design of noninflammatory synthetic siRNA mediating potent gene silencing in vivo, Mol. Ther. 13:494-505 (2006).
Kariko et al., Supression of RNA recognition by toll-like receptors: the impact of nucleoside modification and the evolutionary origin of RNA, Immunity. 23:165-75 (2005).
Kent et al., Mechanism of microhomology-mediated end-joining promoted by human DNA polymerase theta, Nat. Struct. Mol. Biol. 22:230-237 (2015).
Kleinstiver et al., The I-Tevi nuclease and linker domains contribute to the specificity of monomeric TALENs, G3 (Bethesda). 4:1155-65 (2014).
Kole et al., RNA therapeutics: Beyond RNA interference and antisense oligonucleotides, Nat. Rev. Drug Discov. 11:125-140 (2012).
Kolmerer et al., Genomic organization of M line titin and its tissue-specific expression in two distinct isoforms, J. Mol. Biol. 256:556-63 (1996).
Kormann et al., Expression of therapeutic proteins after delivery of chemically modified mRNA in mice, Nat. Biotechnol. 29:154-7 (2011).
Kornberg et al., The early history of DNA polymerase: a commentary by Arthur Kornberg, Biochimica et Biophysica Acta. 1000:53-56 (1989).
Labeit et al., Titins: giant proteins in charge of muscle ultrastructure and elasticity, Science. 270:293-6 (1995).
Laughlin et al., Cloning of infectious adeno-associated virus genomes in bacterial plasmids, Gene. 23:65-73 (1983).
Lebkowski et al., Adeno-associated virus: a vector system for efficient introduction and integration of DNA into a variety of mammalian cell types, Mol. Cell. Biol. 8:3988-3996 (1988).
Lewinter et al., Cardiac titin and heart disease, J. Cardiovasc. Pharmacol. 63:207-12 (2014).
Lewinter, Titin isoforms in heart failure: are there benefits to supersizing, Circulation. 110:109-11 (2004).
Li et al., Intracoronary administration of cardiac stem cells in mice: a new, improved technique for cell therapy in murine models, Basic Res. Cardiol. 106:849-64 (2011).
Li et al., Modularly assembled designer TAL effector nucleases for targeted gene knockout and gene replacement in eukaryotes, Nucleic Acids Res. 39:6315-25 (2011).
Liu et al., Validated zinc finger protein designs for all 16 GNN DNA triplet targets, J. Biol. Chem. 277:3850-6 (2002).
Ma et al., Pol III Promoters to express small RNAs: Delineation of transcription initiation, Mol. Ther. Nucleic Acids. 3:e161 (2014).
Mak et al., The crystal structure of TAL effector PthXo1 bound to its DNA target, Science. 335:716-9 (2012).
Makarenko et al., Passive stiffness changes caused by upregulation of compliant titin isoforms in human dilated cardiomyopathy hearts, Circ. Res. 95:708-16 (2004).
Mashiko et al., Generation of mutant mice by pronuclear injection of circular plasmid expressing Cas9 and single guided RNA, Sci. Rep. 3:3355 (2013).
Mateos-Gomez et al., Mammalian Polymerase theta promotes alternative-NHEJ amd suppresses recombination, Nature. 518:254-257 (2015).
McLaughlin et al., Adeno-associated virus general transduction vectors: analysis of proviral structures, J. Virol. 62:1963-73 (1988).
McNally et al., The genetic landscape of cardiomyopathy and its role in heart failure, Cell. Metab. 21:174-182 (2015).
Moscou et al., A simple cipher governs DNA recognition by TAL effectors, Science. 326:1501 (2009).
Muzyczka, Use of adeno-associated virus a general transduction vector for mammalian cells, Curr. Top Microbiol. Immunol. 158:97-129 (1992).
Obermann et al., Molecular structure of the sarcomeric M band: mapping of titin and myosin binding domains in myomesin and the identification of a potential regulatory phosphorylation site in myomesin, EMBO J. 16:211-20 (1997).
Paul et al., Increased viral titer through concentration of viral harvests from retroviral packaging lines, Hum. Gene Ther. 4:609-615 (1993).
Peer et al., Special delivery: targeted therapy with small RNAs, Gene. Ther. 18:1127-33 (2011).
Peled et al., Titin mutation in familial restrictive cardiomyopathy, Int. J. Cardiol. 171:24-30 (2014).
Perrin et al., An experimental rabies vaccine produced with a new BHK-21 suspension cell culture process: use of serum-free medium and perfusion-reactor system, Vaccine. 13:1244-50 (1995).
Rabinowitz et al., Cross-packaging of a single adeno-associated virus (AAV) type 2 vector genome into multiple AAV serotypes enables transduction with broad specificity, J. Virol. 76:791-801 (2002).
Ran et al., In vivo genome editing using Staphylococcus aureus Cas9, Nature. 520:186-91 (2015).
Roberts et al., Integrated allelic, transcriptional, and phenomic dissection of the cardiac effects of titin truncations in health and disease, Sci. Transl. Med. 7:270ra6 (2015).
Rodino-Klapac et al., A translational approach for limb vascular delivery of the micro-dystrophin gene without high volume or high pressure for treatment of Duchenne muscular dystrophy, J. Transl. Med. 5:45 (2007).
Samulski et al., Cloning of adeno-associated virus into pBR322:rescue of intact virus from the recombinant plasmid in human cells, Proc. Natl. Acad. Sci. USA. 79:2077-81 (1982).
Samulski et al., Helper-free stocks of recombinant adeno-associated viruses: normal integration does not require viral gene expression, J. Virol. 63:3822-8 (1989).
Sander et al., CRISPR-Cas systems for editing, regulating and targeting genomes, Nat. Biotechnol. 32:347-55 (2014).
Sanganalmath et al., Cell therapy for heart failure: a comprehensive overview of experimental and clincal studes, current challenges, and future directions, Circ. Res. 113:810-34 (2013).
Sanghvi et al., Antisense Research and Applications, CRC Press, Boca Raton, pp. 276-278 (1993).
Segal et al., Toward controlling gene expression at will: selection and design of zinc finger domains recognizing each of the 5'-GNN-3' DNA target sequences, Proc. Natl. Acad. Sci. USA. 96:2758-63 (1999).
Senapathy et al., Molecular cloning of adeno-associated virus variant genomes and generation of infectious virus by recombinant in mammalian cells, J. Biol. Chem. 259:4661-4666 (1984).
Siu et al., Familial dilated cardiomyopathy locus maps to chromosome 2q31, Circulation. 99:1022-6 (1999).
Sorimachi et al., Tissue-specific expression and alpha-actinin binding properties of the Z-disc titin: implications for the nature of vertebrate Z-discs, J. Mol. Biol. 270:688-95 (1997).
Soutschek et al., Therapeutic silencing of an endogenous gene by systemic administration of modified siRNAs, Nature. 432:173-8 (2004).
Steentoft et al., Precision genome editing: a small revolution for glycobiology, Glycobiology. 24:663-80 (2014).
Torella et al., Resident cardiac stem cells, Cell Mol. Life Sci. 64:661-73 (2007).

(56) References Cited

OTHER PUBLICATIONS

Tratschin et al., A human parvovirus, adeno-associated virus, as a eucaryotic vector: transient expression and encapsidation of the procaryotic gene for chloramphenicol acetyltransferase, *Mol. Cell Biol.* 4:2072-81 (1984).
Tratschin et al., Adeno-associated virus vector for high-frequency integration, expression, and rescue of genes in mammalian cells, *Mol. Cel. Biol.* 5:3251-60 (1985).
Tsai et al., Dimeric CRISPR RNA-guided FokI nucleases for highly specific genome editing, *Nat. Biotechnol.* 32:569-76 (2014).
Tsai et al., GUIDE-seq enables genome-wide profiling of off-target cleavage by CRISPR-Cas nucleases, *Nat. Biotechnol.* 33:187-197 (2015).
Volkov et al., Selective protection of nuclease-sensitive sites in siRNA prolongs silencing effect, *Oligonucleotides*. 19:191-202 (2009).
Wang et al., Rapid and efficient assembly of transcription activator-like effector genes by USER cloning, *J. Genet. Genomics*. 41:339-47 (2014).
Weber et al., A modular cloning system for standardized assembly of multigene constructs, *PLoS One*. 6:e16765 (2011).
Whitehead et al., Silencing or stimulation? siRNA delivery and the immune system, *Annual Review of Chemical and Biomolecular Engineering*. 2:77-96 (2011).
Winkler, Oligonucleotide conjugates for therapeutic applications, *Ther. Deliv.* 4:791-809 (2013).
Wolfs et al., MegaTevs: single-chain dual nucleases for efficient gene disruption, *Nucliec Acids Res*. 42:8816-29 (2014).
Zetsche et al., Cpf1 is a single RNA guided endonuclease of a class 2 CRISPR-Cas system, *Cell*. 163:759-71 (2015).
Zhou et al., Pressure Overload by Transverse Aortic Constriction Induces Maladaptive Hypertrophy in a Titin-Truncated Mouse Model, *Biomed. Res. Int.* 2015:163564 (2015).
Zou et al., An internal promoter underlies the difference in disease severity between N- and C-terminal truncation mutations of Titin in zebrafish, *Elife*. 4:e09406 (2015).
Shih et al., Finding the Achilles' heel of muscle Giant-TALEN-mediated Gene-editing in Zebrafish titin. *Circulation Research; Basic Cardiovascular Sciences of the American-Heart-Associated*, 114:344 (Abstract Only) (2015).
NCBI Accession No. XM_024453100.1, PREDICTED: *Homo sapiens* titin (TTN), transcript variant X12, mRNA, dated Mar. 1, 2020.
NCBI Accession No. NG_051363.1, *Homo sapiens* TTN antisense RNA 1 (TTN-AS1), RefSeqGene on chromosome 2, dated Feb. 17, 2020.
GenBank Accession No. BE676391, 7f28h04.x1 NCI_CGAP_CLL1 *Homo sapiens* cDNA clone IMAGE:3296023 3' similar to TR:Q10465 Q10465 Titin, Skeletal Muscle Isoform, mRNA sequence (XP055708767), dated Sep. 13, 2000, last updated Jan. 27, 2011.
NCBI Accession No. XM_012650762.1, PREDICTED:Propithecus coquereli titin (TTN), mRNA, dated Jun. 1, 2015.
GenBank Accession No. AJ277892.2, *Homosapiens* partial TTN gene for titin, Nov. 14, 2006.
Gramlich et al., "Antisense-mediated exon skipping: a therapeutic strategy for titin-based dilated cardiomyopathy," *EMBO Molecular Medicine*, 7(5): 562-76 (2015).
Gutschner et al., "Genome engineering—Matching supply with demand," *Cell Cycle*, 15(11): 1395-96 (2016).

\* cited by examiner

Repair Strategy 1: Repair titin mutation c.32854G>C using donor template

| Human specific SaCas9 | | | | | |
|---|---|---|---|---|---|
| Position | Strand | Spacer Sequence | PAM | Specificity Score | OLIGOS ORDERED |
| Guide 1: chr2 +178,645,987 * | -1 | GGAGGAGGTGGGGGTCTTGGT (SEQ ID NO: 1) | TTGAGT (SEQ ID NO: 2) | 55 | CACCGGAGGAGGTGGGGGTCTTGGT (SEQ ID NO: 3) |
|  | reverse |  |  |  | AAACACCAAGACCCCCACCTCCTCC (SEQ ID NO: 4) |
| Guide 2: chr2 +178,645,975 | -1 | GGTGGAGCAGGTGGAGGAGGT (SEQ ID NO: 5) | GGGGGT (SEQ ID NO: 6) | 25 | CACCGGTGGAGCAGGTGGAGGAGGT (SEQ ID NO: 7) |
|  | reverse |  |  |  | AAACACCTCCTCCACCTGCTCCACC (SEQ ID NO: 8) |
| Guide 3: chr2 +178,645,924 | -1 | TGGCATTTTTACCTTTAAGT (SEQ ID NO: 9) | TGGAAT (SEQ ID NO: 10) | 14 | CACCTGGCATTTTTACCTTTAAGT (SEQ ID NO: 11) |
|  | reverse |  |  |  | ACCGTAAAAAATGGAAATTCACAAA (SEQ ID NO: 12) |
| Guide 4: chr2 +178,646,032 * | -1 | TTTTCAGGTTCAGGTTCTTGA (SEQ ID NO: 13) | AAGAGT (SEQ ID NO: 14) | 36 | CACCTTTTCAGGTTCAGGTTCTTGA (SEQ ID NO: 15) |
|  | reverse |  |  |  | AAAAGTCCAAGTCCAAGAACTCAAA (SEQ ID NO: 16) |

\* Best performing guide sequences; Underlined letter of the spacer sequence corresponds to the location of double-stranded break made in the target sequence Oligos ordered corresponds to primer sequences used for cloning the spacer sequence into the Cas9 plasmid (px601 Addgene plasmid #61591)

Figure 2

SEQ ID NO: 17

Human donor template sequence (for repair of c.32854G>C mutation) with 450 nt homology arms on either side of repair region:

ctttacatataccaaatacaacaacatgtatacatcatacagacaagggtaaacatacatttcataagaaacaacatttacactcggagtaagaatccaaaggtacattgaacatgacaaagagagtacagttga caccgaacagacctacgaaacactacgacacaacaacaataacacgaaacgacataaagagtagagaaacattcccactataaaatacaagacacaaatacaacctatgacacataatgcatgga attttcatttgaaacatgaagtatatatataatatatatatataaagataattatatgtatgtatatatgtatgattgtatatggtatatgattgtggagactttatgagaaagttcTT GGACTTGGACTTTCCAATAACTTCGGTTTTGAGTTTGGTTCTGGGGGTGGAGGAGGTGGACGAGGTGGATTCCTTACACTTCCTCTTTTATAAGGTTGA ATTTCcatttttacggtgaaggtttcaaaataatcgacgaagtttgaagataggtcgtagacttttactacgaacgttctttacatactgaaaatcttcacacatgaaagtctgtactaacatgacacactctaacgt atctgacagagaagacgacggggtaccaaggaccaagaacaacagtacggacgacgacgacgttttcagtctttcatgtaactatcgcagtaggccctatagacttacgtccgtgacaggttaattgaaagaa aacacctcacccctcttcaaagactaagttcgactaacgatatgtatagtaacgctagaatacgaattcctacatattcttaggaacgttctataaaattataac

SEQ ID NO: 18

(lower case denotes intronic sequences; upper case denotes exonic sequence; underline bold letter denotes exact repair of mutation)

Figure 4

Repair Strategy 2: Remove exon containing mutation c.32854G>C using CRISPR/Cas9 to restore reading frame

| Human specific SaCas9 | | | | | |
|---|---|---|---|---|---|
| Position | Location | Spacer Sequence | PAM | Specificity Score | OLIGOS ORDERED |
| Chr 2: 178,646,056 | Intron 218 | AGTATATGTATATGTTAGCAT (SEQ ID NO: 19) | GTGGAT (SEQ ID NO: 20) | 79 | CACCAGTATATGTATATGTTAGCAT (SEQ ID NO 21) |
| | -1 | | | | |
| | reverse | | | | TCATATACATATACAATCGTACAAA (SEQ ID NO: 22) |
| chr2 +178,645,863 | Intron 219 | TGCAAGCATCATTTCAGATGG (SEQ ID NO: 23) | CTGGAT (SEQ ID NO: 24) | 61 | CACCTGCAAGCATCATTTCAGATGG (SEQ ID NO: 25) |
| | -1 | | | | |
| | reverse | | | | ACGTTCGTAGTAAAGTCTACCCAAA (SEQ ID NO: 26) |

Underlined letter of the spacer sequence corresponds to the location of double-stranded break made in the target sequence Oligos ordered corresponds to primer sequences used for cloning the spacer sequence into the Cas9 plasmid (px601 Addgene plasmid #61591)

Figure 6

Deletion of exon 219

| Position | Strand | Spacer Sequence | SEQ ID NO | PAM | SEQ ID NO | Specificity Score |
|---|---|---|---|---|---|---|
| Chr 2:178646456 | -1 | AGAAGATTAAGTCCACTGGA | 27 | TTGAAT | 42 | 44.6132083 |
| Chr 2:178646451 | -1 | GATAAAGAAGATTAAGTCCA | 28 | CTGGAT | 43 | 39.3753798 |
| Chr 2:178646346 | -1 | ATGAGGCTCACATTACAACA | 29 | AAGAAT | 44 | 43.2076588 |
| Chr 2:178645704 | 1 | TGATAGCGTCATCCGGGATAT | 30 | CTGAAT | 45 | 49.4369454 |
| Chr 2:178646321 | -1 | GTACAAGTTACATGGAAACCT | 31 | AAGAAT | 46 | 43.4406842 |
| Chr 2:178646213 | 1 | TTTATGTTCTGTGTTTATG | 32 | TTGGAT | 47 | 42.9694116 |
| Chr 2:178645669 | 1 | TGTCCAATTAACTTCTTTG | 33 | TGGAGT | 48 | 36.6155577 |
| Chr 2:178645656 | 1 | TTCTTTTGTGGAGTGGGAGA | 34 | AAGAGT | 49 | 28.0044261 |
| Chr 2:178645712 | 1 | AAGTACATTGATAGCGTCATC | 35 | CGGGAT | 50 | 48.8316012 |
| Chr 2:178645776 | 1 | TCTTCTGCTGCCCATGGTC | 36 | CTGGGT | 51 | 42.8850669 |
| Chr 2:178645598 | 1 | ATCATTGCGATCTTATGCTTA | 37 | AGGAAT | 52 | 46.915383 |
| Chr 2:178646253 | 1 | GTATTTCTCATCATCTTTGTA | 38 | AAGGGT | 53 | 36.4064834 |
| Chr 2:178645688 | -1 | CAGTGCCTGCATTCAGATATC | 39 | CCGGAT | 54 | 44.6971424 |
| Chr 2:178646313 | 1 | CTCATGTCAACTGTGGCTTGT | 40 | CTGGAT | 55 | 43.7754718 |
| Chr2:178,646,422 | -1 | AACCATATACATTTCAAGAGA | 41 | AAGAAT | 56 | 37.7929693 |

Underlined letter of the spacer sequence corresponds to the location of double-stranded break made in the target sequence

Figure 7

Repair Strategy 3: Cut out and repair Titin mutation c.37112 G>A

| Position | Strand | Spacer Sequence | PAM | Specificity Score |
|---|---|---|---|---|
| Chr 2: 178622784 | -1 | GGAGCTGTAAGAGAATGTCAT (SEQ ID NO: 57) | CAGAAT (SEQ ID NO: 58) | 41.758739 |
| Chr 2: 178622773 | -1 | ATTCCACATGAGGAGCTGTAA (SEQ ID NO: 59) | GAGAAT (SEQ ID NO: 60) | 44.4639886 |
| Chr 2: 178622779 | 1 | ATTCTCTTACAGCTCCTCATG (SEQ ID NO: 61) | TGGAAT (SEQ ID NO: 62) | 42.8443275 |

Underlined letter of the spacer sequence corresponds to the location of double-stranded break made in the target sequence

Donor Template:
ccatagtgcttcacgttcctatctttgaattctgctaattctcaaagatgttgctaagtgccttaaataagacaatgtttcttttgcactgtgtctgaagttcttgacatattctttcaagttgtggtgcagtgcaaatgaagattttttcctccagctattattccaaagaactgagatgctccctagtatatactgagtcatgtacacacatgcacactagttgaacatagaatgccacataattttgtaactaaagagatatctaaaaagcaaagcatcatacctgatgggcagcttcaaagtcagttgtagtcattgtcaaagatcagttagtgagttgtgtcattaagagatggaaatcccaaaaagagtcacttttcttaatgtatactatgtaatgtcagagtaaattccagaaacctcattttgaattctgatgacattcttacaGctcctcatgtggaattcttaagaccactcaccgaccttcaagttagagaaaaagaaatggctcgatttgagtgtgaactttCCCGAGAAAATGCTAAGgtctgtgactgtataccgtcatcttgtactgtcaaataacttatatttactttggtctagccaaaatggcaaaatggaaaaaaagttagtcacaacttctctggtcaccacttttactttt
aaagataattgtagtataaatgtattcttgactttaattgctctcttttagtattattcttgaaaaacactgactcacaatcaggagatttagatattagtttgaaccatagaaagtgctgtttc
ttagatcagaaagtcaaatatcagcaattatctttcaactaagtacctcctgttgctattaactaccattggcaagttcttcaagtc

SEQ ID NO: 63

*lowercase denotes intronic sequences; uppercase denotes exonic sequences; Underlined bold denotes the repair

Figure 8

Repair Strategy 4: Exon Skipping of Exon 326 – Repair of 2 bp insertion in exon 326 (c.4362insAT, p.Ser14450fsX4) which causes a frameshift with premature stop codon in the A band truncating more than half the A band and the entire M band (accounts for ~20% of known DCM causing TTN mutations)

Set 1

| Position | Strand | Spacer Sequence | PAM | Specificity Score |
|---|---|---|---|---|
| Chr 2: 178576493 | -1 | TTAGATAAAATATTGGCAC<u>C</u>TC (SEQ ID NO: 64) | TGGAAT (SEQ ID NO: 65) | 43.073943 |
| Chr 2: 178576463 | -1 | TATATATTCAGAGTTTGGC<u>T</u>T (SEQ ID NO: 66) | TTGGGT (SEQ ID NO: 67) | 38.9577076 |
| Chr 2: 178576474 | 1 | AAATTACCCAAAAGCCAAA<u>A</u>CT (SEQ ID NO: 68) | CTGAAT (SEQ ID NO: 69) | 40.3960258 |
| Chr 2: 178576450 | -1 | AAAGACACAAAAGTATAT<u>A</u>TT (SEQ ID NO: 70) | CAGAGT (SEQ ID NO: 71) | 28.3422717 |

Set 2

| Position | Strand | Sequence | PAM | Specificity Score |
|---|---|---|---|---|
| Chr 2: 178559283 | -1 | AGCAAAATTAACGTGGATATG (SEQ ID NO: 72) | TAGAAT SEQ ID NO: 73) | 36.7538162 |
| Chr 2: 178559284 | 1 | ACATATCCACGTTAATTT<u>T</u>GC (SEQ ID NO: 74) | TAGAAT (SEQ ID NO: 75) | 45.3645981 |
| Chr 2: 178559275 | 1 | CGTTAATTTTGCTAGAATA<u>A</u>GT (SEQ ID NO: 76) | GTGAGT (SEQ ID NO: 77) | 39.5941154 |

Underlined letter of the spacer sequence corresponds to the location of double-stranded break made in the target sequence

Figure 9

REPAIRING A MUTANT HUMAN TITIN GENE USING CRISPR TECHNOLOGY

This application claims priority to U.S. Provisional Patent Application No. 62/255,887, filed on Nov. 16, 2015, which is incorporated by reference herein in its entirety.

FIELD

The present application provides materials and methods for treating a patient with a titin-based myopathy, particularly a titin-based cardiomyopathy, and/or other titinopathies. In addition, the present application provides materials and methods for editing the titin gene in a cell by genome editing.

BACKGROUND

The protein titin, formerly named "connectin," is the largest protein in the human body. It functions as the molecular spring of skeletal muscle. The human titin gene is located on chromosome 2q31. The coding region of the titin gene includes 364 exons, 363 of which encode 38,138 amino acid residues (4,200 kD) (GenBank accession number AJ277892). The size of the skeletal-muscle titin protein is 3,700 kD, and its physical length in vivo is 2 μm. Titin has mechanical, developmental, and regulatory roles in striated muscles. Its four regions (the Z-disk, I-band, A-band and M-line) stretch over the length of one-half of the basic building block of muscles, the sarcomere. See FIG. 1, panel A [reproduced from Cheveau et al., Human Mutation, 35(9): 1046-1059 (2014)]. One of the main functions of titin is to keep the contractile elements of the sarcomere in place, and it is responsible for muscle elasticity.

Titin has several sites for alternative splicing, causing isoforms of different lengths to appear in different muscles [Bang et al., Circ Res 89:1065-1072 (2001)]. I-band isoforms have been observed to be longer in skeletal (3,700 kD) than in cardiac (2,970-3,300 kD) muscle, whereas, in the Z disk, cardiac-muscle titins contain more repeat motifs than do skeletal-muscle titins (Gautel et al. J Cell Sci 109:2747-2754 1996; Sorimachi et al. J Mol Biol 270:688-695 1997). A C-terminally truncated 700-kD isoform of titin is expressed in cardiac muscle (Bang et al., supra). The M-line region of titin is also differentially expressed, and two different splice isoforms have been identified: Mex5+ and Mex5– (Labeit and Kolmerer Science 270:293-296 1995; Kolmerer et al. J Mol Biol 256:556-563 1996; Sorimachi et al., supra). On the ultrastructural level, both the carboxy-terminal Mex6 titin epitope and the catalytic titin kinase domain have been localized within the periphery of the M-line lattice (Obermann et al. EMBO J 16:211-220 1997). The Mex5/Mex6 titin epitopes, the catalytic titin kinase domain, and the p94 and muscle-specific ring finger-1 (MURF-1) proteins that are bound to this region of titin may form a signaling complex (Sorimachi et al., supra; Centner et al. J Mol Biol 306:717-726 2001). The occurrence of several different titin isoforms may be relevant for the selective involvement of muscles in anatomically restricted myopathies (Sorimachi et al. supra). Recently, autosomal dominant dilated cardiomyopathy was shown to be associated with A-band titin mutations in exon 326, which cause a frameshift, and with a mutation in the Z-disk titn [Siu et al. Circulation 99:1022-1026 (1999); Gerull et al., Nat Genet 30:201-204 (2002)].

Titin provides ligand binding sites for a large number of other muscle proteins. See FIG. 1, panel B [reproduced from Cheveau et al., supra].

The alternative splicing of the titin gene in different cells results in altered isoform composition and variation in the passive stiffness of the protein, in turn affecting the functionality and stability of muscle. Specifically in cardiac muscle, fetal cardiac titin has a very long spring segment; the adult N2B isoform has a shorter and stiffer spring; the adult N2BA isoform has an intermediate and more compliant spring and the N2A skeletal muscle specific isoform has a long spring length [LeWinter, *Circulation*. Jul. 13 2004; 110(2):109-111]. In the normal heart, titin is the main determinant of passive myocardial stiffness at physiological sarcomere lengths [Granzier et al., *Proceedings of the National Academy of Sciences of the United States of America*. Oct. 7 2014; 111(40):14589-14594].

Decreasing amounts of the N2BA isoform in heart muscle are characteristic of those with end stage heart failure [McNally et al., *Cell metabolism*. Feb. 3 2015; 21(2):174-182] and with non-ischemic dilated cardiomyopathy (DCM) [LeWinter and Granzier, *Journal of cardiovascular pharmacology*. March 2014; 63(3):207-212; Makarenko et al., *Circulation research*. Oct. 1, 2004; 95(7):708-716; Jaber et al. *Circulation. Heart failure*. September 2008; 1(3):192-199]. Sarcomeric passive tension is reduced by approximately 30% in DCM adult patients and this loss of tension results from loss of titin and increased fibrosis [Makarenko et al, supra]. Recently, 5,200 patients underwent sequencing of titin to identify pathogenic mutations leading to DCM [Roberts et al., *Science translational medicine*. Jan. 14, 2015; 7(270):270ra276] and it was identified that 30% of familial DCM cases are due to titin-based mutations, specifically C-terminus truncating mutations [Herman et al., *The New England Journal of Medicine*. 2012; 366(7):619-628; Gerull et al., supra; Itoh-Satoh et al., *Biochemical and Biophysical Research Communications*. 2002; 291(2):385-393; Gerull et al., *Journal of Molecular Medicine*. 2006; 84(6):478-483]. Non-ischemic DCM occurs in 1 of 250 people and it is an important cause of heart arrhythmias, heart failure and heart transplants.

Since there has previously been no cure or treatment for titin-based myopathies or other titinopathies, there exists a need in the art to provide products and methods for treating titin-based myopathies and/or other titinopathies.

SUMMARY

Provided herein are ex vivo and in vivo methods for creating permanent changes in the genome by correcting one or more mutations in the titin gene by genome editing and restoring titin protein activity, which can be used to treat titin-based cardiomyopathies and other titinopathies, as well as components, kits and compositions for performing such methods, and cells produced by them.

In one aspect, provided herein are methods for editing the titin gene in a human cell by genome editing comprising introducing into the cell one or more deoxyribonucleic acid (DNA) endonucleases to effect one or more double-strand breaks (DSBs) within the titin gene that results in permanent correction of one or more mutations within the titin gene and restoration of titin protein activity.

In some embodiments, methods provided herein are ex vivo methods for treating a patient with a titin-based cardiomyopathy or other titinopathy comprising the steps of: performing a biopsy of the patient's heart; isolating a cardiac progenitor cell, including but not limited to an endogenous cardiac stem cell (eCSC) or primary cardiomyocyte; editing the titin gene of the eCSC or primary cardiomyocyte; and implanting the eCSC or primary cardiomyocyte into the patient.

In some embodiments, the step of isolating an eCSC or primary cardiomyocyte comprises: perfusion of fresh heart tissues with digestion enzymes, cell differential centrifugation and cell culturing.

In some embodiments, the step of editing the titin gene of the eCSC or primary cardiomyocyte comprises introducing into the progenitor cell or primary cardiomyocyte one or more deoxyribonucleic acid (DNA) endonucleases to effect one or more double-strand breaks (DSBs) within the titin gene that results in permanent correction of one or more mutations within the titin gene and restoration of titin protein activity.

In some embodiments, the step of implanting the eCSC or primary cardiomyocyte into the patient comprises implanting the eCSC or primary cardiomyocyte into the patient by local injection or systemic infusion.

In some embodiments, provided herein is an in vivo method for treating a patient with a titin-based cardiomyopathy and/or other titinopathy comprising the step of editing the titin gene in a cell of the patient.

In some embodiments, the step of editing the titin gene in a cell of the patient in vivo comprises introducing into the cell one or more deoxyribonucleic acid (DNA) endonucleases to effect one or more double-strand breaks (DSBs) within the titin gene that results in permanent correction of one or more mutations within the titin gene and restoration of titin protein activity.

In some embodiments, the one or more DNA endonucleases is a Cas1, Cas1 B, Cas2, Cas3, Cas4, Cas5, Cas6, Cas7, Cas8, Cas9 (also known as Csn1 and Csx12), Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or Cpf1 endonuclease; or a species homolog, codon-optimized, or modified version thereof.

In some embodiments, the DNA endonuclease is a Cas9 endonuclease. In some embodiments, the Cas9 endonuclease is an *S. aureus* Cas9 endonuclease. In some embodiments, the Cas9 endonuclease comprises an amino acid sequence at least 50% identical to the *S. aureus* Cas9 endonuclease and retains at least 90%, 95% or 98% identity over the HNH domain and at least 90%, 95% or 98% identity to the RuvC domain. In some embodiments, the DNA endonuclease is a Cpf1 endonuclease. In some embodiments, the Cpf1 endonuclease is an *Acidaminococcus* sp. BV3L6 Cpf1 endonuclease. In some embodiments the Cpf1 endonuclease is *Lachnospiraceae bacterium* ND2006 Cpf1 endonuclease. In some embodiments, the Cpf1 endonuclease comprises an amino acid sequence at least 50% identical to the *Acidaminococcus* sp. BV3L6 or *Lachnospiraceae bacterium* ND2006 endonuclease and retains at least 90%, 95% or 98% identity to the RuvC domain.

In some embodiments, the method comprises introducing into the cell one or more polynucleotides encoding the DNA endonuclease. In some embodiments, the method comprises introducing into the cell one or more ribonucleic acids (RNAs) encoding the DNA endonuclease. In some embodiments, the one or more polynucleotides or one or more RNAs, is a modified polynucleotide or RNA, optionally including modified backbones, sugar moieties, internucleoside linkages, and modified or universal bases.

In some embodiments, the method further comprises introducing into the cell one or more guide ribonucleic acids (gRNAs). In some embodiments, the one or more gRNAs are single-molecule guide RNA (sgRNAs). In some embodiments, the one or more gRNAs, or one or more sgRNAs, is a modified RNA, optionally including modified backbones, sugar moieties, internucleoside linkages, and modified or universal bases.

In some embodiments, the one or more DNA endonucleases is pre-complexed with one or more gRNAs or sgRNAs.

In some embodiments, the method further comprises introducing into the cell a polynucleotide donor template comprising a part of the wild-type titin gene or cDNA.

In some embodiments, the method further comprises introducing into the cell one guide ribonucleic acid (gRNA) and a polynucleotide donor template comprising a part of the wild-type titin gene, and wherein the one or more DNA endonucleases is one or more Cas9 endonucleases that effect one double-strand break (DSB) at a DSB locus within the titin gene that facilitates insertion of a new sequence from the polynucleotide donor template into the chromosomal DNA at the DSB locus that results in permanent correction of a part of the chromosomal DNA of the titin gene proximal to the DSB locus and restoration of titin protein activity, and wherein the gRNA comprises a spacer sequence that is complementary to a segment of the DSB locus. In some embodiments, proximal means nucleotides both upstream and downstream of the DSB locus.

In some embodiments, the method further comprises introducing into the cell two guide ribonucleic acid (gRNAs) and a polynucleotide donor template comprising a part of the wild-type titin gene, and wherein the one or more DNA endonucleases is two or more Cas9 endonucleases that effect a pair of double-strand breaks (DSBs), the first at a 5' DSB locus and the second at a 3' DSB locus, within the titin gene that facilitates insertion of a new sequence from the polynucleotide donor template into the chromosomal DNA between the 5' DSB locus and the 3' DSB locus that results in permanent correction of the chromosomal DNA between the 5' DSB locus and the 3' DSB locus within the titin gene and restoration of titin protein activity, and wherein the first guide RNA comprises a spacer sequence that is complementary to a segment of the 5' DSB locus and the second guide RNA comprises a spacer sequence that is complementary to a segment of the 3' DSB locus.

In some embodiments, the one or two gRNAs are single-molecule guide RNA (sgRNAs). In some embodiments, the one or two gRNAs or one or two sgRNAs is a modified gRNA or modified sgRNA, optionally including modified backbones, sugar moieties, internucleoside linkages, and modified or universal bases.

In some embodiments, the one or more DNA endonucleases is pre-complexed with one or two gRNAs or sgRNAs.

In some embodiments, the DSB is in titin exon 219, titin exon 242 or titin exon; or a 5' DSB and a 3' DSB are respectively in intron 218 and intron 219, or are respectively in the intron 325 and intron 327, of the titin gene.

In some embodiments, the gRNA or sgRNA is directed to one or more of the following pathological variants c.32854G>C, c.37112G>A and c4362insAT.

In some embodiments, the correction is by homology directed repair (HDR).

In some embodiments, the Cas9 mRNA, gRNA, and donor template are either each formulated separately into lipid nanoparticles or all co-formulated into a lipid nanoparticle. In some embodiments, delivery is by local injection or systemic infusion.

In some embodiments, the Cas9 mRNA is formulated into a lipid nanoparticle, and both the gRNA and donor template are delivered by an adeno-associated virus (AAV). In some embodiments, delivery is by local injection or systemic infusion.

In some embodiments, the titin gene is located on Chromosome 2q31 (Genome Reference Consortium—GRCh38/hg38).

In another aspect, provided herein are one or more guide ribonucleic acids (gRNAs) comprising a spacer sequence selected from the group consisting of the spacer sequences in the Figures for editing the titin gene in a cell from a patient with a titin-based cardiomyopathy or titinopathy. In some embodiments, the one or more gRNAs are single-molecule guide RNAs (sgRNAs). In some embodiments, the one or more gRNAs or sgRNAs is a modified gRNA or modified sgRNA, optionally including modified backbones, sugar moieties, internucleoside linkages, and modified or universal bases.

In another aspect, provided herein are cells that have been modified by the preceding methods to permanently correct one or more mutations within the titin gene and restore titin protein activity. Further provided herein are methods for ameliorating titin-based cardiomyopathies and/or titinopathies by the administration of cells, the genomes of which have been modified by the preceding methods, to a patient.

Various other aspects and embodiments are described and exemplified herein.

BRIEF DESCRIPTION OF THE DRAWINGS

FIG. 1A shows titin has four regions (the Z-disk, I-band, A-band and M-line) that stretch over the length of one-half of the basic building block of muscles, the sarcomere. FIG. 1B shows that titin provides ligand binding sites for a large number of other muscle proteins over the various regions.

FIG. 2 shows the PAMs chosen and the 21 bp spacer sequence (of each gRNA) that is complementary to the titin DNA target sequence selected. The position number given in FIG. 2 corresponds to the 3' end of the guide sequence that is complementary to the titin genomic sequence. The specificity score was determined using the software available on DeskGen.com. The higher the specificity score, the more specific the gRNA is predicted to be to the titin genome.

FIG. 4 shows the donor template was a single-stranded oligonucleotide 100 nucleotides (nt) in length, which included homology arms and spanned the 21 nt target sequence but also includes a mutated PAM sequence to decrease the probability of Cas9 cutting the donor template.

FIG. 6 shows the PAMs chosen and the 21 bp spacer sequence (of each gRNA) that is complementary to the respective intron DNA target sequence selected for repair strategy 2.

FIG. 7 shows 21 bp spacer sequences that could alternatively be used in one or both members of a pair of sgRNAs to delete exon 219.

FIG. 8 shows the PAMs chosen and the 21 bp spacer sequence (of each gRNA) that is complementary to the titin DNA target sequence selected for repair strategy 3.

FIG. 9 shows two sets of the PAMs selected (one set for each intron) and the 21 bp spacer sequence (of each gRNA) that is complementary to the respective intron DNA target sequence selected for repair strategy 4.

DETAILED DESCRIPTION

Titinopathies

Figure 1A:
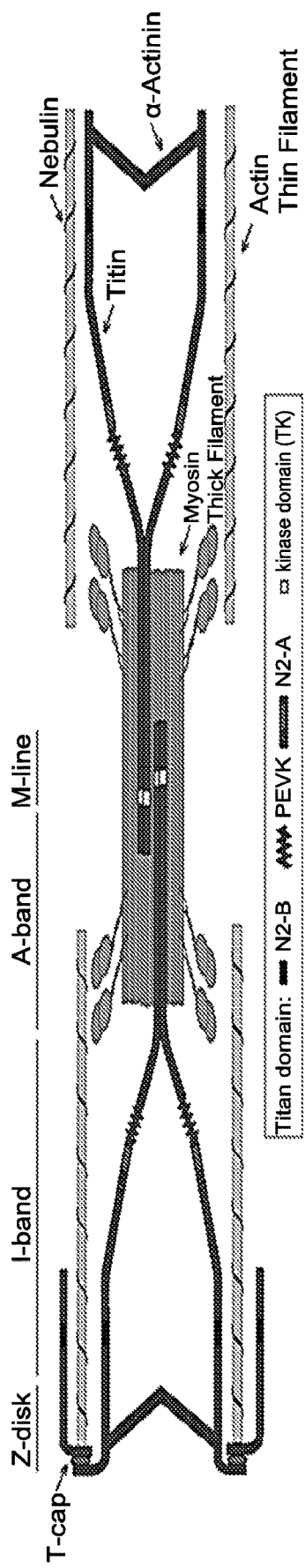
FIGS. 1A-B provides information reproduced from Cheveau et al. (Human Mutation, 35(9): 1046-1059 (2014)).

A titinopathy is a condition involving a homozygous or compound heterozygous mutation that inactivates both copies of the titin gene.

There are various mutations associated with titinopathies, which are a combination of missense, nonsense, frameshift and other mutations. The various mutations are distributed across the exons of the gene. Prevalent mutations include, but are not limited to, c.32854G>C, c.37112G>A, c4362insAT, c.43628insAT, p.EE3359 W33362delinsVKEK (US Patent Publication No. 20130171172 A1), c.62890delG, mutations located in exons 112-225 which are located in the PEVK region of titin, mutations in exon 48 (Novek 3 isoform), and mutations in the cardiac N2B isoform.

A titin-based myopathy is a titinopathy in which the mutation(s) in the titin gene result in muscle impairment. Muscle impairment includes, but is not limited to, at least one of abnormal muscle fatigue, muscle weakness, muscle deterioration and/or muscle fibrosis. In some embodiments, the titin-based myopathy is a titin-based cardiomyopathy.

Titin-based myopathies include, but are not limited to, Centronuclear Myopathies, Limb Girdle Muscular Dystrophy 2J, Dilated Cardiomyopathies, Hereditary Myopathy with Early Respiratory Failure, Early-Onset Myopathy with Fatal Cardiomyopathy, Hypertrophic Cardiomyopathy, and Tibial Muscular Dystrophy Therapeutic Approaches Provided herein are ex vivo and in vivo methods for using genome engineering tools to create permanent changes to the genome by correcting one or more mutations in the titin gene and restoring titin protein activity. Such methods use endonucleases, such as CRISPR/Cas9 nucleases, to permanently restore natural splicing or a natural coding region in the genomic locus of the titin gene.

Provided herein are methods for treating a patient with a titin-based cardiomyopathy or a titinopathy. An embodiment of such method is an ex vivo cell based therapy.

In some embodiments of ex vivo cell based therapy, a biopsy of the patient's heart is performed. Then, an eCSC or primary cardiomyocyte is isolated from the biopsied material. Next, the chromosomal DNA of the eCSC or primary cardiomyocyte is corrected using the materials and methods described herein. Finally, the genome edited eCSC or primary cardiomyocyte is implanted into the patient.

Another embodiment of such a method is an in vivo based therapy. In this method, the chromosomal DNA of a cell in the patient is corrected using the materials and methods described herein.

The advantage of in vivo gene therapy is the ease of therapeutic production and administration. The same therapeutic approach and therapy will have the potential to be used to treat more than one patient, for example a number of patients who share the same or similar genotype or allele. In contrast, ex vivo cell therapy typically requires using a patient's own cells, which are isolated, manipulated and returned to the same patient.

The methods of the invention, regardless of whether an ex vivo or in vivo method, involve either: correcting one or more specific mutations in the gene, or introducing exogenous titin cDNA sequence or a fragment thereof into the locus of the gene or at a heterologous location in the genome (such as a safe harbor site, such as AAVS1). Both the correction and knock-in strategies utilize a donor DNA template in Homology-Directed Repair (HDR). HDR in either strategy may be accomplished by making one or more double-stranded breaks (DSBs) at specific sites in the genome by using one or more endonucleases.

For example, the correction strategy involves correcting a specific mutation in the gene by inducing one double stranded break in the gene of interest with Cas9 and a sg RNA, or two or more double stranded breaks in the gene of interest using two or more appropriate sgRNAs, in the presence of a donor DNA template introduced exogenously to direct the cellular DSB response to Homology-Directed Repair (the donor DNA template can be a short single stranded oligonucleotide, a short double stranded oligonucleotide, a long single or double stranded DNA molecule). This approach requires development and optimization of gRNAS and donor DNA molecules for all major variants of the titin gene.

For example, the knock-in strategy involves knocking-in wild-type titin cDNA into the locus of the gene using a sgRNA or a pair of sgRNAs targeting upstream of, or in an exon and/or intron, of the titin gene, or in a safe harbor site (such as AAVS1). The donor DNA will be single or double stranded DNA having homologous arms to the insertion region.

The advantages for both strategies (correction and knock-in) are similar, including in principle both short and long term beneficial clinical and laboratory effects. In addition, it may be that only a low percentage of titin activity is required to provide therapeutic benefit. Another advantage for both strategies is that most patients have low-level gene and protein activity, therefore suggesting that additional protein expression, for example following gene correction, should not necessarily lead to an immune response against the target gene product. The knock-in approach does provide one advantage over the correction approach—the ability to treat all patients versus only a subset of patients. While there are common mutations in this gene, there are also many other possible mutations, and using the knock-in method could treat all of them.

Alternatively, a knock-out strategy involves knocking-out an exon or exons of the titin gene that harbour a mutation in order to cause a frameshift to correct the reading frame and rescue the titin protein. This strategy utilizes a gRNA or a pair of gRNAs to excise an exon (or "skip" the exon) with a mutation. In this strategy, no donor DNA template is utilized.

Human Cells

For ameliorating titin-based cardiomyopathies and/or titinopathies, as described and illustrated herein, the principal targets for genome editing are human cells.

By performing genome editing in autologous cells that are derived from and therefore already completely matched with the patient in need, it is possible to generate cells that can be safely re-introduced into the patient, and effectively give rise to a population of cells that will be effective in ameliorating one or more clinical conditions associated with the patient's disease.

In some embodiments, the genome edited human cells are skeletal muscle progenitor cells. In some embodiments, the genome edited human cells are skeletal muscle cells.

In some embodiments, the genome edited human cells are endogenous cardiac stem cells (eCSCs) [identification: Torella et al., Cellular Molecular Life Science. 2007, 64:661-673 and Bearzi et al., Proc Natl Acad Sci USA. 2007; 104: 14068-14073; types of progenitor cells including eCSCs: Sanganalmath and Bolli, Circulation Research. 2013; 113: 810-834; isolating eCSCs from cardiac biopsies: D'Amario et al, Circ Res. 2011; 108:857-861]. In some embodiments, the genome edited human cells are primary cardiomyocytes. In some embodiments, the genome edited human cells are cardiomyocytes.

Performing a Biopsy

A biopsy is a sample of tissue taken from the body. A biopsy may be performed according to any of the known methods in the art. For example, a needle is inserted into the heart to capture heart cells.

Isolating a eCSC or Primary Cardiomyocyte eCSCs and primary cardiomyocytes may be isolated according to any method known in the art.

Genome Editing

Genome editing generally refers to the process of modifying the nucleotide sequence of a genome, preferably in a precise or pre-determined manner. Examples of methods of genome editing described herein include methods of using site-directed nucleases to cut deoxyribonucleic acid (DNA) at precise target locations in the genome, thereby creating double-strand or single-strand DNA breaks at particular locations within the genome. Such breaks can be and regularly are repaired by natural, endogenous cellular processes, such as homology-directed repair (HDR) and non-homologous end-joining (NHEJ), as recently reviewed in Cox et al., Nature Medicine 21(2), 121-31 (2015). NHEJ directly joins the DNA ends resulting from a double-strand break, sometimes with the loss or addition of nucleotide sequence, which may disrupt or enhance gene expression. HDR utilizes a homologous sequence, or donor sequence, as a template for inserting a defined DNA sequence at the break point. The homologous sequence may be in the endogenous genome, such as a sister chromatid. Alternatively, the donor may be an exogenous nucleic acid, such as a plasmid, a single-strand oligonucleotide, a double-stranded oligonucleotide, a duplex oligonucleotide or a virus, that has regions of high homology with the nuclease-cleaved locus, but which may also contain additional sequence or sequence changes including deletions that can be incorporated into the cleaved target locus. A third repair mechanism is microhomology-mediated end joining (MMEJ), also referred to as "Alternative NHEJ", in which the genetic outcome is similar to NHEJ in that small deletions and insertions can occur at the cleavage site. MMEJ makes use of homologous sequences of a few basepairs flanking the DNA break site to drive a more favored DNA end joining repair outcome, and recent reports have further elucidated the molecular mechanism of this process; see, e.g., Cho and Greenberg, Nature 518, 174-76 (2015); Kent et al., Nature Structural and Molecular Biology, Adv. Online doi:10.1038/nsmb.2961(2015); Mateos-Gomez et al., Nature 518, 254-57 (2015); Ceccaldi et al., Nature 528, 258-62 (2015). In some instances it may be possible to predict likely repair outcomes based on analysis of potential microhomologies at the site of the DNA break.

Each of these genome editing mechanisms can be used to create desired genomic alterations. A step in the genome editing process is to create one or two DNA breaks, the latter as double-strand breaks or as two single-stranded breaks, in the target locus as close as possible to the site of intended mutation. This can be achieved via the use of site-directed polypeptides, as described and illustrated herein.

Site-directed polypeptides, such as a DNA endonuclease, can introduce double-strand breaks or single-strand breaks in nucleic acids, e.g., genomic DNA. The double-strand break can stimulate a cell's endogenous DNA-repair pathways (e.g., homology-dependent repair or non-homologous end joining or alternative non-homologous end joining (A-NHEJ) or microhomology-mediated end joining). NHEJ can repair cleaved target nucleic acid without the need for a homologous template. This can sometimes result in small deletions or insertions (indels) in the target nucleic acid at the site of cleavage, and can lead to disruption or alteration of gene expression. HDR can occur when a homologous repair template, or donor, is available. The homologous donor template comprises sequences that are homologous to sequences flanking the target nucleic acid cleavage site. The sister chromatid is generally used by the cell as the repair template. However, for the purposes of genome editing, the repair template is often supplied as an exogenous nucleic acid, such as a plasmid, duplex oligonucleotide, single-strand oligonucleotide, double-stranded oligonucleotide, or viral nucleic acid. With exogenous donor templates, it is common to introduce an additional nucleic acid sequence (such as a transgene) or modification (such as a single or multiple base change or a deletion) between the flanking regions of homology so that the additional or altered nucleic acid sequence also becomes incorporated into the target locus. MMEJ results in a genetic outcome that is similar to NHEJ in that small deletions and insertions can occur at the cleavage site. MMEJ makes use of homologous sequences of a few basepairs flanking the cleavage site to drive a favored end-joining DNA repair outcome. In some instances it may be possible to predict likely repair outcomes based on analysis of potential microhomologies in the nuclease target regions.

Thus, in some cases, homologous recombination is used to insert an exogenous polynucleotide sequence into the target nucleic acid cleavage site. An exogenous polynucleotide sequence is termed a donor polynucleotide (or donor or donor sequence or polynucleotide donor template) herein. In some embodiments, the donor polynucleotide, a portion of the donor polynucleotide, a copy of the donor polynucleotide, or a portion of a copy of the donor polynucleotide is inserted into the target nucleic acid cleavage site. In some embodiments, the donor polynucleotide is an exogenous polynucleotide sequence, i.e., a sequence that does not naturally occur at the target nucleic acid cleavage site.

The modifications of the target DNA due to NHEJ and/or HDR can lead to, for example, mutations, deletions, alterations, integrations, gene correction, gene replacement, gene tagging, transgene insertion, nucleotide deletion, gene disruption, translocations and/or gene mutation. The processes of deleting genomic DNA and integrating non-native nucleic acid into genomic DNA are examples of genome editing.

Genome engineering systems, such as ZFNs, TALENs, HEs and MegaTALs, enable a specific area of the DNA to be modified. Even more recently, CRISPR/Cas systems have been described.

CRISPR Endonuclease System

A CRISPR (Clustered Regularly Interspaced Short Palindromic Repeats) genomic locus can be found in the genomes of many prokaryotes (e.g., bacteria and archaea). In prokaryotes, the CRISPR locus encodes products that function as a type of immune system to help defend the prokaryotes against foreign invaders, such as virus and phage. There are three stages of CRISPR locus function: integration of new sequences into the locus, biogenesis of CRISPR RNA (crRNA), and silencing of foreign invader nucleic acid. Five types of CRISPR systems (e.g., Type I, Type II, Type III, Type U, and Type V) have been identified.

A CRISPR locus includes a number of short repeating sequences referred to as "repeats." The repeats can form hairpin structures and/or comprise unstructured single-stranded sequences. The repeats usually occur in clusters and frequently diverge between species. The repeats are regularly interspaced with unique intervening sequences referred to as "spacers," resulting in a repeat-spacer-repeat locus architecture. The spacers are identical to or have high homology with known foreign invader sequences. A spacer-repeat unit encodes a crisprRNA (crRNA), which is processed into a mature form of the spacer-repeat unit. A crRNA comprises a "seed" or spacer sequence that is involved in targeting a target nucleic acid (in the naturally occurring form in prokaryotes, the spacer sequence targets the foreign invader nucleic acid). A spacer sequence is located at the 5' or 3' end of the crRNA.

A CRISPR locus also comprises polynucleotide sequences encoding CRISPR Associated (Cas) genes. Cas genes encode endonucleases involved in the biogenesis and the interference stages of crRNA function in prokaryotes. Some Cas genes comprise homologous secondary and/or tertiary structures.

Type II CRISPR Systems crRNA biogenesis in a Type II CRISPR system in nature requires a trans-activating CRISPR RNA (tracrRNA). The tracrRNA is modified by endogenous RNaseIII, and then hybridizes to a crRNA repeat in the pre-crRNA array. Endogenous RNaseIII is recruited to cleave the pre-crRNA. Cleaved crRNAs are subjected to exoribonuclease trimming to produce the mature crRNA form (e.g., 5' trimming). The tracrRNA remains hybridized to the crRNA, and the tracrRNA and the crRNA associate with a site-directed polypeptide (e.g., Cas9). The crRNA of the crRNA-tracrRNA-Cas9 complex guides the complex to a target nucleic acid to which the crRNA can hybridize. Hybridization of the crRNA to the target nucleic acid activates Cas9 for targeted nucleic acid cleavage. The target nucleic acid in a Type II CRISPR system is referred to as a protospacer adjacent motif (PAM). In nature, the PAM is essential to facilitate binding of a site-directed polypeptide (e.g., Cas9) to the target nucleic acid. Type II systems (also referred to as Nmeni or CASS4) are further subdivided into Type II-A (CASS4) and II-B (CASS4a). Jinek et al., *Science,* 337 (6096):816-821 (2012) showed that the CRISPR/Cas9 system is useful for RNA-programmable genome editing, and international patent application publication number WO2013/176772 provides numerous examples and applications of the CRISPR/Cas endonuclease system for site-specific genome editing.

Type V CRISPR Systems

Type V CRISPR systems have several important differences from Type II systems. For example, Cpf1 is a single RNA-guided endonuclease that, in contrast to Type II systems, lacks tracrRNA. Zetsche et al., Cell, 163: 1-13 (2015). In fact, Cpf1-associated CRISPR arrays are processed into mature crRNAS without the requirement of an additional trans-activating tracrRNA. The Type V CRISPR array is processed into short mature crRNAs of 42-44 nucleotides in length, with each mature crRNA beginning with 19 nucleotides of direct repeat followed by 23-25 nucleotides of spacer sequence. In contrast, mature crRNAs in Type II systems start with 20-24 nucleotides of spacer sequence followed by about 22 nucleotides of direct repeat. Also, Cpf1 utilizes a T-rich protospacer-adjacent motif such that Cpf1-crRNA complexes efficiently cleave target DNA preceeded by a short T-rich PAM, which is in contrast to the G-rich PAM following the target DNA for Type II systems. Thus, Type V systems cleave at a point that is distant from the PAM, while Type II systems cleave at a point that is adjacent to the PAM. In addition, in contrast to Type II systems, Cpf1 cleaves DNA via a staggered DNA double-stranded break with a 4 or 5 nucleotide 5' overhang. Type II systems cleave via a blunt double-stranded break. Similar to Type II systems, Cpf1 contains a predicted RuvC-like endonuclease domain, but lacks a second HNH endonuclease domain, which is in contrast to Type II systems.

Cas Genes/Polypeptides and Protospacer Adjacent Motifs

Figure 1B:
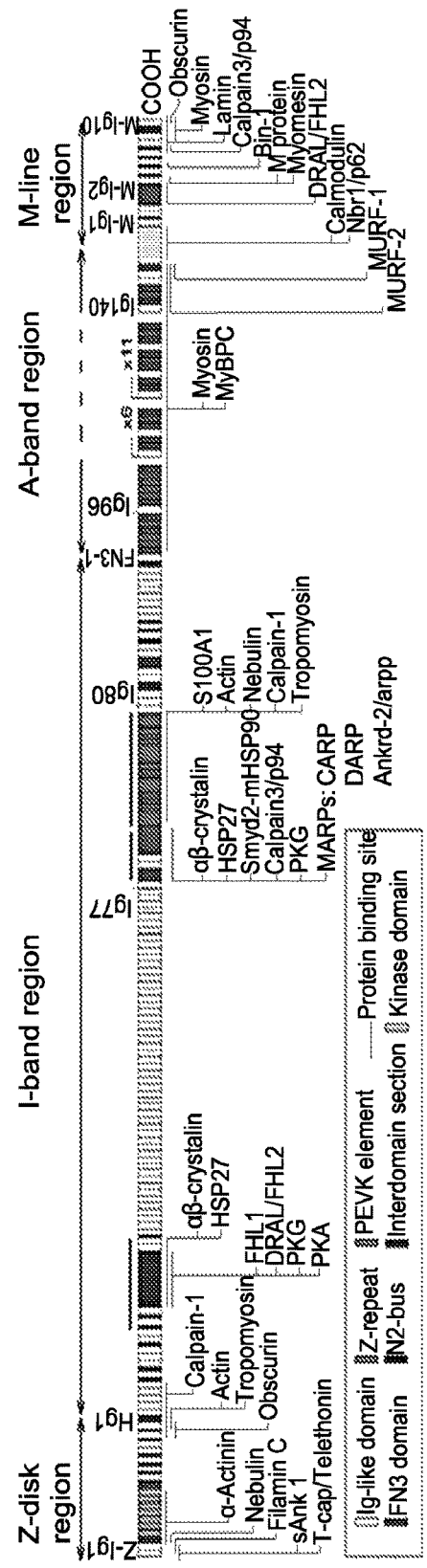
Figure 5:
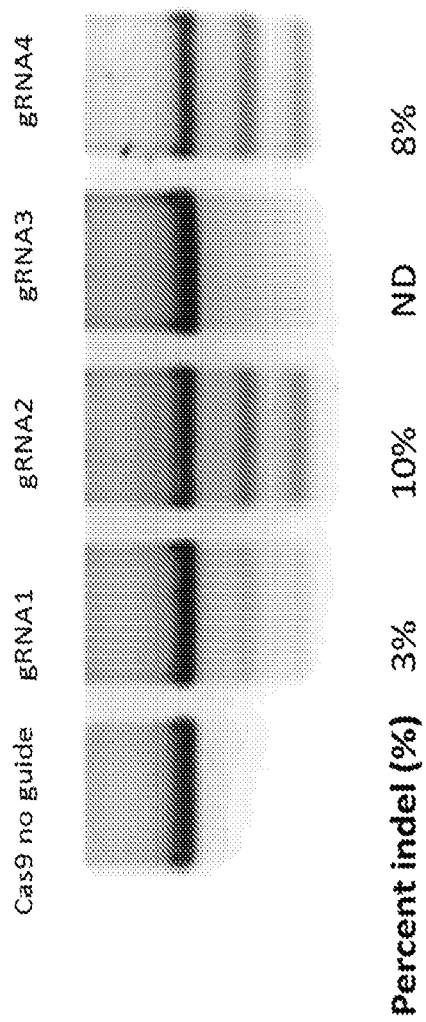
FIG. 5 shows gene correction in patient fibroblasts. Treated cells were verified to have gene modification activity by the T7E1 assay 48 hours after transfection. PCR products were run on a 0.7% ethidium bromide stained agarose gel. The percent indels represents the sum of all NHEJ mediated insertions/deletions for all samples. The T7E1 assay demonstrated 3-10% efficiency in the patient fibroblasts.

Exemplary CRISPR/Cas polypeptides include the Cas9 polypeptides in FIG. 1 of Fonfara et al., *Nucleic Acids Research*, 42: 2577-2590 (2014). The CRISPR/Cas gene naming system has undergone extensive rewriting since the Cas genes were discovered. FIG. 5 of Fonfara, supra, provides PAM sequences for the Cas9 polypeptides from various species.

Site-Directed Polypeptides

A site-directed polypeptide is a nuclease used in genome editing to cleave DNA. The site-directed may be administered to a cell or a patient as either: one or more polypeptides, or one or more mRNAs encoding the polypeptide.

In the context of a CRISPR/Cas or CRISPR/Cpf1 system, the site-directed polypeptide can bind to a guide RNA that, in turn, specifies the site in the target DNA to which the polypeptide is directed. In embodiments of CRISPR/Cas or CRISPR/Cpf1 systems herein, the site-directed polypeptide is an endonuclease, such as a DNA endonuclease.

In some embodiments, a site-directed polypeptide comprises a plurality of nucleic acid-cleaving (i.e., nuclease) domains. Two or more nucleic acid-cleaving domains can be linked together via a linker. In some embodiments, the linker comprises a flexible linker. Linkers may comprise 1, 2, 3, 4, 5, 6, 7, 8, 9, 10, 11, 12, 13, 14, 15, 16, 17, 18, 19, 20, 21, 22, 23, 24, 25, 30, 35, 40 or more amino acids in length.

Naturally-occurring wild-type Cas9 enzymes comprise two nuclease domains, a HNH nuclease domain and a RuvC domain. Herein, the "Cas9" refers to both naturally-occurring and recombinant Cas9s. Cas9 enzymes contemplated herein comprise a HNH or HNH-like nuclease domain, and/or a RuvC or RuvC-like nuclease domain.

HNH or HNH-like domains comprise a McrA-like fold. HNH or HNH-like domains comprises two antiparallel β-strands and an α-helix. HNH or HNH-like domains comprises a metal binding site (e.g., a divalent cation binding site). HNH or HNH-like domains can cleave one strand of a target nucleic acid (e.g., the complementary strand of the crRNA targeted strand).

RuvC or RuvC-like domains comprise an RNaseH or RNaseH-like fold. RuvC/RNaseH domains are involved in a diverse set of nucleic acid-based functions including acting on both RNA and DNA. The RNaseH domain comprises 5 β-strands surrounded by a plurality of α-helices. RuvC/RNaseH or RuvC/RNaseH-like domains comprise a metal binding site (e.g., a divalent cation binding site). RuvC/RNaseH or RuvC/RNaseH-like domains can cleave one strand of a target nucleic acid (e.g., the non-complementary strand of a double-stranded target DNA).

Site-directed polypeptides can introduce double-strand breaks or single-strand breaks in nucleic acids, e.g., genomic DNA. The double-strand break can stimulate a cell's endogenous DNA-repair pathways (e.g., homology-dependent repair (HDR) or non-homologous end joining (NHEJ) or alternative non-homologous end joining (A-NHEJ) or microhomology-mediated end joining (MMEJ)). NHEJ can repair cleaved target nucleic acid without the need for a homologous template. This can sometimes result in small deletions or insertions (indels) in the target nucleic acid at the site of cleavage, and can lead to disruption or alteration of gene expression. HDR can occur when a homologous repair template, or donor, is available. The homologous donor template comprises sequences that are homologous to sequences flanking the target nucleic acid cleavage site. The sister chromatid is generally used by the cell as the repair template. However, for the purposes of genome editing, the repair template is often supplied as an exogenous nucleic acid, such as a plasmid, duplex oligonucleotide, single-strand oligonucleotide or viral nucleic acid. With exogenous donor templates, it is common to introduce an additional nucleic acid sequence (such as a transgene) or modification (such as a single or multiple base change or a deletion) between the flanking regions of homology so that the additional or altered nucleic acid sequence also becomes incorporated into the target locus. MMEJ results in a genetic outcome that is similar to NHEJ in that small deletions and insertions can occur at the cleavage site. MMEJ makes use of homologous sequences of a few basepairs flanking the cleavage site to drive a favored end-joining DNA repair outcome. In some instances it may be possible to predict likely repair outcomes based on analysis of potential microhomologies in the nuclease target regions.

Thus, in some cases, homologous recombination is used to insert an exogenous polynucleotide sequence into the target nucleic acid cleavage site. An exogenous polynucleotide sequence is termed a donor polynucleotide (or donor or donor sequence) herein. In some embodiments, the donor polynucleotide, a portion of the donor polynucleotide, a copy of the donor polynucleotide, or a portion of a copy of the donor polynucleotide is inserted into the target nucleic acid cleavage site. In some embodiments, the donor polynucleotide is an exogenous polynucleotide sequence, i.e., a sequence that does not naturally occur at the target nucleic acid cleavage site.

The modifications of the target DNA due to NHEJ and/or HDR can lead to, for example, mutations, deletions, alterations, integrations, gene correction, gene replacement, gene tagging, transgene insertion, nucleotide deletion, gene disruption, translocations and/or gene mutation. The processes of deleting genomic DNA and integrating non-native nucleic acid into genomic DNA are examples of genome editing.

In some embodiments, the site-directed polypeptide comprises an amino acid sequence having at least 10%, at least 15%, at least 20%, at least 30%, at least 40%, at least 50%, at least 60%, at least 70%, at least 75%, at least 80%, at least 85%, at least 90%, at least 95%, at least 99%, or 100% amino acid sequence identity to a wild-type exemplary site-directed polypeptide [e.g., Cas9 from *S. aureus* decribed in Ran et al., Nature, 520(7546):186-191(2015), Cpf1 from *Acidaminococcus* sp. BV3L6 or *Lachnospiraceae bacterium* ND2006 endonuclease described in Zetsche et al., Cell, 163: 1-13 (2015); and various other site-directed polypeptides].

In some embodiments, the site-directed polypeptide comprises an amino acid sequence having at least 10%, at least 15%, at least 20%, at least 30%, at least 40%, at least 50%, at least 60%, at least 70%, at least 75%, at least 80%, at least 85%, at least 90%, at least 95%, at least 99%, or 100% amino acid sequence identity to a nuclease domain of a wild-type exemplary site-directed polypeptide.

In some embodiments, a site-directed polypeptide comprises at least 70, 75, 80, 85, 90, 95, 97, 99, or 100% identity to a wild-type site-directed polypeptide over 10 contiguous amino acids. In some embodiments, a site-directed polypeptide comprises at most: 70, 75, 80, 85, 90, 95, 97, 99, or 100% identity to a wild-type site-directed polypeptide over 10 contiguous amino acids. In some embodiments, a site-directed polypeptide comprises at least: 70, 75, 80, 85, 90, 95, 97, 99, or 100% identity to a wild-type site-directed polypeptide over 10 contiguous amino acids in a HNH nuclease domain of the site-directed polypeptide. In some embodiments, a site-directed polypeptide comprises at most: 70, 75, 80, 85, 90, 95, 97, 99, or 100% identity to a wild-type site-directed polypeptide over 10 contiguous amino acids in a HNH nuclease domain of the site-directed polypeptide. In some embodiments, a site-directed polypeptide comprises at least: 70, 75, 80, 85, 90, 95, 97, 99, or 100% identity to a wild-type site-directed polypeptide over 10 contiguous amino acids in a RuvC nuclease domain of the site-directed polypeptide. In some embodiments, a site-directed polypeptide comprises at most: 70, 75, 80, 85, 90, 95, 97, 99, or 100% identity to a wild-type site-directed polypeptide over 10 contiguous amino acids in a RuvC nuclease domain of the site-directed polypeptide.

In some embodiments, the site-directed polypeptide comprises a modified form of a wild-type exemplary site-directed polypeptide. The modified form of the wild-type exemplary site-directed polypeptide comprises a mutation that reduces the nucleic acid-cleaving activity of the site-directed polypeptide. In some embodiments, the modified form of the wild-type exemplary site-directed polypeptide has less than 90%, less than 80%, less than 70%, less than 60%, less than 50%, less than 40%, less than 30%, less than 20%, less than 10%, less than 5%, or less than 1% of the nucleic acid-cleaving activity of the wild-type exemplary site-directed polypeptide. The modified form of the site-directed polypeptide can have no substantial nucleic acid-cleaving activity. When a site-directed polypeptide is a modified form that has no substantial nucleic acid-cleaving activity, it is referred to herein as "enzymatically inactive."

In some embodiments, the modified form of the site-directed polypeptide comprises a mutation such that it can induce a single-strand break (SSB) on a target nucleic acid (e.g., by cutting only one of the sugar-phosphate backbones of a double-strand target nucleic acid). In some embodiments, the mutation results in less than 90%, less than 80%, less than 70%, less than 60%, less than 50%, less than 40%, less than 30%, less than 20%, less than 10%, less than 5%, or less than 1% of the nucleic acid-cleaving activity in one or more of the plurality of nucleic acid-cleaving domains of the wild-type site directed polypeptide. In some embodiments, the mutation results in one or more of the plurality of nucleic acid-cleaving domains retaining the ability to cleave the complementary strand of the target nucleic acid, but reducing its ability to cleave the non-complementary strand of the target nucleic acid. In some embodiments, the mutation results in one or more of the plurality of nucleic acid-cleaving domains retaining the ability to cleave the non-complementary strand of the target nucleic acid, but reducing its ability to cleave the complementary strand of the target nucleic acid. One skilled in the art will recognize that mutations other than alanine substitutions are suitable.

Site-directed polypeptides that comprise one substantially inactive nuclease domain are referred to as "nickases".

Nickase variants of Cas9 can be used to increase the specificity of CRISPR-mediated genome editing. Wild type Cas9 is typically guided by a single guide RNA designed to hybridize with a specified ~20 nucleotide sequence in the target sequence (such as an endogenous genomic locus). However, several mismatches can be tolerated between the guide RNA and the target locus, effectively reducing the length of required homology in the target site to, for example, as little as 13 nt of homology, and thereby resulting in elevated potential for binding and double-strand nucleic acid cleavage by the CRISPR/Cas9 complex elsewhere in the target genome—also known as off-target cleavage. Because nickase variants of Cas9 each only cut one strand, in order to create a double-strand break it is necessary for a pair of nickases to bind in close proximity and on opposite strands of the target nucleic acid, thereby creating a pair of nicks, which is the equivalent of a double-strand break. This requires that two separate guide RNAs—one for each nickase—must bind in close proximity and on opposite strands of the target nucleic acid. This requirement essentially doubles the minimum length of homology needed for the double-strand break to occur, thereby reducing the likelihood that a double-strand cleavage event will occur elsewhere in the genome, where the two guide RNA sites—if they exist—are unlikely to be sufficiently close to each other to enable the double-strand break to form. As described in the art, nickases can also be used to promote HDR versus NHEJ. HDR can be used to introduce selected changes into target sites in the genome through the use of specific donor sequences that effectively mediate the desired changes. Descriptions of various CRISPR/Cas systems for use in genome editing can be found, e.g., in international patent application publication number WO2013/176772; Ran et al., supra; and in *Nature Biotechnology* 32, 347-355 (2014), and references cited therein.

Mutations contemplated include substitutions, additions, and deletions, or any combination thereof. In some embodiments, the mutation converts the mutated amino acid to alanine. In some embodiments, the mutation converts the mutated amino acid to another amino acid (e.g., glycine, serine, threonine, cysteine, valine, leucine, isoleucine, methionine, proline, phenylalanine, tyrosine, tryptophan, aspartic acid, glutamic acid, asparagines, glutamine, histidine, lysine, or arginine). In some embodiments, the mutation converts the mutated amino acid to a non-natural amino acid (e.g., selenomethionine). In some embodiments, the mutation converts the mutated amino acid to amino acid mimics (e.g., phosphomimics). In some embodiments, the mutation is a conservative mutation. For example, the mutation can convert the mutated amino acid to amino acids that resemble the size, shape, charge, polarity, conformation, and/or rotamers of the mutated amino acids (e.g., cysteine/serine mutation, lysine/asparagine mutation, histidine/phenylalanine mutation). In some embodiments, the mutation causes a shift in reading frame and/or the creation of a premature stop codon. In some embodiments, mutations cause changes to regulatory regions of genes or loci that affect expression of one or more genes.

In some embodiments, the site-directed polypeptide (e.g., variant, mutated, enzymatically inactive and/or conditionally enzymatically inactive site-directed polypeptide) targets nucleic acid. In some embodiments, the site-directed polypeptide (e.g., variant, mutated, enzymatically inactive and/or conditionally enzymatically inactive endoribonuclease) targets RNA.

In some embodiments, the site-directed polypeptide comprises one or more non-native sequences (e.g., the site-directed polypeptide is a fusion protein).

In some embodiments, the site-directed polypeptide comprises an amino acid sequence comprising at least 15% amino acid identity to a Cas9 from a bacterium (e.g., *S. aureus*), a nucleic acid binding domain, and two nucleic acid cleaving domains (i.e., a HNH domain and a RuvC domain).

In some embodiments, the site-directed polypeptide comprises an amino acid sequence comprising at least 15% amino acid identity to a Cas9 from a bacterium (e.g., *S. aureus*), and two nucleic acid cleaving domains (i.e., a HNH domain and a RuvC domain).

In some embodiments, the site-directed polypeptide comprises an amino acid sequence comprising at least 15% amino acid identity to a Cas9 from a bacterium (e.g., *S. aureus*), and two nucleic acid cleaving domains, wherein one or both of the nucleic acid cleaving domains comprise at least 50% amino acid identity to a nuclease domain from Cas9 from a bacterium (e.g., *S. aureus*).

In some embodiments, the site-directed polypeptide comprises an amino acid sequence comprising at least 15% amino acid identity to a Cas9 from a bacterium (e.g., *S. aureus*), two nucleic acid cleaving domains (i.e., a HNH domain and a RuvC domain), and non-native sequence (for example, a nuclear localization signal) or a linker linking the site-directed polypeptide to a non-native sequence.

In some embodiments, the site-directed polypeptide comprises an amino acid sequence comprising at least 15% amino acid identity to a Cas9 from a bacterium (e.g., *S. aureus*), two nucleic acid cleaving domains (i.e., a HNH domain and a RuvC domain), wherein the site-directed polypeptide comprises a mutation in one or both of the nucleic acid cleaving domains that reduces the cleaving activity of the nuclease domains by at least 50%.

In some embodiments, the site-directed polypeptide comprises an amino acid sequence comprising at least 15% amino acid identity to a Cas9 from a bacterium (e.g., *S. aureus*), and two nucleic acid cleaving domains (i.e., a HNH domain and a RuvC domain), wherein one of the nuclease domains comprises mutation of aspartic acid 10, and/or wherein one of the nuclease domains comprises mutation of histidine 840, and wherein the mutation reduces the cleaving activity of the nuclease domain(s) by at least 50%.

In some embodiments of the invention, the one or more site-directed polypeptides, e.g. DNA endonucleases, include two nickases that together effect one double-strand break at a specific locus in the genome, or four nickases that together effect two double-strand breaks at specific loci in the genome. Alternatively, one site-directed polypeptide, e.g. DNA endonuclease, effects one double-strand break at a specific locus in the genome.

Genome-Targeting Nucleic Acid

The present disclosure provides a genome-targeting nucleic acid that can direct the activities of an associated polypeptide (e.g., a site-directed polypeptide) to a specific target sequence within a target nucleic acid. In some embodiments, the genome-targeting nucleic acid is an RNA. A genome-targeting RNA is referred to as a "guide RNA" or "gRNA" herein. A guide RNA comprises at least a spacer sequence that hybridizes to a target nucleic acid sequence of interest, and a CRISPR repeat sequence. In Type II systems, the gRNA also comprises a tracrRNA sequence. In the Type II guide RNA, the CRISPR repeat sequence and tracrRNA sequence hybridize to each other to form a duplex. In the Type V guide RNA, the crRNA forms a duplex. In both systems, the duplex binds a site-directed polypeptide, such that the guide RNA and site-direct polypeptide form a complex. The genome-targeting nucleic acid provides target specificity to the complex by virtue of its association with the site-directed polypeptide. The genome-targeting nucleic acid thus directs the activity of the site-directed polypeptide.

Exemplary guide RNAs include the spacer sequences shown in the Figures, shown with the genome location of their target sequence and the associated Cas9 cut site, wherein the genome location is based on the GRCh38/hg38 human genome assembly. As is understood by the person of ordinary skill in the art, each guide RNA is designed to include a spacer sequence complementary to its genomic target sequence. For example, each of the spacer sequences in the Figures may be put into a gRNA or sgRNA.

In some embodiments, the genome-targeting nucleic acid is a double-molecule guide RNA. In some embodiments, the genome-targeting nucleic acid is a single-molecule guide RNA.

A double-molecule guide RNA comprises two strands of RNA. The first strand comprises in the 5' to 3' direction, an optional spacer extension sequence, a spacer sequence and a minimum CRISPR repeat sequence. The second strand comprises a minimum tracrRNA sequence (complementary to the minimum CRISPR repeat sequence), a 3' tracrRNA sequence and an optional tracrRNA extension sequence.

A single-molecule guide RNA in a Type II system comprises, in the 5' to 3' direction, an optional spacer extension sequence, a spacer sequence, a minimum CRISPR repeat sequence, a single-molecule guide linker, a minimum tracrRNA sequence, a 3' tracrRNA sequence and an optional tracrRNA extension sequence. The optional tracrRNA extension may comprise elements that contribute additional functionality (e.g., stability) to the guide RNA. The single-molecule guide linker links the minimum CRISPR repeat and the minimum tracrRNA sequence to form a hairpin structure. The optional tracrRNA extension comprises one or more hairpins.

A single-molecule guide RNA in a Type V system comprises, in the 5' to 3' direction, a minimum CRISPR repeat sequence and a spacer sequence.

By way of illustration, guide RNAs used in the CRISPR/Cas system, or other smaller RNAs can be readily synthesized by chemical means, as illustrated below and described in the art. While chemical synthetic procedures are continually expanding, purifications of such RNAs by procedures such as high performance liquid chromatography (HPLC, which avoids the use of gels such as PAGE) tends to become more challenging as polynucleotide lengths increase significantly beyond a hundred or so nucleotides. One approach used for generating RNAs of greater length is to produce two or more molecules that are ligated together. Much longer RNAs, such as those encoding a Cas9 endonuclease, are more readily generated enzymatically. Various types of RNA modifications can be introduced during or after chemical synthesis and/or enzymatic generation of RNAs, e.g., modifications that enhance stability, reduce the likelihood or degree of innate immune response, and/or enhance other attributes, as described in the art.

Spacer Extension Sequence

In some embodiments of genome-targeting nucleic acids, a spacer extension sequence can provide stability and/or provide a location for modifications of a genome-targeting nucleic acid. In some embodiments, a spacer extension sequence is provided. A spacer extension sequence may have a length of more than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400, 1000, 2000, 3000, 4000, 5000, 6000, or 7000 or more nucleotides. A spacer extension sequence may have a length of less than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400, 1000, 2000, 3000, 4000, 5000, 6000, 7000 or more nucleotides. In some embodiments, a spacer extension sequence is less than 10 nucleotides in length. In some embodiments, a spacer extension sequence is between 10-30 nucleotides in length. In some embodiments, a spacer extension sequence is between 30-70 nucleotides in length.

In some embodiments, the spacer extension sequence comprises another moiety (e.g., a stability control sequence, an endoribonuclease binding sequence, a ribozyme). In some embodiments, the moiety increases the stability of a nucleic acid targeting nucleic acid. In some embodiments, the moiety is a transcriptional terminator segment (i.e., a transcription termination sequence). In some embodiments, the moiety functions in a eukaryotic cell. In some embodiments, the moiety functions in a prokaryotic cell. In some embodiments, the moiety functions in both eukaryotic and prokaryotic cells. Non-limiting examples of suitable moieties include: a 5' cap (e.g., a 7-methylguanylate cap (m7 G)), a riboswitch sequence (e.g., to allow for regulated stability and/or regulated accessibility by proteins and protein complexes), a sequence that forms a dsRNA duplex (i.e., a hairpin), a sequence that targets the RNA to a subcellular location (e.g., nucleus, mitochondria, chloroplasts, and the like), a modification or sequence that provides for tracking (e.g., direct conjugation to a fluorescent molecule, conjugation to a moiety that facilitates fluorescent detection, a sequence that allows for fluorescent detection, etc.), and/or a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like).

Spacer Sequence

The spacer sequence hybridizes to a sequence in a target nucleic acid of interest. The spacer of a genome-targeting nucleic acid interacts with a target nucleic acid in a sequence-specific manner via hybridization (i.e., base pairing). The nucleotide sequence of the spacer thus varies depending on the sequence of the target nucleic acid of interest.

In a CRISPR/Cas system herein, the spacer sequence is designed to hybridize to a target nucleic acid that is located 5' of a PAM of the Cas9 enzyme used in the system. Each Cas9 enzyme has a particular PAM sequence that it recognizes in a target DNA. For example, S. aureus recognizes in a target nucleic acid a PAM that comprises the sequence 5'-NNGRRT-3', where R comprises either A or G, where N is any nucleotide and the 5' N is immediately 3' of the target nucleic acid sequence targeted by the spacer sequence.

In some embodiments, the target nucleic acid sequence comprises 21 nucleotides. In some embodiments, the target nucleic acid comprises less than 21 nucleotides. In some embodiments, the target nucleic acid comprises at least: 5, 10, 15, 16, 17, 18, 19, 20, 21, 22, 23, 24, 25, 30 or more nucleotides. In some embodiments, the target nucleic acid comprises at most: 5, 10, 15, 16, 17, 18, 19, 20, 21, 22, 23, 24, 25, 30 or more nucleotides. In some embodiments, the target nucleic acid sequence comprises 21 bases immediately 5' to the first nucleotide of the PAM. For example, in a sequence comprising 5'-NNNNNNNNNNNNNNNNNNNN-NNNNGRRT-3' (SEQ ID NO: 78), the target nucleic acid comprises the sequence that corresponds to the 5' Ns, wherein N is any nucleotide.

In some embodiments, the spacer sequence that hybridizes to the target nucleic acid has a length of at least about 6 nucleotides (nt). The spacer sequence can be at least about 6 nt, at least about 10 nt, at least about 15 nt, at least about 18 nt, at least about 19 nt, at least about 20 nt, at least about 25 nt, at least about 30 nt, at least about 35 nt or at least about 40 nt, from about 6 nt to about 80 nt, from about 6 nt to about 50 nt, from about 6 nt to about 45 nt, from about 6 nt to about 40 nt, from about 6 nt to about 35 nt, from about 6 nt to about 30 nt, from about 6 nt to about 25 nt, from about 6 nt to about 20 nt, from about 6 nt to about 19 nt, from about 10 nt to about 50 nt, from about 10 nt to about 45 nt, from about 10 nt to about 40 nt, from about 10 nt to about 35 nt, from about 10 nt to about 30 nt, from about 10 nt to about 25 nt, from about 10 nt to about 20 nt, from about 10 nt to about 19 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, or from about 20 nt to about 60 nt. In some embodiments, the spacer sequence comprises 20 nucleotides. In some embodiments, the spacer comprises 19 nucleotides.

In some embodiments, the percent complementarity between the spacer sequence and the target nucleic acid is at least about 30%, at least about 40%, at least about 50%, at least about 60%, at least about 65%, at least about 70%, at least about 75%, at least about 80%, at least about 85%, at least about 90%, at least about 95%, at least about 97%, at least about 98%, at least about 99%, or 100%. In some embodiments, the percent complementarity between the spacer sequence and the target nucleic acid is at most about 30%, at most about 40%, at most about 50%, at most about 60%, at most about 65%, at most about 70%, at most about 75%, at most about 80%, at most about 85%, at most about 90%, at most about 95%, at most about 97%, at most about 98%, at most about 99%, or 100%. In some embodiments, the percent complementarity between the spacer sequence and the target nucleic acid is 100% over the six contiguous 5'-most nucleotides of the target sequence of the complementary strand of the target nucleic acid. In some embodiments, the percent complementarity between the spacer sequence and the target nucleic acid is at least 60% over about 20 contiguous nucleotides.

In some embodiments, a spacer sequence is designed or chosen using a computer program. The computer program can use variables, such as predicted melting temperature, secondary structure formation, predicted annealing temperature, sequence identity, genomic context, chromatin accessibility, % GC, frequency of genomic occurrence (e.g., of sequences that are identical or are similar but vary in one or more spots as a result of mismatch, insertion or deletion), methylation status, presence of SNPs, and the like.

Minimum CRISPR Repeat Sequence

In some embodiments, a minimum CRISPR repeat sequence is a sequence with at least about 30%, about 40%, about 50%, about 60%, about 65%, about 70%, about 75%, about 80%, about 85%, about 90%, about 95%, or 100% sequence identity to a reference CRISPR repeat sequence (e.g., crRNA from S. aureus).

A minimum CRISPR repeat sequence comprises nucleotides that can hybridize to a minimum tracrRNA sequence in a cell. The minimum CRISPR repeat sequence and a minimum tracrRNA sequence form a duplex, i.e. a base-paired double-stranded structure. Together, the minimum CRISPR repeat sequence and the minimum tracrRNA sequence bind to the site-directed polypeptide. At least a part of the minimum CRISPR repeat sequence hybridizes to the minimum tracrRNA sequence. In some embodiments, at least a part of the minimum CRISPR repeat sequence comprises at least about 30%, about 40%, about 50%, about 60%, about 65%, about 70%, about 75%, about 80%, about 85%, about 90%, about 95%, or 100% complementary to the minimum tracrRNA sequence. In some embodiments, at least a part of the minimum CRISPR repeat sequence comprises at most about 30%, about 40%, about 50%, about 60%, about 65%, about 70%, about 75%, about 80%, about 85%, about 90%, about 95%, or 100% complementary to the minimum tracrRNA sequence.

The minimum CRISPR repeat sequence can have a length from about 7 nucleotides to about 100 nucleotides. For example, the length of the minimum CRISPR repeat sequence is from about 7 nucleotides (nt) to about 50 nt, from about 7 nt to about 40 nt, from about 7 nt to about 30 nt, from about 7 nt to about 25 nt, from about 7 nt to about 20 nt, from about 7 nt to about 15 nt, from about 8 nt to about 40 nt, from about 8 nt to about 30 nt, from about 8 nt to about 25 nt, from about 8 nt to about 20 nt, from about 8 nt to about 15 nt, from about 15 nt to about 100 nt, from about 15 nt to about 80 nt, from about 15 nt to about 50 nt, from about 15 nt to about 40 nt, from about 15 nt to about 30 nt, or from about 15 nt to about 25 nt. In some embodiments, the minimum CRISPR repeat sequence is approximately 9 nucleotides in length. In some embodiments, the minimum CRISPR repeat sequence is approximately 12 nucleotides in length.

In some embodiments, the minimum CRISPR repeat sequence is at least about 60% identical to a reference minimum CRISPR repeat sequence (e.g., wild-type crRNA from *S. aureus*) over a stretch of at least 6, 7, or 8 contiguous nucleotides. For example, the minimum CRISPR repeat sequence is at least about 65% identical, at least about 70% identical, at least about 75% identical, at least about 80% identical, at least about 85% identical, at least about 90% identical, at least about 95% identical, at least about 98% identical, at least about 99% identical or 100% identical to a reference minimum CRISPR repeat sequence over a stretch of at least 6, 7, or 8 contiguous nucleotides.

Minimum tracrRNA Sequence

In some embodiments, a minimum tracrRNA sequence is a sequence with at least about 30%, about 40%, about 50%, about 60%, about 65%, about 70%, about 75%, about 80%, about 85%, about 90%, about 95%, or 100% sequence identity to a reference tracrRNA sequence (e.g., wild type tracrRNA from *S. aureus*).

A minimum tracrRNA sequence comprises nucleotides that hybridize to a minimum CRISPR repeat sequence in a cell. A minimum tracrRNA sequence and a minimum CRISPR repeat sequence form a duplex, i.e. a base-paired double-stranded structure. Together, the minimum tracrRNA sequence and the minimum CRISPR repeat bind to a site-directed polypeptide. At least a part of the minimum tracrRNA sequence can hybridize to the minimum CRISPR repeat sequence. In some embodiments, the minimum tracrRNA sequence is at least about 30%, about 40%, about 50%, about 60%, about 65%, about 70%, about 75%, about 80%, about 85%, about 90%, about 95%, or 100% complementary to the minimum CRISPR repeat sequence.

The minimum tracrRNA sequence can have a length from about 7 nucleotides to about 100 nucleotides. For example, the minimum tracrRNA sequence can be from about 7 nucleotides (nt) to about 50 nt, from about 7 nt to about 40 nt, from about 7 nt to about 30 nt, from about 7 nt to about 25 nt, from about 7 nt to about 20 nt, from about 7 nt to about 15 nt, from about 8 nt to about 40 nt, from about 8 nt to about 30 nt, from about 8 nt to about 25 nt, from about 8 nt to about 20 nt, from about 8 nt to about 15 nt, from about 15 nt to about 100 nt, from about 15 nt to about 80 nt, from about 15 nt to about 50 nt, from about 15 nt to about 40 nt, from about 15 nt to about 30 nt or from about 15 nt to about 25 nt long. In some embodiments, the minimum tracrRNA sequence is approximately 9 nucleotides in length. In some embodiments, the minimum tracrRNA sequence is approximately 12 nucleotides. In some embodiments, the minimum tracrRNA consists of tracrRNA nt 23-48 described in Jinek et al., supra.

In some embodiments, the minimum tracrRNA sequence is at least about 60% identical to a reference minimum tracrRNA (e.g., wild type, tracrRNA from *S. aureus*) sequence over a stretch of at least 6, 7, or 8 contiguous nucleotides. For example, the minimum tracrRNA sequence is at least about 65% identical, about 70% identical, about 75% identical, about 80% identical, about 85% identical, about 90% identical, about 95% identical, about 98% identical, about 99% identical or 100% identical to a reference minimum tracrRNA sequence over a stretch of at least 6, 7, or 8 contiguous nucleotides.

In some embodiments, the duplex between the minimum CRISPR RNA and the minimum tracrRNA comprises a double helix. In some embodiments, the duplex between the minimum CRISPR RNA and the minimum tracrRNA comprises at least about 1, 2, 3, 4, 5, 6, 7, 8, 9, or 10 or more nucleotides. In some embodiments, the duplex between the minimum CRISPR RNA and the minimum tracrRNA comprises at most about 1, 2, 3, 4, 5, 6, 7, 8, 9, or 10 or more nucleotides.

In some embodiments, the duplex comprises a mismatch (i.e., the two strands of the duplex are not 100% complementary). In some embodiments, the duplex comprises at least about 1, 2, 3, 4, or 5 or mismatches. In some embodiments, the duplex comprises at most about 1, 2, 3, 4, or 5 or mismatches. In some embodiments, the duplex comprises no more than 2 mismatches.

Bulges

In some embodiments, there is a "bulge" in the duplex between the minimum CRISPR RNA and the minimum tracrRNA. The bulge is an unpaired region of nucleotides within the duplex. In some embodiments, the bulge contributes to the binding of the duplex to the site-directed polypeptide. A bulge comprises, on one side of the duplex, an unpaired 5'-XXXY-3' where X is any purine and Y comprises a nucleotide that can form a wobble pair with a nucleotide on the opposite strand, and an unpaired nucleotide region on the other side of the duplex. The number of unpaired nucleotides on the two sides of the duplex can be different.

In one example, the bulge comprises an unpaired purine (e.g., adenine) on the minimum CRISPR repeat strand of the bulge. In some embodiments, a bulge comprises an unpaired 5'-AAGY-3' of the minimum tracrRNA sequence strand of the bulge, where Y comprises a nucleotide that can form a wobble pairing with a nucleotide on the minimum CRISPR repeat strand.

In some embodiments, a bulge on the minimum CRISPR repeat side of the duplex comprises at least 1, 2, 3, 4, or 5 or more unpaired nucleotides. In some embodiments, a bulge on the minimum CRISPR repeat side of the duplex comprises at most 1, 2, 3, 4, or 5 or more unpaired nucleotides. In some embodiments, a bulge on the minimum CRISPR repeat side of the duplex comprises 1 unpaired nucleotide.

In some embodiments, a bulge on the minimum tracrRNA sequence side of the duplex comprises at least 1, 2, 3, 4, 5, 6, 7, 8, 9, or 10 or more unpaired nucleotides. In some embodiments, a bulge on the minimum tracrRNA sequence side of the duplex comprises at most 1, 2, 3, 4, 5, 6, 7, 8, 9, or 10 or more unpaired nucleotides. In some embodiments, a bulge on a second side of the duplex (e.g., the minimum tracrRNA sequence side of the duplex) comprises 4 unpaired nucleotides.

In some embodiments, a bulge comprises at least one wobble pairing. In some embodiments, a bulge comprises at most one wobble pairing. In some embodiments, a bulge comprises at least one purine nucleotide. In some embodiments, a bulge comprises at least 3 purine nucleotides. In some embodiments, a bulge sequence comprises at least 5 purine nucleotides. In some embodiments, a bulge sequence comprises at least one guanine nucleotide. In some embodiments, a bulge sequence comprises at least one adenine nucleotide.

Hairpins

In various embodiments, one or more hairpins are located 3' to the minimum tracrRNA in the 3' tracrRNA sequence.

In some embodiments, the hairpin starts at least about 1, 2, 3, 4, 5, 6, 7, 8, 9, 10, 15, or 20 or more nucleotides 3' from the last paired nucleotide in the minimum CRISPR repeat and minimum tracrRNA sequence duplex. In some embodiments, the hairpin can start at most about 1, 2, 3, 4, 5, 6, 7, 8, 9 or 10 or more nucleotides 3' of the last paired nucleotide in the minimum CRISPR repeat and minimum tracrRNA sequence duplex.

In some embodiments, a hairpin comprises at least about 1, 2, 3, 4, 5, 6, 7, 8, 9, 10, 15, or 20 or more consecutive nucleotides. In some embodiments, a hairpin comprises at most about 1, 2, 3, 4, 5, 6, 7, 8, 9, 10, 15, or more consecutive nucleotides.

In some embodiments, a hairpin comprises a CC dinucleotide (i.e., two consecutive cytosine nucleotides).

In some embodiments, a hairpin comprises duplexed nucleotides (e.g., nucleotides in a hairpin, hybridized together). For example, a hairpin comprises a CC dinucleotide that is hybridized to a GG dinucleotide in a hairpin duplex of the 3' tracrRNA sequence.

One or more of the hairpins can interact with guide RNA-interacting regions of a site-directed polypeptide.

In some embodiments, there are two or more hairpins, and in some embodiments there are three or more hairpins.

3' tracrRNA Sequence

In some embodiments, a 3' tracrRNA sequence comprises a sequence with at least about 30%, about 40%, about 50%, about 60%, about 65%, about 70%, about 75%, about 80%, about 85%, about 90%, about 95%, or 100% sequence identity to a reference tracrRNA sequence (e.g., a tracrRNA from S. aureus).

In some embodiments, the 3' tracrRNA sequence has a length from about 6 nucleotides to about 100 nucleotides. For example, the 3' tracrRNA sequence can have a length from about 6 nucleotides (nt) to about 50 nt, from about 6 nt to about 40 nt, from about 6 nt to about 30 nt, from about 6 nt to about 25 nt, from about 6 nt to about 20 nt, from about 6 nt to about 15 nt, from about 8 nt to about 40 nt, from about 8 nt to about 30 nt, from about 8 nt to about 25 nt, from about 8 nt to about 20 nt, from about 8 nt to about 15 nt, from about 15 nt to about 100 nt, from about 15 nt to about 80 nt, from about 15 nt to about 50 nt, from about 15 nt to about 40 nt, from about 15 nt to about 30 nt, or from about 15 nt to about 25 nt. In some embodiments, the 3' tracrRNA sequence has a length of approximately 14 nucleotides.

In some embodiments, the 3' tracrRNA sequence is at least about 60% identical to a reference 3' tracrRNA sequence (e.g., wild type 3' tracrRNA sequence from S. aureus) over a stretch of at least 6, 7, or 8 contiguous nucleotides. For example, the 3' tracrRNA sequence is at least about 60% identical, about 65% identical, about 70% identical, about 75% identical, about 80% identical, about 85% identical, about 90% identical, about 95% identical, about 98% identical, about 99% identical, or 100% identical, to a reference 3' tracrRNA sequence (e.g., wild type 3' tracrRNA sequence from S. aureus) over a stretch of at least 6, 7, or 8 contiguous nucleotides.

In some embodiments, a 3' tracrRNA sequence comprises more than one duplexed region (e.g., hairpin, hybridized region). In some embodiments, a 3' tracrRNA sequence comprises two duplexed regions.

In some embodiments, the 3' tracrRNA sequence comprises a stem loop structure. In some embodiments, a stem loop structure in the 3' tracrRNA comprises at least 1, 2, 3, 4, 5, 6, 7, 8, 9, 10, 15 or 20 or more nucleotides. In some embodiments, the stem loop structure in the 3' tracrRNA comprises at most 1, 2, 3, 4, 5, 6, 7, 8, 9 or 10 or more nucleotides. In some embodiments, the stem loop structure comprises a functional moiety. For example, the stem loop structure may comprise an aptamer, a ribozyme, a protein-interacting hairpin, a CRISPR array, an intron, or an exon. In some embodiments, the stem loop structure comprises at least about 1, 2, 3, 4, or 5 or more functional moieties. In some embodiments, the stem loop structure comprises at most about 1, 2, 3, 4, or 5 or more functional moieties.

In some embodiments, the hairpin in the 3' tracrRNA sequence comprises a P-domain. In some embodiments, the P-domain comprises a double-stranded region in the hairpin.

tracrRNA Extension Sequence

A tracrRNA extension sequence may be provided whether the tracrRNA is in the context of single-molecule guides or double-molecule guides. In some embodiments, a tracrRNA extension sequence has a length from about 1 nucleotide to about 400 nucleotides. In some embodiments, a tracrRNA extension sequence has a length of more than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, or 400 nucleotides. In some embodiments, a tracrRNA extension sequence has a length from about 20 to about 5000 or more nucleotides. In some embodiments, a tracrRNA extension sequence has a length of more than 1000 nucleotides. In some embodiments, a tracrRNA extension sequence has a length of less than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400 or more nucleotides. In some embodiments, a tracrRNA extension sequence can have a length of less than 1000 nucleotides. In some embodiments, a tracrRNA extension sequence comprises less than 10 nucleotides in length. In some embodiments, a tracrRNA extension sequence is 10-30 nucleotides in length. In some embodiments, tracrRNA extension sequence is 30-70 nucleotides in length.

In some embodiments, the tracrRNA extension sequence comprises a functional moiety (e.g., a stability control sequence, ribozyme, endoribonuclease binding sequence). In some embodiments, the functional moiety comprises a transcriptional terminator segment (i.e., a transcription termination sequence). In some embodiments, the functional moiety has a total length from about 10 nucleotides (nt) to about 100 nucleotides, from about 10 nt to about 20 nt, from about 20 nt to about 30 nt, from about 30 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt, from about 15 nt to about 80 nt, from about 15 nt to about 50 nt, from about 15 nt to about 40 nt, from about 15 nt to about 30 nt, or from about 15 nt to about 25 nt. In some embodiments, the functional moiety functions in a eukaryotic cell. In some embodiments, the functional moiety functions in a prokaryotic cell. In some embodiments, the functional moiety functions in both eukaryotic and prokaryotic cells.

Non-limiting examples of suitable tracrRNA extension functional moieties include a 3' poly-adenylated tail, a riboswitch sequence (e.g., to allow for regulated stability and/or regulated accessibility by proteins and protein complexes), a sequence that forms a dsRNA duplex (i.e., a hairpin), a sequence that targets the RNA to a subcellular location (e.g., nucleus, mitochondria, chloroplasts, and the like), a modification or sequence that provides for tracking (e.g., direct conjugation to a fluorescent molecule, conjugation to a moiety that facilitates fluorescent detection, a sequence that allows for fluorescent detection, etc.), and/or a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like). In some embodiments, a tracrRNA extension sequence comprises a primer binding site or a molecular index (e.g., barcode sequence). In some embodiments, the tracrRNA extension sequence comprises one or more affinity tags.

Single-Molecule Guide Linker Sequence

In some embodiments, the linker sequence of a single-molecule guide nucleic acid has a length from about 3 nucleotides to about 100 nucleotides. In Jinek et al., supra, for example, a simple 4 nucleotide "tetraloop" (-GAAA-) was used, Science, 337(6096):816-821 (2012). An illustrative linker has a length from about 3 nucleotides (nt) to about 90 nt, from about 3 nt to about 80 nt, from about 3 nt to about 70 nt, from about 3 nt to about 60 nt, from about 3 nt to about 50 nt, from about 3 nt to about 40 nt, from about 3 nt to about 30 nt, from about 3 nt to about 20 nt, from about 3 nt to about 10 nt. For example, the linker can have a length from about 3 nt to about 5 nt, from about 5 nt to about 10 nt, from about 10 nt to about 15 nt, from about 15 nt to about 20 nt, from about 20 nt to about 25 nt, from about 25 nt to about 30 nt, from about 30 nt to about 35 nt, from about 35 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. In some embodiments, the linker of a single-molecule guide nucleic acid is between 4 and 40 nucleotides. In some embodiments, a linker is at least about 100, 500, 1000, 1500, 2000, 2500, 3000, 3500, 4000, 4500, 5000, 5500, 6000, 6500, or 7000 or more nucleotides. In some embodiments, a linker is at most about 100, 500, 1000, 1500, 2000, 2500, 3000, 3500, 4000, 4500, 5000, 5500, 6000, 6500, or 7000 or more nucleotides.

Linkers can comprise any of a variety of sequences, although preferably the linker will not comprise sequences that have extensive regions of homology with other portions of the guide RNA, which might cause intramolecular binding that could interfere with other functional regions of the guide. In Jinek et al., supra, a simple 4 nucleotide sequence -GAAA- was used, Science, 337(6096):816-821 (2012), but numerous other sequences, including longer sequences can likewise be used.

In some embodiments, the linker sequence comprises a functional moiety. For example, the linker sequence may comprise an aptamer, a ribozyme, a protein-interacting hairpin, a CRISPR array, an intron, or an exon. In some embodiments, the linker sequence comprises at least about 1, 2, 3, 4, or 5 or more functional moieties. In some embodiments, the linker sequence comprises at most about 1, 2, 3, 4, or 5 or more functional moieties.

Genome Engineering Strategies to Correct Cells by Replacement of One or More Mutations in the Gene, by Knocking-In Titin cDNA Into the Locus of the Corresponding Gene or by Knocking-Out Exons in the Gene A step of the ex vivo methods of the invention involves editing/correcting a mutation in titin gene in, for example, a progenitor cell (in some embodiments an eCSC, or primary cardiomyocyte). Likewise, a step of the in vivo methods of the invention involves editing/correcting the titin gene in cells in a patient using genome engineering.

Patients with titin-based cardiomyopathies or other titin-opathies exhibit a wide range of mutations in the titin gene. Therefore, different patients will generally require different correction strategies. Any CRISPR endonuclease may be used in the methods of the invention, each CRISPR endonuclease having its own associated PAM, which may or may not be disease specific. Exemplary gRNA spacer sequences for targeting the titin gene with a CRISPR/Cas9 endonuclease from *S. aureus* are set out in the Figures.

A genome engineering strategy involves replacement of one or more mutations in the gene or knocking-in titin cDNA into the locus of the corresponding gene by homology directed repair (HDR), which is also known as homologous recombination (HR). Homology directed repair is one strategy for treating patients that have inactivating mutations to the titin protein. These strategies will restore the titin protein and completely reverse the diseased state. This strategy will require a more custom approach based on the location of the patient's inactivating mutation(s). Donor nucleotides for correcting mutations are small (<300 bp). This is advantageous, as HDR efficiencies may be inversely related to the size of the donor molecule. Also, it is expected that the donor templates can fit into size constrained adeno-associated virus (AAV) molecules, which have been shown to be an effective means of donor template delivery.

Homology direct repair is a cellular mechanism for repairing double-stranded breaks (DSBs). The most common form is homologous recombination. There are additional pathways for HDR, including single-strand annealing and alternative-HDR. Genome engineering tools allow researchers to manipulate the cellular homologous recombination pathways to create site-specific modifications to the genome. It has been found that cells can repair a double-stranded break using a synthetic donor molecule provided in trans. Therefore, by introducing a double-stranded break near a specific mutation and providing a suitable donor, targeted changes can be made in the genome. Specific cleavage increases the rate of HDR more than 1,000 fold above the rate of 1 in $10^6$ cells receiving a homologous donor alone. The rate of homology directed repair (HDR) at a particular nucleotide is a function of the distance to the cut site, so choosing overlapping or nearest target sites is important. Gene editing offers the advantage over gene addition, as correcting in situ leaves the rest of the genome unperturbed.

Supplied donors for editing by HDR vary markedly but generally contain the intended sequence with small or large flanking homology arms to allow annealing to the genomic DNA. The homology regions flanking the introduced genetic changes can be 30 bp or smaller, or as large as a multi-kilobase cassette that can contain promoters, cDNAs, etc. Both single-stranded and double-stranded oligonucleotide donors have been used. These oligonucleotides range in size from less than 100 nt to over 500 nt, though longer ssDNA can also be generated and used. Double-stranded donors are often used, including PCR amplicons, plasmids, and mini-circles. In general, it has been found that an AAV vector is a very effective means of delivery of a donor template, though the packaging limits for individual donors is <5 kb. Active transcription of the donor increased HDR three-fold, indicating the inclusion of promoter may increase conversion. Conversely, CpG methylation of the donor decreased gene expression and HDR.

In addition to wildtype endonucleases, such as Cas9, nickase variants exist that have one or the other nuclease domain inactivated resulting in cutting of only one DNA strand. HDR can be directed from individual Cas nickases or using pairs of nickases that flank the target area. Donors can be single-stranded, nicked, or dsDNA.

The donor DNA can be supplied with the nuclease or independently by a variety of different methods, for example by transfection, nano-particle, micro-injection, or viral transduction. A range of tethering options have been proposed to increase the availability of the donors for HDR. Examples include attaching the donor to the nuclease, attaching to DNA binding proteins that bind nearby, or attaching to proteins that are involved in DNA end binding or repair.

The repair pathway choice can be guided by a number of culture conditions, such as those that influence cell cycling, or by targeting of DNA repair and associated proteins. For example, to increase HDR, key NHEJ molecules can be suppressed, such as KU70, KU80 or DNA ligase IV known as Scr7.

Without a donor present, the ends from a DNA break or ends from different breaks can be joined using the several nonhomologous repair pathways in which the DNA ends are joined with little or no base-pairing at the junction. In addition to canonical NHEJ, there are similar repair mechanisms, such as alt-NHEJ. If there are two breaks, the intervening segment can be deleted or inverted. NHEJ repair pathways can lead to insertions, deletions or mutations at the joints.

In addition to genome editing by NHEJ or HDR, site-specific gene insertions have been conducted that use both the NHEJ pathway and HR. A combination approach may be applicable in certain settings, possibly including intron/exon borders. NHEJ may prove effective for ligation in the intron, while the error-free HDR may be better suited in the coding region.

As stated previously, the titin gene contains 363 protein-coding exons. Any one or more of the 331 exons may be repaired in order to correct a mutation and restore titin activity. As a further alternative, titin cDNA may be knocked-in to the locus of the corresponding gene or knocked-in to a safe harbor site, such as AAVS1. In some embodiments, the methods provide one gRNA or a pair of gRNAs that can be used to facilitate incorporation of a new sequence from a polynucleotide donor template to repair one or more mutations.

Some embodiments of the methods provide gRNA pairs that make a deletion by cutting the gene twice, one gRNA cutting at the 5' end of one or more mutations and the other gRNA cutting at the 3' end of one or more mutations that facilitates insertion of a new sequence from a polynucleotide donor template to replace the one or more mutations. The cutting may be accomplished by a pair of DNA endonucleases that each makes a DSB in the genome, or by multiple nickases that together make a DSB in the genome.

Alternatively, some embodiments of the methods provide one gRNA to make one double-strand cut around one or more mutations that facilitates insertion of a new sequence from a polynucleotide donor template to replace the one or more mutations. The double-strand cut may be made by a single DNA endonuclease or multiple nickases that together make a DSB in the genome.

Illustrative modifications within the titin gene include replacements within or proximal to the mutations referred to above, such as within the region of less than 3 kb, less than 2 kb, less than 1 kb, less than 0.5 kb upstream or downstream of the specific mutation. Given the relatively wide variations of mutations in the titin gene, it will be appreciated that numerous variations of the replacements referenced above (including without limitation larger as well as smaller deletions), would be expected to result in restoration of titin protein activity.

Such variants include replacements that are larger in the 5' and/or 3' direction than the specific mutation in question, or smaller in either direction. Accordingly, by "proximal" with respect to specific replacements, it is intended that the DSB locus associated with a desired replacement boundary (also referred to herein as an endpoint) may be within a region that is less than about 3 kb from the reference locus noted. In some embodiments, the DSB locus is more proximal and within 2 kb, within 1 kb, within 0.5 kb, or within 0.1 kb. In the case of small replacement, the desired endpoint is at or "adjacent to" the reference locus, by which it is intended that the endpoint is within 100 bp, within 50 bp, within 25 bp, or less than about 10 bp to 5 bp from the reference locus.

Embodiments comprising larger or smaller replacements are expected to provide the same benefit, as long as the titin activity is restored. It is thus expected that many variations of the replacements described and illustrated herein will be effective for ameliorating cardiomyopathies or other titin-opathies.

Target Sequence Selection

Preferentially, shifts in the location of the 5' boundary and/or the 3' boundary relative to particular reference loci are used to facilitate or enhance particular applications of genome editing, which depend in part on the endonuclease system selected for the editing, as further described and illustrated herein.

In a first aspect of such target sequence selection, many endonuclease systems have rules or criteria that guide the initial selection of potential target sites for cleavage, such as the requirement of a PAM sequence motif in a particular position adjacent to the DNA cleavage sites in the case of CRISPR Type II or Type V endonucleases.

In another aspect of target sequence selection or optimization, the frequency of "off-target" activity for a particular combination of target sequence and genome editing endonuclease (i.e. the frequency of DSBs occurring at sites other than the selected target sequence) is assessed relative to the frequency of on-target activity. In some cases, cells that have been correctly edited at the desired locus may have a selective advantage relative to other cells. Illustrative, but nonlimiting, examples of a selective advantage include the acquisition of attributes such as enhanced rates of replication, persistence, resistance to certain conditions, enhanced rates of successful engraftment or persistence in vivo following introduction into a patient, and other attributes associated with the maintenance or increased numbers or viability of such cells. In other cases, cells that have been correctly edited at the desired locus may be positively selected for by one or more screening methods used to identify, sort or otherwise select for cells that have been correctly edited. Both selective advantage and directed selection methods may take advantage of the phenotype associated with the correction. In some embodiments, cells may be edited two or more times in order to create a second modification that creates a new phenotype that is used to select or purify the intended population of cells. Such a second modification could be created by adding a second gRNA for a selectable or screenable marker.

Whether any selective advantage is applicable or any directed selection is to be applied in a particular case, target sequence selection is also guided by consideration of off-target frequencies in order to enhance the effectiveness of the application and/or reduce the potential for undesired alterations at sites other than the desired target. As described further and illustrated herein and in the art, the occurrence of off-target activity is influenced by a number of factors including similarities and dissimilarities between the target site and various off target sites, as well as the particular endonuclease used. In many cases, bioinformatics tools are available that assist in the prediction of off-target activity, and frequently such tools can also be used to identify the most likely sites of off-target activity, which can then be assessed in experimental settings to evaluate relative frequencies of off-target to on-target activity, thereby allowing the selection of sequences that have higher relative on-target activities. Illustrative examples of such techniques are provided herein, and others are known in the art.

Another aspect of target sequence selection relates to homologous recombination events. It is well known that sequences sharing regions of homology can serve as focal points for homologous recombination events that result in deletion of intervening sequences. Such recombination events occur during the normal course of replication of chromosomes and other DNA sequences, and also at other times when DNA sequences are being synthesized, such as in the case of repairs of double-strand breaks (DSBs), which occur on a regular basis during the normal cycle but may also be enhanced by the occurrence of various events (such as UV light and other inducers of DNA breakage) or the presence of certain agents (such as various chemical inducers). Many such inducers cause DSBs to occur indiscriminately in the genome, and DSBs are regularly being induced and repaired in normal cells. During repair, the original sequence may be reconstructed with complete fidelity, however, in some cases, small insertions or deletions (referred to as "indels") are introduced at the DSB site.

DSBs may also be specifically induced at particular locations, as in the case of the endonucleases systems described herein, which can be used to cause directed or preferential gene modification events at selected chromosomal locations. The tendency for homologous sequences to be subject to recombination in the context of DNA repair (as well as replication) can be taken advantage of in a number of circumstances, and is the basis for one application of genome editing systems, such as CRISPR, in which homology directed repair is used to insert a sequence of interest, provided through use of a "donor" polynucleotide, into a desired chromosomal location.

Regions of homology between particular sequences, which can be small regions of "microhomology" that may comprise as few as ten basepairs or less, can also be used to bring about desired deletions. For example, a single DSB is introduced at a site that exhibits microhomology with a nearby sequence. During the normal course of repair of such DSB, a result that occurs with high frequency is the deletion of the intervening sequence as a result of recombination being facilitated by the DSB and concomitant cellular repair process.

In some circumstances, however, selecting target sequences within regions of homology can also give rise to much larger deletions, including gene fusions (when the deletions are in coding regions), which may or may not be desired given the particular circumstances.

The examples provided herein further illustrate the selection of various target regions for the creation of DSBs designed to induce replacements that result in restoration of titin activity, as well as the selection of specific target sequences within such regions that are designed to minimize off-target events relative to on-target events.

Preferred gRNAs have sufficiently high on-target activity to achieve desired levels of genome editing at the selected locus, and relatively lower off-target activity to reduce the likelihood of alterations at other chromosomal loci. The ratio of on-target to off-target activity is often referred to as the "specificity" of a gRNA.

For initial screening of predicted off-target activities, there are a number of bioinformatics tools known and publicly available that can be used to predict the most likely off-target sites; and since binding to target sites in the CRISPR/Cas9 nuclease system is driven by Watson-Crick base pairing between complementary sequences, the degree of dissimilarity (and therefore reduced potential for off-target binding) is essentially related to primary sequence differences: mismatches and bulges, i.e. bases that are changed to a non-complementary base, and insertions or deletions of bases in the potential off-target site relative to the target site. An exemplary bioinformatics tool called COSMID (CRISPR Off-target Sites with Mismatches, Insertions and Deletions) (available on the web at crispr.bme.gatech.edu) compiles such similarities.

Nucleic Acid Modifications

In some embodiments, polynucleotides introduced into cells comprise one or more modifications that can be used, for example, to enhance activity, stability or specificity, alter delivery, reduce innate immune responses in host cells, or for other enhancements, as further described herein and known in the art.

In certain embodiments, modified polynucleotides are used in the CRISPR/Cas system, in which case the guide RNAs (either single-molecule guides or double-molecule guides) and/or a DNA or an RNA encoding a Cas endonuclease introduced into a cell can be modified, as described and illustrated below. Such modified polynucleotides can be used in the CRISPR/Cas system to edit any one or more genomic loci.

Using the CRISPR/Cas system for purposes of nonlimiting illustrations of such uses, modifications of guide RNAs can be used to enhance the formation or stability of the CRISPR/Cas genome editing complex comprising guide RNAs, which may be single-molecule guides or double-molecule, and a Cas endonuclease. Modifications of guide RNAs can also or alternatively be used to enhance the initiation, stability or kinetics of interactions between the genome editing complex with the target sequence in the genome, which can be used, for example, to enhance on-target activity. Modifications of guide RNAs can also or alternatively be used to enhance specificity, e.g., the relative rates of genome editing at the on-target site as compared to effects at other (off-target) sites.

Modifications can also or alternatively be used to increase the stability of a guide RNA, e.g., by increasing its resistance to degradation by ribonucleases (RNases) present in a cell, thereby causing its half-life in the cell to be increased. Modifications enhancing guide RNA half-life can be particularly useful in embodiments in which a Cas endonuclease is introduced into the cell to be edited via an RNA that needs to be translated in order to generate endonuclease, because increasing the half-life of guide RNAs introduced at the same time as the RNA encoding the endonuclease can be used to increase the time that the guide RNAs and the encoded Cas endonuclease co-exist in the cell.

Modifications can also or alternatively be used to decrease the likelihood or degree to which RNAs introduced into cells elicit innate immune responses. Such responses, which have been well characterized in the context of RNA interference (RNAi), including small-interfering RNAs (siRNAs), as described below and in the art, tend to be associated with reduced half-life of the RNA and/or the elicitation of cytokines or other factors associated with immune responses.

One or more types of modifications can also be made to RNAs encoding an endonuclease that are introduced into a cell, including, without limitation, modifications that enhance the stability of the RNA (such as by increasing its degradation by RNAses present in the cell), modifications that enhance translation of the resulting product (i.e. the endonuclease), and/or modifications that decrease the likelihood or degree to which the RNAs introduced into cells elicit innate immune responses.

Combinations of modifications, such as the foregoing and others, can likewise be used. In the case of CRISPR/Cas, for example, one or more types of modifications can be made to guide RNAs (including those exemplified above), and/or one or more types of modifications can be made to RNAs encoding Cas endonuclease (including those exemplified above).

By way of illustration, guide RNAs used in the CRISPR/Cas system, or other smaller RNAs can be readily synthesized by chemical means, enabling a number of modifications to be readily incorporated, as known in the art. While chemical synthetic procedures are continually expanding, purifications of such RNAs by procedures such as high performance liquid chromatography (HPLC, which avoids the use of gels such as PAGE) tends to become more challenging as polynucleotide lengths increase significantly beyond a hundred or so nucleotides. One approach used for generating chemically-modified RNAs of greater length is to produce two or more molecules that are ligated together. Much longer RNAs, such as those encoding a Cas9 endonuclease, are more readily generated enzymatically. While fewer types of modifications are generally available for use in enzymatically produced RNAs, there are still modifications that can be used to, e.g., enhance stability, reduce the likelihood or degree of innate immune response, and/or enhance other attributes, as described further below and in the art; and new types of modifications are regularly being developed.

By way of illustration of various types of modifications, especially those used frequently with smaller chemically synthesized RNAs, modifications can comprise one or more nucleotides modified at the 2' position of the sugar. Such modifications are routinely incorporated into oligonucleotides and these oligonucleotides have been shown to have a higher Tm (i.e., higher target binding affinity) than 2'-deoxyoligonucleotides against a given target. Similar modifications may also be made at other positions on the oligonucleotide, particularly the 3' position of the sugar on the 3' terminal nucleotide and the 5' position of 5' terminal nucleotide. Oligonucleotides may also have sugar mimetics, such as cyclobutyls in place of the pentofuranosyl group.

A number of nucleotide and nucleoside modifications have been shown to make the oligonucleotide into which they are incorporated more resistant to nuclease digestion than the native oligonucleotide; these modified oligos survive intact for a longer time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S, and $CH_2$ component parts.

In some embodiments, both a sugar and an internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone.

Guide RNAs can also include, additionally or alternatively, nucleobase (often referred to in the art simply as "base") modifications or substitutions. As used herein, "unmodified" or "natural" nucleobases include adenine (A), guanine (G), thymine (T), cytosine (C), and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine, and 2,6-diaminopurine. Kornberg, A., DNA Replication, W. H. Freeman & Co., San Francisco, pp75-77 (1980); Gebeyehu et al., Nucl. Acids Res. 15:4513 (1997). A "universal" base known in the art, e.g., inosine, can also be included. 5-Me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, 1993, pp. 276-278) and are embodiments of base substitutions.

Thus, the term "modified" refers to a non-natural sugar, phosphate, or base that is incorporated into a guide RNA, an endonuclease, or both a guide RNA and an endonuclease. It is not necessary for all positions in a given oligonucleotide to be uniformly modified, and in fact more than one of the aforementioned modifications may be incorporated in a single oligonucleotide, or even in a single nucleoside within an oligonucleotide.

Longer polynucleotides that are less amenable to chemical synthesis and are typically produced by enzymatic synthesis can also be modified by various means. Such modifications can include, for example, the introduction of certain nucleotide analogs, the incorporation of particular sequences or other moieties at the 5' or 3' ends of molecules, and other modifications. By way of illustration, the mRNA encoding Cas9 is approximately 4 kb in length and can be synthesized by in vitro transcription. Modifications to the mRNA can be applied to, e.g., increase its translation or stability (such as by increasing its resistance to degradation with a cell), or to reduce the tendency of the RNA to elicit an innate immune response that is often observed in cells following introduction of exogenous RNAs, particularly longer RNAs such as that encoding Cas9.

Numerous such modifications have been described in the art, such as polyA tails, 5' cap analogs (e.g., Anti Reverse Cap Analog (ARCA) or m7G(5')ppp(5')G (mCAP)), modified 5' or 3' untranslated regions (UTRs), use of modified bases (such as Pseudo-UTP, 2-Thio-UTP, 5-Methylcytidine-5'-Triphosphate (5-Methyl-CTP) or N6-Methyl-ATP), or treatment with phosphatase to remove 5' terminal phosphates. These and other modifications are known in the art, and new modifications of RNAs are regularly being developed.

There are numerous commercial suppliers of modified RNAs, including for example, TriLink Biotech, AxoLabs, Bio-Synthesis Inc., Dharmacon and many others. As described by TriLink, for example, 5-Methyl-CTP can be used to impart desirable characteristics, such as increased nuclease stability, increased translation or reduced interaction of innate immune receptors with in vitro transcribed RNA. 5-Methylcytidine-5'-Triphosphate (5-Methyl-CTP), N6-Methyl-ATP, as well as Pseudo-UTP and 2-Thio-UTP, have also been shown to reduce innate immune stimulation in culture and in vivo while enhancing translation, as illustrated in publications by Kormann et al. and Warren et al. referred to below.

It has been shown that chemically modified mRNA delivered in vivo can be used to achieve improved therapeutic effects; see, e.g., Kormann et al., Nature Biotechnology 29, 154-157 (2011). Such modifications can be used, for example, to increase the stability of the RNA molecule and/or reduce its immunogenicity. Using chemical modifications such as Pseudo-U, N6-Methyl-A, 2-Thio-U and 5-Methyl-C, it was found that substituting just one quarter of the uridine and cytidine residues with 2-Thio-U and 5-Methyl-C respectively resulted in a significant decrease in toll-like receptor (TLR) mediated recognition of the mRNA in mice. By reducing the activation of the innate immune system, these modifications can be used to effectively increase the stability and longevity of the mRNA in vivo; see, e.g., Kormann et al., supra.

Thus, a large variety of modifications have been developed in the art and applied to enhance RNA stability, reduce innate immune responses, and/or achieve other benefits that can be useful in connection with the introduction of polynucleotides into human cells, as described herein; see, e.g., the reviews by Whitehead K A et al., Annual Review of Chemical and Biomolecular Engineering, 2: 77-96 (2011); Gaglione and Messere, Mini Rev Med Chem, 10(7):578-95 (2010); Chernolovskaya et al, Curr Opin Mol Ther., 12(2): 158-67 (2010); Deleavey et al., Curr Protoc Nucleic Acid Chem Chapter 16:Unit 16.3 (2009); Behlke, Oligonucleotides 18(4):305-19 (2008); Fucini et al., Nucleic Acid Ther 22(3): 205-210 (2012); Bremsen et al., Front Genet 3:154 (2012).

As noted above, there are a number of commercial suppliers of modified RNAs, many of which have specialized in modifications designed to improve the effectiveness of siRNAs. A variety of approaches are offered based on various findings reported in the literature. For example, Dharmacon notes that replacement of a non-bridging oxygen with sulfur (phosphorothioate, PS) has been extensively used to improve nuclease resistance of siRNAs, as reported by Kole, Nature Reviews Drug Discovery 11:125-140 (2012). Modifications of the 2'-position of the ribose have been reported to improve nuclease resistance of the internucleotide phosphate bond while increasing duplex stability (Tm), which has also been shown to provide protection from immune activation. A combination of moderate PS backbone modifications with small, well-tolerated 2'-substitutions (2'-O-Methyl, 2'-Fluoro, 2'-Hydro) have been associated with highly stable siRNAs for applications in vivo, as reported by Soutschek et al. Nature 432:173-178 (2004); and 2'-O-Methyl modifications have been reported to be effective in improving stability as reported by Volkov, Oligonucleotides 19:191-202 (2009). With respect to decreasing the induction of innate immune responses, modifying specific sequences with 2'-O-Methyl, 2'-Fluoro, 2'-Hydro have been reported to reduce TLR7/TLR8 interaction while generally preserving silencing activity; see, e.g., Judge et al., Mol. Ther. 13:494-505 (2006); and Cekaite et al., J. Mol. Biol. 365:90-108 (2007). Additional modifications, such as 2-thiouracil, pseudouracil, 5-methylcytosine, 5-methyluracil, and N6-methyladenosine have also been shown to minimize the immune effects mediated by TLR3, TLR7, and TLR8; see, e.g., Kariko, K. et al., Immunity 23:165-175 (2005).

As is also known in the art, and commercially available, a number of conjugates can be applied to polynucleotides, such as RNAs, for use herein that can enhance their delivery and/or uptake by cells, including for example, cholesterol, tocopherol and folic acid, lipids, peptides, polymers, linkers and aptamers; see, e.g., the review by Winkler, Ther. Deliv. 4:791-809 (2013), and references cited therein.

Codon-Optimization

In some embodiments, a polynucleotide encoding a site-directed polypeptide is codon-optimized according to methods standard in the art for expression in the cell containing the target DNA of interest. For example, if the intended target nucleic acid is in a human cell, a human codon-optimized polynucleotide encoding Cas9 is contemplated for use for producing the Cas9 polypeptide.

Complexes of a Genome-Targeting Nucleic Acid and a Site-Directed Polypeptide

A genome-targeting nucleic acid interacts with a site-directed polypeptide (e.g., a nucleic acid-guided nuclease such as Cas9), thereby forming a complex. The genome-targeting nucleic acid guides the site-directed polypeptide to a target nucleic acid.

Nucleic Acids Encoding System Components

In another aspect, the present disclosure provides a nucleic acid comprising a nucleotide sequence encoding a genome-targeting nucleic acid of the disclosure, a site-directed polypeptide of the disclosure, and/or any nucleic acid or proteinaceous molecule necessary to carry out the embodiments of the methods of the disclosure.

In some embodiments, the nucleic acid encoding a genome-targeting nucleic acid of the disclosure, a site-directed polypeptide of the disclosure, and/or any nucleic acid or proteinaceous molecule necessary to carry out the embodiments of the methods of the disclosure comprises a vector (e.g., a recombinant expression vector).

The term "vector" refers to a nucleic acid molecule capable of transporting another nucleic acid to which it has been linked. One type of vector is a "plasmid", which refers to a circular double-stranded DNA loop into which additional nucleic acid segments can be ligated. Another type of vector is a viral vector, wherein additional nucleic acid segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome.

In some embodiments, vectors are capable of directing the expression of nucleic acids to which they are operatively linked. Such vectors are referred to herein as "recombinant expression vectors", or more simply "expression vectors", which serve equivalent functions.

The term "operably linked" means that the nucleotide sequence of interest is linked to regulatory sequence(s) in a manner that allows for expression of the nucleotide sequence. The term "regulatory sequence" is intended to include, for example, promoters, enhancers and other expression control elements (e.g., polyadenylation signals). Such regulatory sequences are well known in the art and are described, for example, in Goeddel; Gene Expression Technology: Methods in Enzymology 185, Academic Press, San Diego, Calif. (1990). Regulatory sequences include those that direct constitutive expression of a nucleotide sequence in many types of host cells, and those that direct expression of the nucleotide sequence only in certain host cells (e.g., tissue-specific regulatory sequences). It will be appreciated by those skilled in the art that the design of the expression vector can depend on such factors as the choice of the target cell, the level of expression desired, and the like.

Expression vectors contemplated include, but are not limited to, viral vectors based on vaccinia virus, poliovirus, adenovirus, adeno-associated virus, SV40, herpes simplex virus, human immunodeficiency virus, retrovirus (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus) and other recombinant vectors. Other vectors contemplated for eukaryotic target cells include, but are not limited to, the vectors pXT1, pSG5, pSVK3, pBPV, pMSG, and pSVLSV40 (Pharmacia). Other vectors may be used so long as they are compatible with the host cell.

In some embodiments, a vector comprises one or more transcription and/or translation control elements. Depending on the host/vector system utilized, any of a number of suitable transcription and translation control elements, including constitutive and inducible promoters, transcription enhancer elements, transcription terminators, etc. may be used in the expression vector. In some embodiments, the vector is a self-inactivating vector that either inactivates the viral sequences or the components of the CRISPR machinery or other elements.

Non-limiting examples of suitable eukaryotic promoters (i.e., promoters functional in a eukaryotic cell) include those from cytomegalovirus (CMV) immediate early, herpes simplex virus (HSV) thymidine kinase, early and late SV40, long terminal repeats (LTRs) from retrovirus, human elongation factor-1 promoter (EF1), a hybrid construct comprising the cytomegalovirus (CMV) enhancer fused to the chicken beta-actin promoter (CAG), murine stem cell virus promoter (MSCV), phosphoglycerate kinase-1 locus promoter (PGK), and mouse metallothionein-I.

For expressing small RNAs, including guide RNAs used in connection with Cas endonuclease, various promoters such as RNA polymerase III promoters, including for example U6 and H1, can be advantageous. Descriptions of and parameters for enhancing the use of such promoters are known in art, and additional information and approaches are regularly being described; see, e.g., Ma, H. et al., *Molecular Therapy-Nucleic Acids* 3, e161 (2014) doi:10.1038/mtna.2014.12.

The expression vector may also contain a ribosome binding site for translation initiation and a transcription terminator. The expression vector may also include appropriate sequences for amplifying expression. The expression vector may also include nucleotide sequences encoding non-native tags (e.g., histidine tag, hemagglutinin tag, green fluorescent protein, etc.) that are fused to the site-directed polypeptide, thus resulting in a fusion protein.

In some embodiments, a promoter is an inducible promoter (e.g., a heat shock promoter, tetracycline-regulated promoter, steroid-regulated promoter, metal-regulated promoter, estrogen receptor-regulated promoter, etc.). In some embodiments, a promoter is a constitutive promoter (e.g., CMV promoter, UBC promoter). In some embodiments, the promoter is a spatially restricted and/or temporally restricted promoter (e.g., a tissue specific promoter, a cell type specific promoter, etc.).

In some embodiments, the nucleic acid encoding a genome-targeting nucleic acid of the disclosure and/or a site-directed polypeptide are packaged into or on the surface of delivery vehicles for delivery to cells. Delivery vehicles contemplated include, but are not limited to, nanospheres, liposomes, quantum dots, nanoparticles, polyethylene glycol particles, hydrogels, and micelles. As described in the art, a variety of targeting moieties can be used to enhance the preferential interaction of such vehicles with desired cell types or locations.

Introduction of the complexes, polypeptides, and nucleic acids of the disclosure into cells can occur by viral or bacteriophage infection, transfection, conjugation, protoplast fusion, lipofection, electroporation, nucleofection, calcium phosphate precipitation, polyethyleneimine (PEI)-mediated transfection, DEAE-dextran mediated transfection, liposome-mediated transfection, particle gun technology, calcium phosphate precipitation, direct micro-injection, nanoparticle-mediated nucleic acid delivery, and the like.

Delivery

Guide RNA polynucleotides (RNA or DNA) and/or endonuclease polynucleotide(s) (RNA or DNA) can be delivered by viral or non-viral delivery vehicles known in the art. Alternatively, endonuclease polypeptide(s) may be delivered by non-viral delivery vehicles known in the art, such as electroporation or lipid nanoparticles. In further alternative embodiments, the DNA endonuclease may be delivered as one or more polypeptides, either alone or pre-complexed with one or more guide RNAs, or one or more crRNA together with a tracrRNA.

Polynucleotides may be delivered by non-viral delivery vehicles including, but not limited to, nanoparticles, liposomes, ribonucleoproteins, positively charged peptides, small molecule RNA-conjugates, aptamer-RNA chimeras, and RNA-fusion protein complexes. Some exemplary non-viral delivery vehicles are described in Peer and Lieberman, Gene Therapy, 18: 1127-1133 (2011) (which focuses on non-viral delivery vehicles for siRNA that are also useful for delivery of other polynucleotides).

Polynucleotides, such as guide RNA, sgRNA, and mRNA encoding an endonuclease, may be delivered to a cell or a patient by a lipid nanoparticle (LNP).

A LNP refers to any particle having a diameter of less than 1000 nm, 500 nm, 250 nm, 200 nm, 150 nm, 100 nm, 75 nm, 50 nm, or 25 nm. Alternatively, a nanoparticle may range in size from 1-1000 nm, 1-500 nm, 1-250 nm, 25-200 nm, 25-100 nm, 35-75 nm, or 25-60 nm.

LNPs may be made from cationic, anionic, or neutral lipids. Neutral lipids, such as the fusogenic phospholipid DOPE or the membrane component cholesterol, may be included in LNPs as 'helper lipids' to enhance transfection activity and nanoparticle stability. Limitations of cationic lipids include low efficacy owing to poor stability and rapid clearance, as well as the generation of inflammatory or anti-inflammatory responses.

LNPs may also be comprised of hydrophobic lipids, hydrophilic lipids, or both hydrophobic and hydrophilic lipids.

Any lipid or combination of lipids that are known in the art may be used to produce a LNP. Examples of lipids used to produce LNPs are: DOTMA, DOSPA, DOTAP, DMRIE, DC-cholesterol, DOTAP-cholesterol, GAP-DMORIE-DPyPE, and GL67A-DOPE-DMPE-polyethylene glycol (PEG). Examples of cationic lipids are: 98N12-5, C12-200, DLin-KC2-DMA (KC2), DLin-MC3-DMA (MC3), XTC, MD1, and 7C1. Examples of neutral lipids are: DPSC, DPPC, POPC, DOPE, and SM. Examples of PEG-modified lipids are: PEG-DMG, PEG-CerC14, and PEG-CerC20.

The lipids may be combined in any number of molar ratios to produce a LNP. In addition, the polynucleotide(s) may be combined with lipid(s) in a wide range of molar ratios to produce a LNP.

As stated previously, the site-directed polypeptide and genome-targeting nucleic acid may each be administered separately to a cell or a patient. On the other hand, the site-directed polypeptide may be pre-complexed with one or more guide RNAs, or one or more crRNA together with a tracrRNA. The pre-complexed material may then be administered to a cell or a patient. Such pre-complexed material is known as a ribonucleoprotein particle (RNP).

RNA is capable of forming specific interactions with RNA or DNA. While this property is exploited in many biological processes, it also comes with the risk of promiscuous interactions in a nucleic acid-rich cellular environment. One solution to this problem is the formation of ribonucleoprotein particles (RNPs), in which the RNA is pre-complexed with an endonuclease. Another benefit of the RNP is protection of the RNA from degradation.

The endonuclease in the RNP may be modified or unmodified. Likewise, the gRNA, crRNA, tracrRNA, or sgRNA may be modified or unmodified. Numerous modifications are known in the art and may be used.

The endonuclease and sgRNA are generally combined in a 1:1 molar ratio. Alternatively, the endonuclease, crRNA and tracrRNA are generally combined in a 1:1:1 molar ratio. However, a wide range of molar ratios may be used to produce a RNP.

A recombinant adeno-associated virus (AAV) vector may be used for delivery. Techniques to produce rAAV particles, in which an AAV genome to be packaged that includes the polynucleotide to be delivered, rep and cap genes, and helper virus functions are provided to a cell are standard in the art. Production of rAAV requires that the following components are present within a single cell (denoted herein as a packaging cell): a rAAV genome, AAV rep and cap genes separate from (i.e., not in) the rAAV genome, and helper virus functions. The AAV rep and cap genes may be from any AAV serotype for which recombinant virus can be derived, and may be from a different AAV serotype than the rAAV genome ITRs, including, but not limited to, AAV serotypes AAV-1, AAV-2, AAV-3, AAV-4, AAV-5, AAV-6, AAV-7, AAV-8, AAV-9, AAV-10, AAV-11, AAV-12, AAV-13 and AAV rh.74. Production of pseudotyped rAAV is disclosed in, for example, international patent application publication number WO 01/83692. See Table 1.

TABLE 1

| AAV Serotype | Genbank Accession No. |
| --- | --- |
| AAV-1 | NC_002077.1 |
| AAV-2 | NC_001401.2 |
| AAV-3 | NC_001729.1 |
| AAV-3B | AF028705.1 |
| AAV-4 | NC_001829.1 |
| AAV-5 | NC_006152.1 |
| AAV-6 | AF028704.1 |
| AAV-7 | NC_006260.1 |
| AAV-8 | NC_006261.1 |
| AAV-9 | AX753250.1 |
| AAV-10 | AY631965.1 |
| AAV-11 | AY631966.1 |
| AAV-12 | DQ813647.1 |
| AAV-13 | EU285562.1 |

A method of generating a packaging cell involves creating a cell line that stably expresses all of the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, Proc. Natl. Acad. S6. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line is then infected with a helper virus, such as adenovirus. The advantages of this method are that the cells are selectable and are suitable for large-scale production of rAAV. Other examples of suitable methods employ adenovirus or baculovirus, rather than plasmids, to introduce rAAV genomes and/or rep and cap genes into packaging cells.

General principles of rAAV production are reviewed in, for example, Carter, 1992, Current Opinions in Biotechnology, 1533-539; and Muzyczka, 1992, Curr. Topics in Microbial. and Immunol., 158:97-129). Various approaches are described in Ratschin et al., Mol. Cell. Biol. 4:2072 (1984); Hermonat et al., Proc. Natl. Acad. Sci. USA, 81:6466 (1984); Tratschin et al., Mol . Cell. Biol. 5:3251 (1985); McLaughlin et al., J. Virol., 62:1963 (1988); and Lebkowski et al., 1988 Mol. Cell. Biol., 7:349 (1988). Samulski et al.

(1989, J. Virol., 63:3822-3828); U.S. Pat. No. 5,173,414; WO 95/13365 and corresponding U.S. Pat. No. 5,658.776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. (1995) Vaccine 13:1244-1250; Paul et al. (1993) Human Gene Therapy 4:609-615; Clark et al. (1996) Gene Therapy 3:1124-1132; U.S. Pat. Nos. 5,786,211; 5,871,982; and 6,258,595.

AAV vector serotypes can be matched to target cell types. For example, the following exemplary cell types may be transduced by the indicated AAV serotypes among others. See Table 2.

TABLE 2

| Tissue/Cell Type | Serotype |
| --- | --- |
| Liver | AAV8, AAV9 |
| Skeletal muscle | AAV1, AAV7, AAV6, AAV8, AAV9 |
| Central nervous system | AAV5, AAV1, AAV4 |
| RPE | AAV5, AAV4 |
| Photoreceptor cells | AAV5 |
| Lung | AAV9 |
| Heart | AAV8, rh74 |
| Pancreas | AAV8 |
| Kidney | AAV2 |

In some embodiments, Cas9 mRNA, sgRNA targeting one or two loci in the titin gene, and donor DNA are each separately formulated into lipid nanoparticles, or are all co-formulated into one lipid nanoparticle.

In some embodiments, Cas9 mRNA is formulated in a lipid nanoparticle, while sgRNA and donor DNA are delivered in an AAV vector.

Genetically Modified Cells

The term "genetically modified cell" refers to a cell that comprises at least one genetic modification introduced by genome editing (e.g., using the CRISPR/Cas system). In some ex vivo embodiments herein, the genetically modified cell is a genetically modified progenitor cell. In some in vivo embodiments herein, the genetically modified cell is a genetically modified heart or skeletal muscle cell. A genetically modified cell comprising an exogenous genome-targeting nucleic acid and/or an exogenous nucleic acid encoding a genome-targeting nucleic acid is contemplated herein.

The term "control treated population" describes a population of cells that has been treated with identical media, viral induction, nucleic acid sequences, temperature, confluency, flask size, pH, etc., with the exception of the addition of the genome editing components. Any method known in the art can be used to measure restoration of titin gene or protein expression or activity, for example, Western Blot analysis of the titin protein or quantifying titin mRNA.

The term "isolated cell" refers to a cell that has been removed from an organism in which it was originally found, or a descendant of such a cell. Optionally, the cell has been cultured in vitro, e.g., under defined conditions or in the presence of other cells. Optionally, the cell is later introduced into a second organism or re-introduced into the organism from which it (or the cell from which it is descended) was isolated.

The term "isolated population" with respect to an isolated population of cells refers to a population of cells that has been removed and separated from a mixed or heterogeneous population of cells. In some embodiments, an isolated population is a substantially pure population of cells, as compared to the heterogeneous population from which the cells were isolated or enriched. In some embodiments, the isolated population is an isolated population of human progenitor cells, e.g., a substantially pure population of human progenitor cells, as compared to a heterogeneous population of cells comprising human progenitor cells and cells from which the human progenitor cells were derived.

The term "substantially enhanced," with respect to a particular cell population, refers to a population of cells in which the occurrence of a particular type of cell is increased relative to pre-existing or reference levels, by at least 2-fold, at least 3-, at least 4-, at least 5-, at least 6-, at least 7-, at least 8-, at least 9, at least 10-, at least 20-, at least 50-, at least 100-, at least 400-, at least 1000-, at least 5000-, at least 20000-, at least 100000- or more fold depending, e.g., on the desired levels of such cells for ameliorating a cardiomyopathy or other titinopathy.

The term "substantially enriched" with respect to a particular cell population, refers to a population of cells that is at least about 10%, about 20%, about 30%, about 40%, about 50%, about 60%, about 70% or more with respect to the cells making up a total cell population.

The terms "substantially enriched" or "substantially pure" with respect to a particular cell population, refers to a population of cells that is at least about 75%, at least about 85%, at least about 90%, or at least about 95% pure, with respect to the cells making up a total cell population. That is, the terms "substantially pure" or "essentially purified," with regard to a population of progenitor cells, refers to a population of cells that contain fewer than about 20%, about 15%, about 10%, about 9%, about 8%, about 7%, about 6%, about 5%, about 4%, about 3%, about 2%, about 1%, or less than 1%, of cells that are not progenitor cells as defined by the terms herein.

Implanting Cells Into Patients

Another step of the ex vivo methods of the invention involves implanting the hepatocytes into patients. This implanting step may be accomplished using any method of implantation known in the art. For example, the genetically modified cells may be injected directly in the patient's liver or otherwise administered to the patient.

Another step of the ex vivo methods of the invention involves implanting the eCSCs or primary cardiomyocytes into patients. This implanting step may be accomplished using any method of implantation known in the art. For example, the genetically modified cells may be injected directly in the patient's heart or otherwise administered to the patient.

Pharmaceutically Acceptable Carriers

The ex vivo methods of administering progenitor cells to a subject contemplated herein involve the use of therapeutic compositions comprising progenitor cells.

Therapeutic compositions contain a physiologically tolerable carrier together with the cell composition, and optionally at least one additional bioactive agent as described herein, dissolved or dispersed therein as an active ingredient. In some embodiments, the therapeutic composition is not substantially immunogenic when administered to a mammal or human patient for therapeutic purposes, unless so desired.

In general, the progenitor cells described herein are administered as a suspension with a pharmaceutically acceptable carrier. One of skill in the art will recognize that a pharmaceutically acceptable carrier to be used in a cell composition will not include buffers, compounds, cryopreservation agents, preservatives, or other agents in amounts that substantially interfere with the viability of the cells to be delivered to the subject. A formulation comprising cells can include e.g., osmotic buffers that permit cell membrane integrity to be maintained, and optionally, nutrients to maintain cell viability or enhance engraftment upon administration. Such formulations and suspensions are known to those of skill in the art and/or can be adapted for use with the progenitor cells, as described herein, using routine experimentation.

A cell composition can also be emulsified or presented as a liposome composition, provided that the emulsification procedure does not adversely affect cell viability. The cells and any other active ingredient can be mixed with excipients that are pharmaceutically acceptable and compatible with the active ingredient, and in amounts suitable for use in the therapeutic methods described herein.

Additional agents included in a cell composition can include pharmaceutically acceptable salts of the components therein. Pharmaceutically acceptable salts include the acid addition salts (formed with the free amino groups of the polypeptide) that are formed with inorganic acids, such as, for example, hydrochloric or phosphoric acids, or such organic acids as acetic, tartaric, mandelic and the like. Salts formed with the free carboxyl groups can also be derived from inorganic bases, such as, for example, sodium, potassium, ammonium, calcium or ferric hydroxides, and such organic bases as isopropylamine, trimethylamine, 2-ethyl-amino ethanol, histidine, procaine and the like.

Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active compound used in the cell compositions that is effective in the treatment of a particular disorder or condition will depend on the nature of the disorder or condition, and can be determined by standard clinical techniques.

Administration & Efficacy

The terms "administering," "introducing" and "transplanting" are used interchangeably in the context of the placement of cells, e.g., progenitor cells, into a subject, by a method or route that results in at least partial localization of the introduced cells at a desired site, such as a site of injury or repair, such that a desired effect(s) is produced. The cells e.g., progenitor cells, or their differentiated progeny can be administered by any appropriate route that results in delivery to a desired location in the subject where at least a portion of the implanted cells or components of the cells remain viable. The period of viability of the cells after administration to a subject can be as short as a few hours, e.g., twenty-four hours, to a few days, to as long as several years, or even the life time of the patient, i.e., long-term engraftment. For example, in some embodiments described herein, an effective amount of myogenic progenitor cells is administered via a systemic route of administration, such as an intraperitoneal or intravenous route.

The terms "individual", "subject," "host" and "patient" are used interchangeably herein and refer to any subject for whom diagnosis, treatment or therapy is desired. In some embodiments, the subject is a mammal. In some embodiments, the subject is a human being.

When administered prophylactically, treatment methods described herein are administered to a subject in advance of any symptom of a cardiomyopathy or other titinopathy. Accordingly, the prophylactic administration serves to prevent a cardiomyopathy or other titinopathy.

When provided therapeutically, treatment methods described herein are administered to a subject at (or after) the onset of a symptom of a cardiomyopathy or other titinopathy.

In some embodiments, the term "effective amount" refers to the amount of a composition needed to be administered to prevent or alleviate at least one symptom of cardiomyopathy or other titinopathy, and relates to a sufficient amount of a composition to provide the desired effect, e.g., to treat a subject having a cardiomyopathy or other titinopathy. The term "therapeutically effective amount" therefore refers to an amount of composition that is sufficient to promote a particular effect when administered to a typical subject, such as one who has or is at risk for a cardiomyopathy or other titinopathy. An effective amount would also include an amount sufficient to prevent or delay the development of a symptom of the disease, alter the course of a symptom of the disease (for example but not limited to, slow the progression of a symptom of the disease), or reverse a symptom of the disease. It is understood that for any given case, an appropriate "effective amount" can be determined by one of ordinary skill in the art using routine experimentation.

Modest and incremental increases in the levels of functional titin protein expressed in cells of patients having a cardiomyopathy or other titinopathy can be beneficial for ameliorating one or more symptoms of the disease, for increasing long-term survival, and/or for reducing side effects associated with other treatments. In some embodiments, effective treatment of a subject gives rise to at least about 3%, 5% or 7% functional titin protein relative to total titin protein in the treated subject. In some embodiments, functional titin protein will be at least about 10% of total titin protein. In some embodiments, functional titin protein will be at least about 20% to 30% of total titin protein. Similarly, the provision of even relatively limited subpopulations of cells having significantly elevated levels of functional titin protein can be beneficial in various patients because in some situations normalized cells will have a selective advantage relative to diseased cells. However, even modest levels of functional titin protein can be beneficial for ameliorating one or more aspects of a cardiomyopathy or other titinopathy in patients. In some embodiments, about 10%, about 20%, about 30%, about 40%, about 50%, about 60%, about 70%, about 80%, about 90% or more of the modified cells in patients are producing increased levels of functional titin protein.

"Administered" refers to the delivery of a composition into a subject by a method or route that results in at least partial localization of the cell composition at a desired site. A cell composition can be administered by any appropriate route that results in effective treatment in the subject, i.e. administration results in delivery to a desired location in the subject where at least a portion of the composition delivered, i.e. at least $1 \times 10^4$ cells are delivered to the desired site for a period of time. Modes of administration include injection, infusion, instillation, or ingestion. "Injection" includes, without limitation, intravenous, intramuscular, intra-arterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some embodiments, the route is intravenous. For the delivery of cells, administration by injection or infusion is generally preferred.

In one embodiment, administration is systemic. The phrases "systemic administration," "administered systemically", "peripheral administration" and "administered peripherally" refer to the administration other than directly into a target site, tissue, or organ, such that it enters, instead, the subject's circulatory system.

Kits

The present disclosure provides kits for carrying out the methods of the invention. A kit can include one or more of a genome-targeting nucleic acid, a polynucleotide encoding a genome-targeting nucleic acid, a site-directed polypeptide, a polynucleotide encoding a site-directed polypeptide, and/or any nucleic acid or proteinaceous molecule necessary to carry out the embodiments of the methods of the invention, or any combination thereof.

In some embodiments, a kit comprises: (1) a vector comprising a nucleotide sequence encoding a genome-targeting nucleic acid, and (2) a vector comprising a nucleotide sequence encoding the site-directed polypeptide or the site-directed polypeptide and (3) a reagent for reconstitution and/or dilution of the vector(s) and or polypeptide.

In some embodiments, a kit comprises: (1) a vector comprising (i) a nucleotide sequence encoding a genome-targeting nucleic acid, and (ii) a nucleotide sequence encoding the site-directed polypeptide and (2) a reagent for reconstitution and/or dilution of the vector.

In some embodiments of any of the above kits, the kit comprises a single-molecule guide genome-targeting nucleic acid. In some embodiments of any of the above kits, the kit comprises a double-molecule genome-targeting nucleic acid. In some embodiments of any of the above kits, the kit comprises two or more double-molecule guides or single-molecule guides. In some embodiments, the kits comprise a vector that encodes the nucleic acid targeting nucleic acid.

In some embodiments of any of the above kits, the kit can further comprise a polynucleotide to be inserted to effect the desired genetic modification.

Components of a kit may be in separate containers, or combined in a single container.

In some embodiments, a kit described above further comprises one or more additional reagents, where such additional reagents are selected from a buffer, a buffer for introducing a polypeptide or polynucleotide into a cell, a wash buffer, a control reagent, a control vector, a control RNA polynucleotide, a reagent for in vitro production of the polypeptide from DNA, adaptors for sequencing and the like. A buffer can be a stabilization buffer, a reconstituting buffer, a diluting buffer, or the like. In some embodiments, a kit can also include one or more components that may be used to facilitate or enhance the on-target binding or the cleavage of DNA by the endonuclease, or improve the specificity of targeting.

In addition to the above-mentioned components, a kit can further include instructions for using the components of the kit to practice the methods. The instructions for practicing the methods are generally recorded on a suitable recording medium. For example, the instructions may be printed on a substrate, such as paper or plastic, etc. The instructions may be present in the kits as a package insert, in the labeling of the container of the kit or components thereof (i.e., associated with the packaging or subpackaging), etc. The instructions can be present as an electronic storage data file present on a suitable computer readable storage medium, e.g. CD-ROM, diskette, flash drive, etc. In some instances, the actual instructions are not present in the kit, but means for obtaining the instructions from a remote source (e.g. via the Internet), can be provided. An example of this embodiment is a kit that includes a web address where the instructions can be viewed and/or from which the instructions can be downloaded. As with the instructions, this means for obtaining the instructions can be recorded on a suitable substrate.

Guide RNA Formulation

Guide RNAs of the invention are formulated with pharmaceutically acceptable excipients such as carriers, solvents, stabilizers, adjuvants, diluents, etc., depending upon the particular mode of administration and dosage form. Guide RNA compositions are generally formulated to achieve a physiologically compatible pH, and range from a pH of about 3 to a pH of about 11, about pH 3 to about pH 7, depending on the formulation and route of administration. In alternative embodiments, the pH is adjusted to a range from about pH 5.0 to about pH 8. In some embodiments, the compositions comprise a therapeutically effective amount of at least one compound as described herein, together with one or more pharmaceutically acceptable excipients. Optionally, the compositions comprise a combination of the compounds described herein, or may include a second active ingredient useful in the treatment or prevention of bacterial growth (for example and without limitation, anti-bacterial or anti-microbial agents), or may include a combination of reagents of the invention.

Suitable excipients include, for example, carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants (for example and without limitation, ascorbic acid), chelating agents (for example and without limitation, EDTA), carbohydrates (for example and without limitation, dextrin, hydroxyalkylcellulose, and hydroxyalkylmethylcellulose), stearic acid, liquids (for example and without limitation, oils, water, saline, glycerol and ethanol), wetting or emulsifying agents, pH buffering substances, and the like.

Other Possible Therapeutic Approaches

It is preferable to use CRISPR endonucleases, such as Cas9, in the methods described herein. However, the teachings described herein, such as therapeutic target sites, could be applied to other forms of endonucleases, such as ZFNs, TALENs, HEs, or MegaTALs.

Zinc Finger Nucleases

Zinc finger nucleases (ZFNs) are modular proteins comprised of an engineered zinc finger DNA binding domain linked to the catalytic domain of the type II endonuclease FokI. Because FokI functions only as a dimer, a pair of ZFNs must be engineered to bind to cognate target "half-site" sequences on opposite DNA strands and with precise spacing between them to enable the catalytically active FokI dimer to form. Upon dimerization of the FokI domain, which itself has no sequence specificity per se, a DNA double-strand break is generated between the ZFN half-sites as the initiating step in genome editing.

The DNA binding domain of each ZFN is typically comprised of 3-6 zinc fingers of the abundant Cys2-His2 architecture, with each finger primarily recognizing a triplet of nucleotides on one strand of the target DNA sequence, although cross-strand interaction with a fourth nucleotide also can be important. Alteration of the amino acids of a finger in positions that make key contacts with the DNA alters the sequence specificity of a given finger. Thus, a four-finger zinc finger protein will selectively recognize a 12 bp target sequence, where the target sequence is a composite of the triplet preferences contributed by each finger, although triplet preference can be influenced to varying degrees by neighboring fingers. An important aspect of ZFNs is that they can be readily re-targeted to almost any genomic address simply by modifying individual fingers, although considerable expertise is required to do this well. In most applications of ZFNs, proteins of 4-6 fingers are used, recognizing 12-18 bp respectively. Hence, a pair of ZFNs will typically recognize a combined target sequence of 24-36 bp, not including the 5-7 bp spacer between half-sites. A target sequence of this length is likely to be unique in the human genome, assuming repetitive sequences or gene homologs are excluded during the design process. Nevertheless, the ZFN protein-DNA interactions are not absolute in their specificity so off-target binding and cleavage events do occur, either as a heterodimer between the two ZFNs, or as a homodimer of one or the other of the ZFNs. The latter possibility has been effectively eliminated by engineering the dimerization interface of the FokI domain to create "plus" and "minus" variants, also known as obligate heterodimer variants, which can only dimerize with each other, and not with themselves. Forcing the obligate heterodimer prevents formation of the homodimer. This has greatly enhanced specificity of ZFNs, as well as any other nuclease that adopts these FokI variants.

A variety of ZFN-based systems have been described in the art, modifications thereof are regularly reported, and numerous references describe rules and parameters that are used to guide the design of ZFNs; see, e.g., Segal et al., *Proc Natl Acad Sci USA* 96(6):2758-63 (1999); Dreier B et al., *J Mol Biol.* 303(4):489-502 (2000); Liu Q et al., *J Biol Chem.* 277(6):3850-6 (2002); Dreier et al., *J Biol Chem* 280(42): 35588-97 (2005); and Dreier et al., *J Biol Chem.* 276(31): 29466-78 (2001).

Transcription Activator-Like Effector Nucleases (TALENs)

TALENs represent another format of modular nucleases whereby, as with ZFNs, an engineered DNA binding domain is linked to the FokI nuclease domain, and a pair of TALENs operate in tandem to achieve targeted DNA cleavage. The major difference from ZFNs is the nature of the DNA binding domain and the associated target DNA sequence recognition properties. The TALEN DNA binding domain derives from TALE proteins, which were originally described in the plant bacterial pathogen *Xanthomonas* sp. TALEs are comprised of tandem arrays of 33-35 amino acid repeats, with each repeat recognizing a single basepair in the target DNA sequence that is typically up to 20 bp in length, giving a total target sequence length of up to 40 bp. Nucleotide specificity of each repeat is determined by the repeat variable diresidue (RVD), which includes just two amino acids at positions 12 and 13. The bases guanine, adenine, cytosine and thymine are predominantly recognized by the four RVDs: Asn-Asn, Asn-Ile, His-Asp and Asn-Gly, respectively. This constitutes a much simpler recognition code than for zinc fingers, and thus represents an advantage over the latter for nuclease design. Nevertheless, as with ZFNs, the protein-DNA interactions of TALENs are not absolute in their specificity, and TALENs have also benefitted from the use of obligate heterodimer variants of the FokI domain to reduce off-target activity.

Additional variants of the FokI domain have been created that are deactivated in their catalytic function. If one half of either a TALEN or a ZFN pair contains an inactive FokI domain, then only single-strand DNA cleavage (nicking) will occur at the target site, rather than a DSB. The outcome is comparable to the use of CRISPR/Cas9 "nickase" mutants in which one of the Cas9 cleavage domains has been deactivated. DNA nicks can be used to drive genome editing by HDR, but at lower efficiency than with a DSB. The main benefit is that off-target nicks are quickly and accurately repaired, unlike the DSB, which is prone to NHEJ-mediated mis-repair.

A variety of TALEN-based systems have been described in the art, and modifications thereof are regularly reported; see, e.g., Boch, *Science* 326(5959):1509-12 (2009); Mak et al., *Science* 335(6069):716-9 (2012); and Moscou et al., *Science* 326(5959):1501 (2009). The use of TALENs based on the "Golden Gate" platform has been described by multiple groups; see, e.g., Cermak et al., *Nucleic Acids Res.* 39(12):e82 (2011); Li et al., *Nucleic Acids Res.* 39(14):6315-25(2011); Weber et al., *PLoS One.* 6(2):e16765 (2011); Wang et al., *J Genet Genomics* 41(6):339-47, Epub 2014 May 17 (2014); and Cermak T et al., *Methods Mol Biol.* 1239:133-59 (2015).

Homing Endonucleases

Homing endonucleases (HEs) are sequence-specific endonucleases that have long recognition sequences (14-44 base pairs) and cleave DNA with high specificity—often at sites unique in the genome. There are at least six known families of HEs as classified by their structure, including LAGLIDADG, GIY-YIG, His-Cis box, H—N—H, PD-(D/E)xK, and Vsr-like that are derived from a broad range of hosts, including eukarya, protists, bacteria, archaea, cyanobacteria and phage. As with ZFNs and TALENs, HEs can be used to create a DSB at a target locus as the initial step in genome editing. In addition, some natural and engineered HEs cut only a single strand of DNA, thereby functioning as site-specific nickases. The large target sequence of HEs and the specificity that they offer have made them attractive candidates to create site-specific DSBs.

A variety of HE-based systems have been described in the art, and modifications thereof are regularly reported; see, e.g., the reviews by Steentoft et al., *Glycobiology* 24(8):663-80 (2014); Belfort and Bonocora, *Methods Mol Biol.* 1123: 1-26 (2014); Hafez and Hausner, *Genome* 55(8):553-69 (2012); and references cited therein.

MegaTAL/Tev-mTALEN/MegaTev

As further examples of hybrid nucleases, the MegaTAL platform and Tev-mTALEN platform use a fusion of TALE DNA binding domains and catalytically active HEs, taking advantage of both the tunable DNA binding and specificity of the TALE, as well as the cleavage sequence specificity of the HE; see, e.g., Boissel et al., *NAR* 42: 2591-2601 (2014); Kleinstiver et al., *G3* 4:1155-65 (2014); and Boissel and Scharenberg, *Methods Mol. Biol.* 1239: 171-96 (2015).

In a further variation, the MegaTev architecture is the fusion of a meganuclease (Mega) with the nuclease domain derived from the GIY-YIG homing endonuclease I-TevI (Tev). The two active sites are positioned ~30 bp apart on a DNA substrate and generate two DSBs with non-compatible cohesive ends; see, e.g., Wolfs et al., *NAR* 42, 8816-29 (2014). It is anticipated that other combinations of existing nuclease-based approaches will evolve and be useful in achieving the targeted genome modifications described herein.

dCas9-FokI and Other Nucleases

Combining the structural and functional properties of the nuclease platforms described above offers a further approach to genome editing that can potentially overcome some of the inherent deficiencies. As an example, the CRISPR genome editing system typically uses a single Cas9 endonuclease to create a DSB. The specificity of targeting is driven by a 20 nucleotide sequence in the guide RNA that undergoes Watson-Crick base-pairing with the target DNA (plus an additional 2 bases in the adjacent NAG or NGG PAM sequence in the case of Cas9 from *S. aureus*). Such a sequence is long enough to be unique in the human genome, however, the specificity of the RNA/DNA interaction is not absolute, with significant promiscuity sometimes tolerated, particularly in the 5' half of the target sequence, effectively reducing the number of bases that drive specificity. One solution to this has been to completely deactivate the Cas9 catalytic function—retaining only the RNA-guided DNA binding function—and instead fusing a FokI domain to the deactivated Cas9; see, e.g., Tsai et al., *Nature Biotech* 32: 569-76 (2014); and Guilinger et al., *Nature Biotech.* 32: 577-82 (2014). Because FokI must dimerize to become catalytically active, two guide RNAs are required to tether two Cas9-FokI fusions in close proximity to form the dimer and cleave DNA. This essentially doubles the number of bases in the combined target sites, thereby increasing the stringency of targeting by CRISPR-based systems.

As further example, fusion of the TALE DNA binding domain to a catalytically active HE, such as I-TevI, takes advantage of both the tunable DNA binding and specificity of the TALE, as well as the cleavage sequence specificity of I-TevI, with the expectation that off-target cleavage may be further reduced.

Other Definitions

The term "comprising" or "comprises" is used in reference to compositions, methods, and respective component(s) thereof, that are essential to the invention, yet open to the inclusion of unspecified elements, whether essential or not.

The term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

The singular forms "a," "an," and "the" include plural references, unless the context clearly dictates otherwise.

Certain numerical values presented herein are preceded by the term "about." The term "about" is used to provide literal support for the numerical value the term "about" precedes, as well as a numerical value that is approximately the numerical value, that is the approximating unrecited numerical value may be a number which, in the context it is presented, is the substantial equivalent of the specifically recited numerical value.

When a range of numerical values is presented herein, it is contemplated that each intervening value between the lower and upper limit of the range, the values that are the upper and lower limits of the range, and all stated values with the range are encompassed within the disclosure. All the possible sub-ranges within the lower and upper limits of the range are also contemplated by the disclosure.

EXAMPLES

The invention will be more fully understood by reference to the following examples, which provide illustrative non-limiting embodiments of the invention.

The examples describe the use of the CRISPR system as an illustrative genome editing technique to repair mutations in the titin gene, leading to permanent correction of mutations in the genomic locus, or expression at a heterologous locus, that restore titin activity. The repair of the mutations by genome editing represents a novel therapeutic strategy for the potential amelioration of cardiomyopathies or other titinopathies, as described and illustrated herein.

Example 1

An in vitro model of repair by CRISPR/Cas9 genome editing of a titin truncating mutation was developed based on mutations identified in a patent with centronuclear myopathy as well as dilated cardiomyopathy [Ceyhan-Birosy, Neurology, 81(14): 1205-1214 (2013)]. The patient's fibroblasts had a G>C mutation in titin exon 219 (mutation c.32854G>C) located at a splice site that leads to truncation of the C-terminus of titin and loss of the calpain3 binding site and the titin kinase domain. Another truncating mutation was identified in intron 242 (mutation c. 37112G>A).

Repair Strategy 1

As a first exemplary repair strategy, the c.32854G>C titin mutation was targeted for repair using *S. aureus* Cas9 and one of four different gRNAs to insert a wild-type donor template that corrected the mutation.

Regions of the titin human gene near the exon 219 mutation were scanned for cleavage sites. Since the Cas9 endonuclease from *S. aureus* was being used for genome editing, each region was scanned for the *S. aureus* protospacer adjacent motif (PAM) having the sequence NNGRRT. A number of 21 bp spacer sequences targeting the titin DNA adjacent a PAM were designed for incorporation in sgRNAs. FIG. 2 shows the PAMs chosen and the 21 bp spacer sequence (of each gRNA) that is complementary to the titin DNA target sequence selected. The position number given in FIG. 2 corresponds to the 3' end of the guide sequence that is complementary to the titin genomic sequence. The specificity score was determined using the software available on DeskGen.com. The higher the specificity score, the more specific the gRNA is predicted to be to the titin genome.

Figure 3:
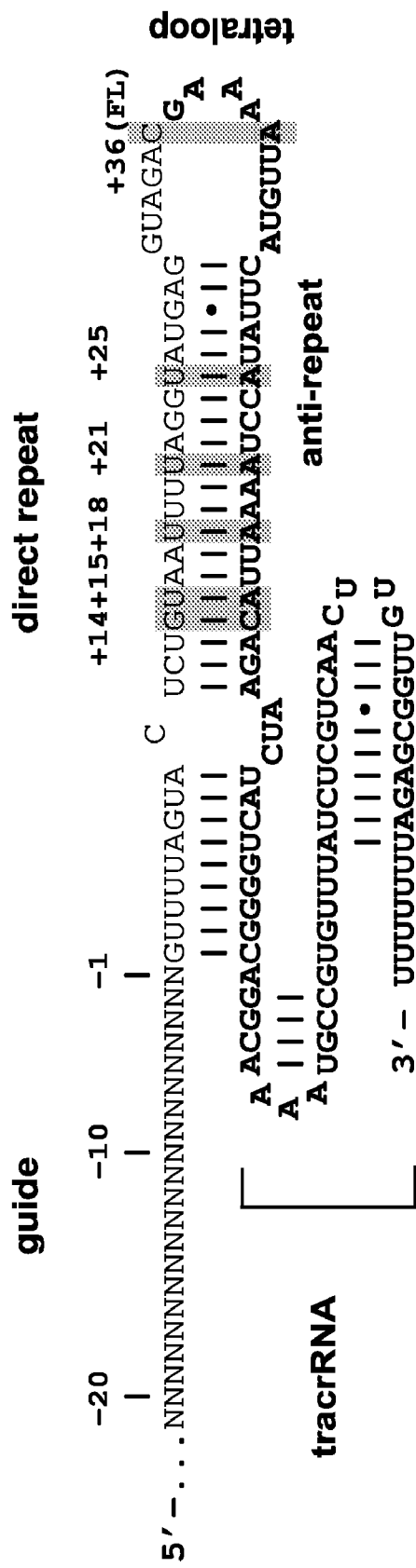
FIG. 3 shows the gRNA structure and sequence, wherein one of the specific spacer sequences replaces the 5' nucleotides shown as "N"s and the remaining nucleotides are the same among the gRNAs.

To express each sgRNA and *S. aureus* Cas9, the Addgene (Cambridge, Mass.) plasmid #61591 (pX601-AAV-CMV:: NLS-SaCas9-NLS-3xHA-bGHpA;U6::BsaI-sgRNA) [Ran et al., supra] was used. The plasmid encodes a single vector AAV-Cas9 system containing Cas9 from Staphylococcus aureus (SaCas9) and its sgRNA. DNA encoding one of 21 bp spacer sequences was inserted in the appropriate location in the plasmid so that the spacer sequence was expressed as the 5' end of the sgRNA. See FIG. 3 showing the gRNA structure and sequence, wherein one of the specific spacer sequences replaces the 5' nucleotides shown as "N"s and the remaining nucleotides are the same among the gRNAs.

Patient fibroblasts were co-transfected via electroporation with the SaCas9/gRNA plasmid and a wild-type donor template for repair of the c.32854G>A mutation. The fibroblast cells were trypsinized and pelleted for 5 min at 1500×g. The cells were then washed with PBS and centrifuged. The cells were then resuspended in 1-2 mL RPMI (no serum or antibiotics) and counted. For electroporation, the cells (200 ul-5×10$^5$ cells) were placed in a 0.2 cm cuvette with 10 ug plasmid (no more than 15 ul, preferably in water) and template DNA and electroporated at 250V, 500 uF. 800-900 ul growth media (at least 20% fbs) was added and cells were plated in a 6 or 12-well plate.

| Media | Volume | Cell Count | Cuvette | Conditions | DNA |
|---|---|---|---|---|---|
| RPMI | 200 ul | $5 \times 10^5$ | 0.2 cm | 250 V, 500 uF | 10 ug |
| RPMI | 500 ul | $1 \times 10^6$ | 0.4 cm | 250 V, 500 uF | 10-20 ug |

The donor template (FIG. 4) was a single-stranded oligonucleotide 100 nucleotides (nt) in length, which included homology arms and spanned the 21 nt target sequence but includes a mutated PAM sequence to decrease the probability of Cas9 cutting the donor template.

To demonstrate gene correction in the patient fibroblasts, the treated cells were verified to have gene modification activity by the T7E1 assay 48 hours after transfection. PCR products were run on a 0.7% ethidium bromide stained agarose gel. The results are shown in FIG. 5, wherein percent indels represents the sum of all NHEJ mediated insertions/deletions for all samples. The T7E1 assay demonstrated 3-10% efficiency in the patient fibroblasts.

Repair Strategy 2

As a second exemplary repair strategy, the c.32854G>C titin mutation was targeted for repair using *S. aureus* Cas9 and a pair of sgRNAs to remove (or "skip") exon 219 containing the mutation to restore the wild-type titin reading frame.

Regions of the two introns (intron 218 and intron 219) flanking exon 219 were scanned for cleavage sites. Again, since the Cas9 endonuclease from *S. aureus* was being used for genome editing, each region was scanned for the *S. aureus* PAM having the sequence NNGRRT. A 21 bp spacer sequence was designed to target a DNA sequence adjacent a PAM in each intron.

The 21 bp spacer sequences are then each incorporated in a sgRNA (for example, as described for Strategy 1). FIG. 6 shows the PAMs chosen and the 21 bp spacer sequence (of each gRNA) that is complementary to the respective intron DNA target sequence selected. 21 bp spacer sequences that could alternatively be used in one or both members of a pair of sgRNAs to delete exon 219, are shown in FIG. 7.

The two sgRNAs, one targeting intron 218 and the other targeting intron 219, are then used along with *S. aureus* Cas9 to delete titin exon 219 in a subject's cell.

Repair Strategy 3

As a third exemplary repair strategy, the c.37112G>A titin mutation was targeted for repair using *S. aureus* Cas9 and one of three different gRNAs to insert a wild-type donor template that corrected the mutation.

Regions of the intron 242 were scanned for cleavage sites. Again, since the Cas9 endonuclease from *S. aureus* was being used for genome editing, each region was scanned for the *S. aureus* PAM having the sequence NNGRRT. A number of 21 bp spacer sequences targeting the titin DNA adjacent a PAM were designed for incorporation in sgRNAs. FIG. 8 shows the PAMs chosen and the 21 bp spacer sequence (of each gRNA) that is complementary to the titin DNA target sequence selected.

The 21 bp spacer sequences are then each incorporated in a sgRNA (for example, as described for Strategy 1).

One of the sgRNAs targeting intron 24 is then used along with *S. aureus* Cas9 and the wild-type donor template to repair the mutation in intron 242 in a subject's cell.

Repair Strategy 4

As a fourth exemplary repair strategy, a c.4362insAT mutation in titin exon 326 was targeted for repair using *S. aureus* Cas9 and a pair of sgRNAs to remove (or "skip") exon 326 containing the mutation to restore the wild-type titin reading frame.

Regions of the two introns (intron 325-327) flanking exon 326 were scanned for cleavage sites. Again, since the Cas9 endonuclease from *S. aureus* was being used for genome editing, each region was scanned for the *S. aureus* PAM having the sequence NNGRRT. A 21 bp spacer sequence was designed to target a DNA sequence adjacent a PAM in each intron.

FIG. 9 shows two sets of the PAMs selected (one set for each intron) and the 21 bp spacer sequence (of each gRNA) that is complementary to the respective intron DNA target sequence selected. Pairs of 21 bp spacer sequences (one from each set per pair) are then each incorporated in a sgRNA (for example, as described for Strategy 1).

The two sgRNAs, one targeting intron 325 and the other targeting intron 327, are then used along with *S. aureus* Cas9 to delete titin exon 326 in a subject's cell.

Example 2

The SaCas9/gRNA cassettes from plasmids generated for the experiments described in Example 1 will be packaged in rAAV.rh74. The resulting rAAV are referred to generically as rAAV.rh74.Cas9TTN in Example 4 below.

A modified cross-packaging approach previously reported in Rodino-Klapac et al. *J Transl Med.* 5: 45 (2007) is used to produce the rAAV vectors. Here, a triple transfection method with $CaPO_4$ precipitation in HEK293 cells allows for AAV2 ITRs to be packaged into a different AAV capsid serotype [Rabinowitz et al., J. Virol., 76(2): 791-801 (2002) and Grieger et al., Nat. Protoc., 1(3): 1412-1428 (2006)]. The production plasmids are: (i) pAAV.Cas9.TTN, (ii) rep2-caprh.74 modified AAV helper plasmids encoding cap serotype 8-like isolate rh.74, and (iii) an adenovirus type 5 helper plasmid (pAdhelper) expressing adenovirus E2A, E4 ORF6, and VA I/II RNA genes. Vectors are purified and encapsidated vector genome (vg) titer (utilizing a Prism 7500 Taqman detector system (PE Applied Biosystems, Carlsbad, Calif.)) is determined as previously described [Clark et al., Hum. Gene. Ther., 10(6): 1031-1039 (1999)].

Example 3

In a mouse model comprising titin mutations, rAAV.rh74.Cas9TTN will be delivered using an intracoronary approach and a dose escalation paradigm will be utilized to establish proper dose to achieve expression in cardiomyocytes.

The model involves the induction of myocardial ischemia in the mouse heart through a modified version coronary artery ligation [Gao et al., Methods in Molecular Therapy. 2013; 1037: 299-311; Gao et al., Circ Res.; 107(12): 1445-1453]. This new approach has improved survival rate, decreased recovery time and lower incidence of cardiac arrhythmia than traditional methods for entering the chest (thoracotomy or sternotomy). Delivery of AAV.rh74.CMV.eGFP by an intracoronary approach in the model results in eGFP expression restricted to the heart with high transduction efficiency.

Model 1: DCM Model Targeting Exon 326

The CRISPR MIT platform (crispr.mit.edu) was used to design truncated sgRNAs (5'-NNGRRT-3') [Doench et al., *Nature Biotechnology,* 34(2):184-91 (2016)] targeting the human genomic sequence around exon 326 in order to insert the 2 base pair insertion (c.43628insAT) to knock in the defined human DCM mutation. This mutation was originally identified in two large kindred cohorts in the UK, however, has been identified in approximately 15% of the TTN DCM population [Gramlich et al., *Journal of Molecular and Cellular Cardiology*, 47(3):352-358 (2009); Zhou et al., *BioMed Research International*, 2015:163564 (2015); Gramlich et al., *EMBO Molecular Medicine*, 7(5):562-576 (2015); Peled et al., *International Journal of Cardiology*, 171(1):24-30 (2014); Gerull et al., *Nature Genetics*, 30(2): 201-204 (2002)]. Additionally, the literature has identified a potential internal promoter at the junction of exon 239 and 240 in TTN which delineates more pathogenic mutations in patients with TTN [Zou et al., eLife, 4:e09406 (2015)]. Those patients with mutations distal to the internal promoter have more severe cases of DCM. Therefore, an accessible mouse model to study therapeutic interventions was designed.

The sequences of the sgRNAs were aligned to the human genome to verify the exclusion of single nucleotide polymorphisms (SNPs) [Tsai et al., Nature Biotechnology, 33(2): 187-197 (2015)]. The *Staphlycoccus aureus* derived Cas9 mRNA is purified and resuspended in EmbryoMax injection buffer (Temecula). The sgRNA is generated by in vitro transcription as previously published [Mashiko et al., *Scientific Reports*, 3:3355 2013); Horii et al., *Scientific Reports*, 4:4513 (2014)]. Briefly, after PCR purification, the template is used for in vitro transcription using the T7 transcription kit (Life Technologies). Female BL6 mice of approximately 6 weeks of age are superovulated with PMS (pregnant mare serum) and hCG (human chorionic gonadotropin) (Horii et al., supra). Subsequently, they are mated with male BL6 mice and zygotes are isolated from the ampullae of the superovulated mice. sgRNAs and mRNA of saCas9 are co-injected into the pronucleus using a microscope with micromanipulators. Approximately 20-30 zygotes are reimplanted per pseudopregnant mouse immediately after injection.

All procedures performed on animals are in accordance with IACUC (AR08-00017; IBS00000202). Further breeding with cross littermates will be utilized to determine exon 326 insertion of 2 base pair AT into the location of c.43628 TTN and successful germline transmission of the knock-in mutation.

Another mouse model is described in the literature and differs in that it was generated using a targeting vector including the human TTN mutation c.43628insAT followed by a neomycin resistance cassette with a poly-adenylation signal (Gramlich et al. 2009, supra). The mutation was introduced into mouse ES cells by homologous recombination. In the Gramlich mouse model, the homozygous offspring were embryonically lethal with no cardiac formation whatsoever. The heterozygous offspring developed dilated cardiomyopathy and had impaired cardiac function upon stress induction.

Model 2: Skeletal Myopathy Model Targeting Exon 219

Additionally, a TTN skeletal muscle myopathy model was designed to incorporate a published mutation that affects skeletal muscle and presents as a centronuclear myopathy (c.32854G>C) [Ceyhan-Birsoy et al., *Neurology*, 81(14) 1205-14 (2013)]. The findings in the clinical population include increased central nuclei, truncation of the protein, loss of binding for calpain-3, sarcomeric disorganization, increased connective tissue and regions devoid of mitochondria. The clinical presentations of this patient include generalized muscle weakness, respiratory weakness, and possible cardiac involvement. The mutation is located at a conserved splice site and produces splicing defects and truncated titin protein [Ceyhan-Birsoy et al., supra; Foye, *Narrative Inquiry in Bioethics*, 5(3): 206-208 (2015)]. No similar mouse model is available in the literature. The TTN skeletal muscle myopathey model described here is useful to delineate the severity of disease associated with various types of mutations and locations of mutations in TTN and provide a therapeutic approach. To generate the model mice, Cas9 genome editing is used to knock in the base pair mutation and truncate the TTN protein and establish the phenotype and functional deficits in skeletal and cardiac tissue.

The CRISPR MIT platform was used to design truncated sgRNAs (5'-NNGRRT-3') using the human genomic sequence within exon 219. The sequences of the sgRNAs were aligned to the human genome to verify the exclusion of sSNPs (Tsai et al., supra). The *Staphlycoccus aureus* derived Cas9 mRNA are purified and resuspended in EmbryoMax injection buffer (Temecula). The sgRNA is generated by in vitro transcription as previously published (Machiko et al., supra; Horii et al., supra). Briefly, after PCR purification, the template is used for in vitro transcription using the T7 transcription kit (Life Technologies). Female BL6 mice of approximately 6 weeks of age are superovulated with PMS (pregnant mare serum) and hCG (human chorionic gonadotropin) (Horii et al., supra). Subsequently, they are mated with male BL6 mice and zygotes are isolated from the ampullae of the superovulated mice. sgRNAs and mRNA of saCas9 are co-injected into the pronucleus using a microscope with micromanipulators. Approximately 20-30 zygotes are reimplanted per pseudopregnant mouse immediately after injection.

All procedures performed on animals are in accordance with IACUC (AR08-00017; IBS00000202). Further breeding with cross littermates is utilized to determine exon 219 insertion of c.32854G>C and successful germline transmission of the knock-in mutation.

Delivery of AAV.rh74.Cas9TTN

Mice with one or more titin gene mutations (which mutations may be introduced by CRISPR/Cas9 genome editing as described for Models 1 and 2) are anesthetized with 2.5% isoflurane in 2 L/min oxygen. A small incision in the skin on the left chest is made to expose the chest muscles. The pectoral major and minor muscles are dissected to expose the further intercostal space. Mosquito forceps are pushed through the fourth intercostal space to penetrate the intercostal muscle, peural membrane and pericardium. Holding the forceps open, the heart is externalized to view the apex. Using a 30G needle, AAVrh.74.SaCas9/TTN is infused into the lumen of the left ventricle. After delivery, the needle is removed and the heart is put back into the chest followed by manual evacuation of air and closure of the skin with a single suture. Intracoronary delivery routes have been shown to be superior to other methods of delivery (e.g. intravenous, intraperitoneal) in terms of uniformity of cell distribution, myocyte regeneration, and amount of viable tissue in an ischemic region of the myocardium [Li, Basic Research in Cardiology. 2011; 106(5):849-864]. In previous studies, the procedure was safe with very low mortality [Gao et al., supra].

The study endpoint is at 3 months and outcome measurements include quantification of titin expression and biodistribution/quantification of vg copies in all skeletal and cardiac muscles. If the initial dosed cohorts do not result in >50% full length titin, then further dose escalation will continue. Finally, off target analyses are performed via PCR based assays to detect genomic translocations and off target activity taking into account the NNGRRT specific protospacer adjacent motif (PAM) that drives SaCas9. In order to evaluate in vivo cardiac function, cardiac systolic and diastolic performance are quantified using echocardiograph with pulse wave Doppler and tissue Doppler imaging. Echocardiographs are used to determine multiple measures of cardiac function including: ejection fraction, fractional shortening, end-diastolic volume, and end-systolic volume. Additionally, wall thickness are measured. Following in life monitoring, mice are necropsied at 12 weeks to evaluate titin expression in the myocardium. Immunofluorescence of titin (Z-disk and C-terminus portions) and cardiac troponin T will demonstrate sarcomeric organization after treatment. Electron microscopy of the myofibrils are used to determine proper alignment after treatment.

Notes Regarding Illustrative Embodiments and Cited Documents

While the present disclosure provides specific embodiments and examples, it is understood that variations and modifications will occur to those skilled in the art. Accordingly, only such limitations as appear in the claims should be placed on the invention.

All documents cited in this application are hereby incorporated by reference in their entirety, with particular attention to the disclosure for which they are referred.

What is claimed is:

1. A method of repairing a mutant titin gene in an isolated human cell comprising introducing into the cell
   (a) a Cas9 endonuclease or a nucleic acid that encodes a Cas9 endonuclease; and
   (b) (i) a nucleic acid encoding a guide ribonucleic acid (gRNA) comprising a spacer sequence having the nucleotide sequence set forth in SEQ ID NO: 19, 23, or 27-41 when the cell has a compound heterozygous mutation in exon 219 of the titin gene;
   (ii) a nucleic acid encoding a gRNA comprising a spacer sequence having the nucleotide sequence set forth in SEQ ID NO: 64, 66, 68, 70, 72, 74, or 76 when the cell has a compound heterozygous mutation in exon 326 of the titin gene;
   (iii) a nucleic acid encoding a gRNA comprising a spacer sequence having the nucleotide sequence set forth in SEQ ID NO: 1, 5, 9, or 13 and a nucleic acid comprising a donor template comprising the nucleotide sequence set forth in SEQ ID NO: 18 when the cell has a compound heterozygous c.32854G>C mutation in exon 219 of the titin gene; or
   (iv) a nucleic acid encoding a gRNA comprising a spacer sequence having the nucleotide sequence set forth in SEQ ID NO: 57, 59, or 61 and a nucleic acid comprising a donor template comprising the nucleotide sequence set forth in SEQ ID NO: 63 when the cell has a compound heterozygous c.37112G>A mutation in intron 242 of the titin gene
   resulting in repair of the mutant titin gene and expression of functional titin in the cell.

2. The method of claim 1, wherein the isolated cell is an isolated heart cell.

3. The method of claim 1, wherein the isolated cell is an isolated cardiac stem cell (CSC) or primary cardiomyocyte.

4. The method of claim 1, wherein the nucleic acid is modified.

5. The method of claim 1, wherein the gRNA is a single-molecule guide RNA (sgRNA).

6. The method of claim 5, wherein the gRNA or the sgRNA is a modified gRNA or modified sgRNA.

7. The method of claim 1, wherein the nucleic acid that encodes the Cas9 endonuclease and the nucleic acid that encodes the gRNA are introduced into the cell in a single vector.

8. The method of claim 1, wherein the nucleic acid that encodes the Cas9 endonuclease and/or the nucleic acid comprising the donor template is/are introduced into the cell in a vector.

9. The method of claim 8, wherein the vector is AAV.

10. The method of claim 1, wherein the nucleic acid that encodes the Cas9 endonuclease, the nucleic acid that encodes the gRNA, and/or the nucleic acid comprising the donor template is/are introduced into the cell in a lipid nanoparticle.

11. The method of claim 1, wherein the nucleic acid that encodes the Cas9 endonuclease introduced into the cell in a lipid nanoparticle and the nucleic acid that encodes the gRNA and/or donor DNA is introduced into the cell in a vector.

* * * * *

```
                              SEQUENCE LISTING

<160> NUMBER OF SEQ ID NOS: 78

<210> SEQ ID NO 1
<211> LENGTH: 21
<212> TYPE: DNA
<213> ORGANISM: Artificial Sequence
<220> FEATURE:
<223> OTHER INFORMATION: Spacer sequence

<400> SEQUENCE: 1
ggaggaggtg ggggtcttgg t                                                   21

<210> SEQ ID NO 2
<211> LENGTH: 6
<212> TYPE: DNA
<213> ORGANISM: Artificial Sequence
<220> FEATURE:
<223> OTHER INFORMATION: Synthetic polynucleotide

<400> SEQUENCE: 2 ttgagt                                                                     6

<210> SEQ ID NO 3
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 3
caccggagga ggtgggggtc ttggt                                               25

<210> SEQ ID NO 4
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 4
aaacaccaag accccacct cctcc                                                25

<210> SEQ ID NO 5
<211> LENGTH: 21
<212> TYPE: DNA
<213> ORGANISM: Artificial Sequence
<220> FEATURE:
<223> OTHER INFORMATION: Spacer sequence

<400> SEQUENCE: 5
ggtggagcag gtggaggagg t                                                   21
```

```
<210> SEQ ID NO 6
<211> LENGTH: 6
<212> TYPE: DNA
<213> ORGANISM: Artificial Sequence
<220> FEATURE:
<223> OTHER INFORMATION: Synthetic polynucleotide

<400> SEQUENCE: 6 gggggt                                                                      6

<210> SEQ ID NO 7
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 7
caccggtgga gcaggtggag gaggt                                                25

<210> SEQ ID NO 8
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 8
aaacacctcc tccacctgct ccacc                                                25

<210> SEQ ID NO 9
<211> LENGTH: 21
<212> TYPE: DNA
<213> ORGANISM: Artificial Sequence
<220> FEATURE:
<223> OTHER INFORMATION: Spacer sequence

<400> SEQUENCE: 9
tggcattttt tacctttaag t                                                    21

<210> SEQ ID NO 10
<211> LENGTH: 6
<212> TYPE: DNA
<213> ORGANISM: Artificial Sequence
<220> FEATURE:
<223> OTHER INFORMATION: Synthetic polynucleotide

<400> SEQUENCE: 10 tggaat                                                                      6

<210> SEQ ID NO 11
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 11
cacctggcat tttttacctt taagt                                                25

<210> SEQ ID NO 12
<211> LENGTH: 25
<212> TYPE: DNA
<213> ORGANISM: Artificial Sequence
<220> FEATURE:
<223> OTHER INFORMATION: Synthetic oligonucleotide
```

```
<400> SEQUENCE: 12
accgtaaaaa atggaaattc acaaa                                           25

<210> SEQ ID NO 13
<211> LENGTH: 21
<212> TYPE: DNA
<213> ORGANISM: Artificial Sequence
<220> FEATURE:
<223> OTHER INFORMATION: Spacer sequence

<400> SEQUENCE: 13
ttttcaggtt caggttcttg a                                               21

<210> SEQ ID NO 14
<211> LENGTH: 6
<212> TYPE: DNA
<213> ORGANISM: Artificial Sequence
<220> FEATURE:
<223> OTHER INFORMATION: Synthetic polynucleotide

<400> SEQUENCE: 14 aagagt                                                                 6

<210> SEQ ID NO 15
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 15
caccttttca ggttcaggtt cttga                                           25

<210> SEQ ID NO 16
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 16
aaaagtccaa gtccaagaac tcaaa                                           25

<210> SEQ ID NO 17
<211> LENGTH: 148
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(21)
<223> OTHER INFORMATION: n is a, c, g, or u

<400> SEQUENCE: 17
nnnnnnnnnn nnnnnnnnnn nguuuuagua cucuguaauu uuagguauga gguagacgaa      60
aauuguacuu auaccuaaaa uuacagaauc uacuaaaaca aggcaaaaug ccguguuuau     120
cucgucaacu uguuggcgag auuuuuuu                                       148

<210> SEQ ID NO 18
<211> LENGTH: 900
<212> TYPE: DNA
<213> ORGANISM: Homo sapiens

<400> SEQUENCE: 18
```

-continued

```
ctttacatat accaaataca acaacatgta tacatcatac agacaagggt aaacatacat    60
ttcataagaa acaacattta cactcggagt aagaatccaa aggtacattg aacatgacaa   120
agagagtaca gttgacaccg aacagaccta cgaaacaaac aacaacaata accacggaaa   180
cgacataaag agtagtagaa acatttccca actataaaaa tacaaaatac aagacacaaa   240
atacaaccta tgaccataat gcatggaatt tttcatttga aacatgaagt atatatatat   300
atatatatat atatatatat atatatatat attaaagata attttatatga tgtataggtg   360 tacgattgta tatgtatatg attgtggaga ctttatgaga aagttcttgg acttggactt   420
ttccaataac tcttcggttt tgagtttggt tctgggggtg gaggaggtgg acgaggtgga   480
ttccttctac acttcctctt ttataaggtt gaatttccat tttttacggt gaaggtttca   540
aaataatcgg acgaagtttg aagataggtc ggtagacttt actacgaacg ttctttacat   600
actgaaaatc ttcacacatg aaagtctgta ctaacatgac actctaacgt atctcgacag   660
agaagacgac ggggtaccaa ggacccaacg aacagtacgg tacggacgac gacgttttca   720
gtctttcatg taactatcgc agtaggccct atagacttac gtccgtgaca ggttaattga   780
aagaaaacac ctcaccccctc tttctcaaaa gactaaagtt tcggactaac gatatgtata   840
gtaacgctag aatacgaatt ccttacatat tctttaggaa cgttctataa aaattataac   900
```

<210> SEQ ID NO 19
<211> LENGTH: 21
<212> TYPE: DNA
<213> ORGANISM: Artificial Sequence
<220> FEATURE:
<223> OTHER INFORMATION: Spacer sequence

<400> SEQUENCE: 19

```
agtatatgta tatgttagca t                                              21
```

<210> SEQ ID NO 20
<211> LENGTH: 6
<212> TYPE: DNA
<213> ORGANISM: Artificial Sequence
<220> FEATURE:
<223> OTHER INFORMATION: Synthetic polynucleotide

<400> SEQUENCE: 20

```
gtggat                                                                6
```

<210> SEQ ID NO 21
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 21

```
caccagtata tgtatatgtt agcat                                          25
```

<210> SEQ ID NO 22
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 22

```
tcatatacat atacaatcgt acaaa                                          25
```

```
<210> SEQ ID NO 23
<211> LENGTH: 21
<212> TYPE: DNA
<213> ORGANISM: Artificial Sequence
<220> FEATURE:
<223> OTHER INFORMATION: Spacer sequence

<400> SEQUENCE: 23
tgcaagcatc atttcagatg g                                             21

<210> SEQ ID NO 24
<211> LENGTH: 6
<212> TYPE: DNA
<213> ORGANISM: Artificial Sequence
<220> FEATURE:
<223> OTHER INFORMATION: Synthetic polynucleotide

<400> SEQUENCE: 24 ctggat                                                               6

<210> SEQ ID NO 25
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 25
cacctgcaag catcatttca gatgg                                         25

<210> SEQ ID NO 26
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 26
acgttcgtag taaagtctac ccaaa                                         25

<210> SEQ ID NO 27
<211> LENGTH: 21
<212> TYPE: DNA
<213> ORGANISM: Artificial Sequence
<220> FEATURE:
<223> OTHER INFORMATION: Spacer sequence

<400> SEQUENCE: 27
agaagattta agtccactgg a                                             21

<210> SEQ ID NO 28
<211> LENGTH: 21
<212> TYPE: DNA
<213> ORGANISM: Artificial Sequence
<220> FEATURE:
<223> OTHER INFORMATION: Spacer sequence

<400> SEQUENCE: 28
gataaagaag atttaagtcc a                                             21

<210> SEQ ID NO 29
<211> LENGTH: 21
<212> TYPE: DNA
<213> ORGANISM: Artificial Sequence
<220> FEATURE:
<223> OTHER INFORMATION: Spacer sequence
```

<400> SEQUENCE: 29
atgaggctca catttacaac a                                              21

<210> SEQ ID NO 30
<211> LENGTH: 21
<212> TYPE: DNA
<213> ORGANISM: Artificial Sequence
<220> FEATURE:
<223> OTHER INFORMATION: Spacer sequence

<400> SEQUENCE: 30
tgatagcgtc atccgggata t                                              21

<210> SEQ ID NO 31
<211> LENGTH: 21
<212> TYPE: DNA
<213> ORGANISM: Artificial Sequence
<220> FEATURE:
<223> OTHER INFORMATION: Spacer sequence

<400> SEQUENCE: 31
gtacaagtta catggaaacc t                                              21

<210> SEQ ID NO 32
<211> LENGTH: 21
<212> TYPE: DNA
<213> ORGANISM: Artificial Sequence
<220> FEATURE:
<223> OTHER INFORMATION: Spacer sequence

<400> SEQUENCE: 32
ttttatgttc tgtgttttat g                                              21

<210> SEQ ID NO 33
<211> LENGTH: 21
<212> TYPE: DNA
<213> ORGANISM: Artificial Sequence
<220> FEATURE:
<223> OTHER INFORMATION: Spacer sequence

<400> SEQUENCE: 33
tgtccaatta actttctttt g                                              21

<210> SEQ ID NO 34
<211> LENGTH: 21
<212> TYPE: DNA
<213> ORGANISM: Artificial Sequence
<220> FEATURE:
<223> OTHER INFORMATION: Spacer sequence

<400> SEQUENCE: 34
ttcttttgtg gagtggggag a                                              21

<210> SEQ ID NO 35
<211> LENGTH: 21
<212> TYPE: DNA
<213> ORGANISM: Artificial Sequence
<220> FEATURE:
<223> OTHER INFORMATION: Spacer sequence

<400> SEQUENCE: 35
aagtacattg atagcgtcat c                                              21

<210> SEQ ID NO 36

```
<211> LENGTH: 21
<212> TYPE: DNA
<213> ORGANISM: Artificial Sequence
<220> FEATURE:
<223> OTHER INFORMATION: Spacer sequence

<400> SEQUENCE: 36
tcttctgctg ccccatggtt c                                              21

<210> SEQ ID NO 37
<211> LENGTH: 21
<212> TYPE: DNA
<213> ORGANISM: Artificial Sequence
<220> FEATURE:
<223> OTHER INFORMATION: Spacer sequence

<400> SEQUENCE: 37
atcattgcga tcttatgctt a                                              21

<210> SEQ ID NO 38
<211> LENGTH: 21
<212> TYPE: DNA
<213> ORGANISM: Artificial Sequence
<220> FEATURE:
<223> OTHER INFORMATION: Spacer sequence

<400> SEQUENCE: 38
gtatttctca tcatctttgt a                                              21

<210> SEQ ID NO 39
<211> LENGTH: 21
<212> TYPE: DNA
<213> ORGANISM: Artificial Sequence
<220> FEATURE:
<223> OTHER INFORMATION: Spacer sequence

<400> SEQUENCE: 39
cagtgcctgc attcagatat c                                              21

<210> SEQ ID NO 40
<211> LENGTH: 21
<212> TYPE: DNA
<213> ORGANISM: Artificial Sequence
<220> FEATURE:
<223> OTHER INFORMATION: Spacer sequence

<400> SEQUENCE: 40
ctcatgtcaa ctgtggcttg t                                              21

<210> SEQ ID NO 41
<211> LENGTH: 21
<212> TYPE: DNA
<213> ORGANISM: Artificial Sequence
<220> FEATURE:
<223> OTHER INFORMATION: Spacer sequence

<400> SEQUENCE: 41
aaccatatac atttcaagag a                                              21

<210> SEQ ID NO 42
<211> LENGTH: 6
<212> TYPE: DNA
<213> ORGANISM: Artificial Sequence
<220> FEATURE:
<223> OTHER INFORMATION: Synthetic polynucleotide

<400> SEQUENCE: 42
```

```
ttgaat                                                              6

<210> SEQ ID NO 43
<211> LENGTH: 6
<212> TYPE: DNA
<213> ORGANISM: Artificial Sequence
<220> FEATURE:
<223> OTHER INFORMATION: Synthetic polynucleotide

<400> SEQUENCE: 43 ctggat                                                              6

<210> SEQ ID NO 44
<211> LENGTH: 6
<212> TYPE: DNA
<213> ORGANISM: Artificial Sequence
<220> FEATURE:
<223> OTHER INFORMATION: Synthetic polynucleotide

<400> SEQUENCE: 44 aagaat                                                              6

<210> SEQ ID NO 45
<211> LENGTH: 6
<212> TYPE: DNA
<213> ORGANISM: Artificial Sequence
<220> FEATURE:
<223> OTHER INFORMATION: Synthetic polynucleotide

<400> SEQUENCE: 45 ctgaat                                                              6

<210> SEQ ID NO 46
<211> LENGTH: 6
<212> TYPE: DNA
<213> ORGANISM: Artificial Sequence
<220> FEATURE:
<223> OTHER INFORMATION: Synthetic polynucleotide

<400> SEQUENCE: 46 aagaat                                                              6

<210> SEQ ID NO 47
<211> LENGTH: 6
<212> TYPE: DNA
<213> ORGANISM: Artificial Sequence
<220> FEATURE:
<223> OTHER INFORMATION: Synthetic polynucleotide

<400> SEQUENCE: 47 ttggat                                                              6

<210> SEQ ID NO 48
<211> LENGTH: 6
<212> TYPE: DNA
<213> ORGANISM: Artificial Sequence
<220> FEATURE:
<223> OTHER INFORMATION: Synthetic polynucleotide

<400> SEQUENCE: 48 tggagt                                                              6

<210> SEQ ID NO 49
<211> LENGTH: 6
<212> TYPE: DNA
```

```
<213> ORGANISM: Artificial Sequence
<220> FEATURE:
<223> OTHER INFORMATION: Synthetic polynucleotide

<400> SEQUENCE: 49 aagagt                                                                     6

<210> SEQ ID NO 50
<211> LENGTH: 6
<212> TYPE: DNA
<213> ORGANISM: Artificial Sequence
<220> FEATURE:
<223> OTHER INFORMATION: Synthetic polynucleotide

<400> SEQUENCE: 50 cgggat                                                                     6

<210> SEQ ID NO 51
<211> LENGTH: 6
<212> TYPE: DNA
<213> ORGANISM: Artificial Sequence
<220> FEATURE:
<223> OTHER INFORMATION: Synthetic polynucleotide

<400> SEQUENCE: 51 ctgggt                                                                     6

<210> SEQ ID NO 52
<211> LENGTH: 6
<212> TYPE: DNA
<213> ORGANISM: Artificial Sequence
<220> FEATURE:
<223> OTHER INFORMATION: Synthetic polynucleotide

<400> SEQUENCE: 52 aggaat                                                                     6

<210> SEQ ID NO 53
<211> LENGTH: 6
<212> TYPE: DNA
<213> ORGANISM: Artificial Sequence
<220> FEATURE:
<223> OTHER INFORMATION: Synthetic polynucleotide

<400> SEQUENCE: 53 aagggt                                                                     6

<210> SEQ ID NO 54
<211> LENGTH: 6
<212> TYPE: DNA
<213> ORGANISM: Artificial Sequence
<220> FEATURE:
<223> OTHER INFORMATION: Synthetic polynucleotide

<400> SEQUENCE: 54 ccggat                                                                     6

<210> SEQ ID NO 55
<211> LENGTH: 6
<212> TYPE: DNA
<213> ORGANISM: Artificial Sequence
<220> FEATURE:
<223> OTHER INFORMATION: Synthetic polynucleotide

<400> SEQUENCE: 55 ctggat                                                                     6
```

<210> SEQ ID NO 56
<211> LENGTH: 6
<212> TYPE: DNA
<213> ORGANISM: Artificial Sequence
<220> FEATURE:
<223> OTHER INFORMATION: Synthetic polynucleotide

<400> SEQUENCE: 56 aagaat                                                                  6

<210> SEQ ID NO 57
<211> LENGTH: 21
<212> TYPE: DNA
<213> ORGANISM: Artificial Sequence
<220> FEATURE:
<223> OTHER INFORMATION: Spacer sequence

<400> SEQUENCE: 57
ggagctgtaa gagaatgtca t                                                21

<210> SEQ ID NO 58
<211> LENGTH: 6
<212> TYPE: DNA
<213> ORGANISM: Artificial Sequence
<220> FEATURE:
<223> OTHER INFORMATION: Synthetic polynucleotide

<400> SEQUENCE: 58 cagaat                                                                  6

<210> SEQ ID NO 59
<211> LENGTH: 21
<212> TYPE: DNA
<213> ORGANISM: Artificial Sequence
<220> FEATURE:
<223> OTHER INFORMATION: Spacer sequence

<400> SEQUENCE: 59
attccacatg aggagctgta a                                                21

<210> SEQ ID NO 60
<211> LENGTH: 6
<212> TYPE: DNA
<213> ORGANISM: Artificial Sequence
<220> FEATURE:
<223> OTHER INFORMATION: Synthetic polynucleotide

<400> SEQUENCE: 60 gagaat                                                                  6

<210> SEQ ID NO 61
<211> LENGTH: 21
<212> TYPE: DNA
<213> ORGANISM: Artificial Sequence
<220> FEATURE:
<223> OTHER INFORMATION: Spacer sequence

<400> SEQUENCE: 61
attctcttac agctcctcat g                                                21

<210> SEQ ID NO 62
<211> LENGTH: 6
<212> TYPE: DNA
<213> ORGANISM: Artificial Sequence
<220> FEATURE:

<223> OTHER INFORMATION: Synthetic polynucleotide

<400> SEQUENCE: 62 tggaat                                                                    6

<210> SEQ ID NO 63
<211> LENGTH: 900
<212> TYPE: DNA
<213> ORGANISM: Homo sapiens

<400> SEQUENCE: 63

```
ccatagtgct tcacgtgttc tatctttgaa ttctgctaat ttctcaaaga ttgtgctaag      60
tgccttaaat aagacaatgt ttctttgcca ctggtgtctg aagtttcctt tgacattatc     120
tttcaagtct ggtgcagtgc aaatgaagat ttttcctcca gctattattc aaaagaactg     180
agatggctcc ctagtatata tactgtacac acacacatgc acactagttg aacatataga     240
atgccacata attttatgta aactaaagag atatctaaaa agcaaagcat catacctgat     300
gggcagcttc aagtgatttc aaagtcagtt gtagtctatt aagatgggaaa atccctaaaa    360
aagagtcact ttttcttaat gtatactatg gtaatgtcag agtaaatttc cagaaacctc     420
attttgaatt ctgatgacat tctcttacag ctcctcatgt ggaattctta agaccactca     480
ccgaccttca agttagagaa aaagaaatgg ctcgatttga gtgtgaactt tcccgagaaa     540
atgctaaggt ctgtgactgt atacctgtca tcttgtactg tcaaataact ttatatttac     600
ttttggtcta gccaaaatgg aaaaaaaaaa gttagtcaca acttctctgg tcaccacttt     660
acttttaaag ataattgtag tataaaatgt attcttgact ttaattgctc tcttttttagt    720
attattaatt tactattact tgaaaaacac tggactcaca atcaggagat ttagatatta     780
gtttgaacca tatgaaagtg ctgttttctt agatcagaaa gtcaaatatc agcaattata     840
tttctttcaa ctaagtacct cctgttgcta ttaactacca ttggcaagtt tcttcaagtc     900
```

<210> SEQ ID NO 64
<211> LENGTH: 21
<212> TYPE: DNA
<213> ORGANISM: Artificial Sequence
<220> FEATURE:
<223> OTHER INFORMATION: Spacer sequence

<400> SEQUENCE: 64
ttagataaaa tattggcact c                                                  21

<210> SEQ ID NO 65
<211> LENGTH: 6
<212> TYPE: DNA
<213> ORGANISM: Artificial Sequence
<220> FEATURE:
<223> OTHER INFORMATION: Synthetic polynucleotide

<400> SEQUENCE: 65 tggaat                                                                    6

<210> SEQ ID NO 66
<211> LENGTH: 21
<212> TYPE: DNA
<213> ORGANISM: Artificial Sequence
<220> FEATURE:
<223> OTHER INFORMATION: Spacer sequence

<400> SEQUENCE: 66
tatatattca gagtttggct t                                                  21

<210> SEQ ID NO 67
<211> LENGTH: 6
<212> TYPE: DNA
<213> ORGANISM: Artificial Sequence
<220> FEATURE:
<223> OTHER INFORMATION: Synthetic polynucleotide

<400> SEQUENCE: 67 ttgggt                                                                    6

<210> SEQ ID NO 68
<211> LENGTH: 21
<212> TYPE: DNA
<213> ORGANISM: Artificial Sequence
<220> FEATURE:
<223> OTHER INFORMATION: Spacer sequence

<400> SEQUENCE: 68
aaattaccca aaagccaaac t                                                  21

<210> SEQ ID NO 69
<211> LENGTH: 6
<212> TYPE: DNA
<213> ORGANISM: Artificial Sequence
<220> FEATURE:
<223> OTHER INFORMATION: Synthetic polynucleotide

<400> SEQUENCE: 69 ctgaat                                                                    6

<210> SEQ ID NO 70
<211> LENGTH: 21
<212> TYPE: DNA
<213> ORGANISM: Artificial Sequence
<220> FEATURE:
<223> OTHER INFORMATION: Spacer sequence

<400> SEQUENCE: 70
aaagacacaa aagtatatat t                                                  21

<210> SEQ ID NO 71
<211> LENGTH: 6
<212> TYPE: DNA
<213> ORGANISM: Artificial Sequence
<220> FEATURE:
<223> OTHER INFORMATION: Synthetic polynucleotide

<400> SEQUENCE: 71 cagagt                                                                    6

<210> SEQ ID NO 72
<211> LENGTH: 21
<212> TYPE: DNA
<213> ORGANISM: Artificial Sequence
<220> FEATURE:
<223> OTHER INFORMATION: Spacer sequence

<400> SEQUENCE: 72
agcaaaatta acgtggatat g                                                  21

<210> SEQ ID NO 73
<211> LENGTH: 6
<212> TYPE: DNA
<213> ORGANISM: Artificial Sequence
<220> FEATURE:

```
<223> OTHER INFORMATION: Synthetic polynucleotide

<400> SEQUENCE: 73 tagaat                                                                        6

<210> SEQ ID NO 74
<211> LENGTH: 21
<212> TYPE: DNA
<213> ORGANISM: Artificial Sequence
<220> FEATURE:
<223> OTHER INFORMATION: Spacer sequence

<400> SEQUENCE: 74
acatatccac gttaattttg c                                                      21

<210> SEQ ID NO 75
<211> LENGTH: 6
<212> TYPE: DNA
<213> ORGANISM: Artificial Sequence
<220> FEATURE:
<223> OTHER INFORMATION: Synthetic polynucleotide

<400> SEQUENCE: 75 tagaat                                                                        6

<210> SEQ ID NO 76
<211> LENGTH: 21
<212> TYPE: DNA
<213> ORGANISM: Artificial Sequence
<220> FEATURE:
<223> OTHER INFORMATION: Spacer sequence

<400> SEQUENCE: 76 cgttaattttt gctagaatag t                                                     21

<210> SEQ ID NO 77
<211> LENGTH: 6
<212> TYPE: DNA
<213> ORGANISM: Artificial Sequence
<220> FEATURE:
<223> OTHER INFORMATION: Synthetic polynucleotide

<400> SEQUENCE: 77 gtgagt                                                                        6

<210> SEQ ID NO 78
<211> LENGTH: 25
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(21)
<223> OTHER INFORMATION: n is a, c, g, or t

<400> SEQUENCE: 78
nnnnnnnnnn nnnnnnnnnn ngrrt                                                  25
```